US012582625B2

(12) United States Patent     (10) Patent No.:   US 12,582,625 B2

Gerner et al.     (45) Date of Patent:    Mar. 24, 2026

(54) METHODS FOR TREATING NEUROBLASTOMA

(71) Applicants: ARIZONA BOARD OF REGENTS ON BEHALF OF THE UNIVERSITY OF ARIZONA, Tucson, AZ (US); USWM, LLC, Louisville, KY (US)

(72) Inventors: Eugene Gerner, Tucson, AZ (US); Elizabeth Bruckheimer, Tucson, AZ (US); Giselle Saulnier Sholler, Hershey, PA (US)

(73) Assignees: USWM, LLC, Louisville, KY (US); THE ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 18/999,227

(22) Filed: Dec. 23, 2024

(65) Prior Publication Data

US 2025/0127742 A1     Apr. 24, 2025

Related U.S. Application Data

(63) Continuation of application No. 18/230,601, filed on Aug. 4, 2023, which is a continuation of application No. 17/147,697, filed on Jan. 13, 2021, now abandoned, which is a continuation of application No. 15/550,595, filed as application No. PCT/US2016/017751 on Feb. 12, 2016, now abandoned.

(Continued)

(51) Int. Cl.

| | |
|---|---|
| *C12Q 1/68* | (2018.01) |
| *A61K 31/192* | (2006.01) |
| *A61K 31/198* | (2006.01) |
| *A61K 31/203* | (2006.01) |
| *A61K 31/415* | (2006.01) |
| *A61K 31/616* | (2006.01) |
| *A61K 31/69* | (2006.01) |
| *A61K 31/7048* | (2006.01) |
| *A61K 39/395* | (2006.01) |
| *A61K 45/06* | (2006.01) |
| *A61P 35/00* | (2006.01) |
| *C07H 21/04* | (2006.01) |
| *C07K 16/30* | (2006.01) |
| *C12Q 1/6886* | (2018.01) |
| *A61K 39/00* | (2006.01) |

(52) U.S. Cl.

CPC .......... *A61K 31/198* (2013.01); *A61K 31/192* (2013.01); *A61K 31/203* (2013.01); *A61K 31/415* (2013.01); *A61K 31/616* (2013.01);

*A61K 31/69* (2013.01); *A61K 31/7048* (2013.01); *A61K 39/395* (2013.01); *A61K 39/39558* (2013.01); *A61K 45/06* (2013.01); *A61P 35/00* (2018.01); *C07K 16/3084* (2013.01); *C12Q 1/6886* (2013.01); *A61K 2039/505* (2013.01); *A61K 2300/00* (2013.01); *C12Q 2600/106* (2013.01); *C12Q 2600/156* (2013.01)

(58) Field of Classification Search

None

See application file for complete search history.

(56) References Cited

U.S. PATENT DOCUMENTS

| | | | |
|---|---|---|---|
| 4,309,442 | A | 1/1982 | Bey |
| 4,330,559 | A | 5/1982 | Bey |

(Continued)

FOREIGN PATENT DOCUMENTS

| | | | |
|---|---|---|---|
| CA | 2165481 A1 | 1/1995 | |
| CA | 2345112 A1 | 3/2000 | |

(Continued)

OTHER PUBLICATIONS

Lozier et al. (Oncotarget, vol. 6, No. 1, pp. 196-206, Published online Nov. 2014). (Year: 2014).*

(Continued)

*Primary Examiner* — Jeanine A Goldberg

(74) *Attorney, Agent, or Firm* — Gray Ice Higdon

(57) ABSTRACT

The present invention provides methods and kits a) for preventing and/or treating neuroblastoma (e.g., high-risk neuroblastoma) that is linked, in part, to high levels of ODC activity and increased cellular polyamine content, b) for predicting cancer patient survival, especially cancer patients whose cancer is linked, in part, to high levels of ODC activity and increased cellular polyamine contents, and c) for selecting treatment options for such patients based on the allelic nucleotide sequence or SNP at positions +263 and/or +316 of the ODC1 gene. The invention also provides, cancer treatment methods comprising the determination of the ODC1 genotype at the +263 and/or +316 positions, as a means to guide treatment selection, which includes, in some aspects the administration of pharmaceutically effective amounts of α-difluoromethylornithine (DFMO), either as a monotherapy or in combination with one or more other drugs. In addition, the present invention provides methods for preventing and/or treating patients that have been determined to have cancer stem cells, such as patients in cancer remission that are at risk for relapse.

30 Claims, 8 Drawing Sheets

Related U.S. Application Data

(60) Provisional application No. 62/115,413, filed on Feb. 12, 2015, provisional application No. 62/154,804, filed on Apr. 30, 2015.

(56) References Cited

U.S. PATENT DOCUMENTS

| | | | |
|---|---|---|---|
| 4,413,141 A | 11/1983 | Bey | |
| 4,499,072 A | 2/1985 | Sunkara | |
| 4,859,452 A | 8/1989 | Ajani | |
| 4,925,835 A | 5/1990 | Heston | |
| 5,002,879 A | 3/1991 | Bowlin | |
| 5,814,625 A | 9/1998 | Larson | |
| 5,843,929 A | 12/1998 | Larson | |
| 6,258,845 B1 | 7/2001 | Gerner | |
| 6,573,290 B1 | 6/2003 | Love | |
| 6,602,910 B2 | 8/2003 | Levenson | |
| 6,753,422 B2 | 6/2004 | O'Brien | |
| 7,273,888 B2 | 9/2007 | Ramesh | |
| 7,592,319 B2 | 9/2009 | Li | |
| 8,329,636 B2 * | 12/2012 | Gerner | A61K 31/192 |
| | | | 514/1 |
| 9,072,778 B2 | 7/2015 | Bachmann | |
| 9,121,852 B2 * | 9/2015 | Gerner | C12Q 1/6886 |
| 9,937,141 B2 * | 4/2018 | Gerner | A61K 31/192 |
| 10,151,756 B2 * | 12/2018 | Gerner | C12Q 1/18 |
| 10,655,183 B2 | 5/2020 | Gerner | |
| 10,845,366 B2 * | 11/2020 | Gerner | A61K 31/192 |
| 2002/0081611 A1 | 6/2002 | O'Brien | |
| 2002/0110590 A1 | 8/2002 | Shaked | |
| 2005/0032726 A1 | 2/2005 | Li | |
| 2005/0059690 A1 | 3/2005 | Newman | |
| 2009/0203784 A1 * | 8/2009 | Bachmann | A61K 31/365 |
| | | | 514/564 |
| 2010/0150910 A1 | 6/2010 | Birkle | |
| 2010/0197718 A1 | 8/2010 | Pisano | |
| 2010/0317708 A1 | 12/2010 | Gerner | |
| 2011/0256161 A1 | 10/2011 | Burns | |
| 2012/0259013 A1 | 10/2012 | Motwani | |
| 2013/0157972 A1 | 6/2013 | Cheng | |
| 2013/0164751 A1 * | 6/2013 | Gerner | A61P 35/00 |
| | | | 435/6.11 |
| 2013/0216528 A1 | 8/2013 | Cheung | |
| 2013/0217743 A1 | 8/2013 | Raj | |
| 2015/0301060 A1 | 10/2015 | Gerner | |
| 2016/0213634 A1 | 7/2016 | Gerner | |
| 2017/0362658 A1 | 12/2017 | Gerner | |
| 2019/0046484 A1 | 2/2019 | Gerner | |
| 2021/0378999 A1 | 12/2021 | Gerner | |
| 2024/0165063 A1 | 5/2024 | Gerner | |

FOREIGN PATENT DOCUMENTS

| | | | | |
|---|---|---|---|---|
| EP | 2438919 A1 | 4/2012 | | |
| JP | 2002509884 A | 4/2002 | | |
| JP | 2002526468 A | 8/2002 | | |
| JP | 2005501881 A | 1/2005 | | |
| JP | 2007537719 A | 12/2007 | | |
| JP | 2010505909 A | 2/2010 | | |
| JP | 2012511052 A | 5/2012 | | |
| JP | 2016515519 A | 5/2016 | | |
| WO | 9825603 A1 | 6/1998 | | |
| WO | 9949859 A1 | 10/1999 | | |
| WO | 0168076 A2 | 9/2001 | | |
| WO | 0215895 A2 | 2/2002 | | |
| WO | 03020209 A2 | 3/2003 | | |
| WO | 2005070967 A2 | 8/2005 | | |
| WO | 2009048932 A2 | 4/2009 | | |
| WO | 2010056919 A2 | 5/2010 | | |
| WO | 2010132817 A1 | 11/2010 | | |
| WO | 2011135459 A2 | 11/2011 | | |
| WO | WO-2014070767 A1 * | 5/2014 | | A61K 31/192 |
| WO | 2014140072 A1 | 9/2014 | | |
| WO | 2014144763 A2 | 9/2014 | | |
| WO | WO-2015195120 A1 * | 12/2015 | | A61K 31/192 |
| WO | 2017075576 A1 | 5/2017 | | |

OTHER PUBLICATIONS

Johansson et al. (J. of Pharmacokinetics and Pharmacodynamics, vol. 40, pp. 117-128, 2013). (Year: 2013).*

Sholler (Abstract LB-179: Phase I trial of relapsed neuroblastoma with DFMO alone and in combination with etoposide, vol. 73, Supplement 8, LB-179, Apr. 15, 2013). (Year: 2013).*

Sholler et al. (PLoS, vol. 10, No. 5, e0127246, May 2015).*

Jeter et al. (Difluoromethylornithine: The proof is in the polyamines, Cancer Prev. Res. vol. 5, No. 12, pp. 1341-1344, 2012) (Year: 2012).*

Gerner et al., "Gastrointestinal tissue polyamine contents of patients with Barrett's esophagus treated with alpha-difluoromethylornithine," Cancer Epidemiol. Biomarkers Prev., 3:325-330, dated 1994.

Gerner, "Impact of dietary amino acids and polyamines on intestinal carcinogenesis and chemoprevention in mouse models", Biochemical Society Transactions, 35(2):322-325, dated 2007.

Gerner, E. W., et al. "Rationale for, and design of, a clinical trial targeting polyamine metabolism for colon cancer chemoprevention." Amino acids 33.2: 189-195, dated 2007.

Giardiello et al., "Ornithine decarboxylase and polyamines in familial adenomatous polyposis," Cancer Res., (57):199-201, dated 1997.

Greenberg et al., "Reduced risk of large bowel adenomas among aspirin users," J. Natl. Cancer Inst., 85:912-916, dated 1993.

Guo et al., "Functional analysis of human ornithine decarboxylase alleles," Cancer Res., 60(22):6314-6317, dated 2000.

Hanif et al., "Effects of nonsteroidal anti-inflammatory drugs on proliferation and on induction of apoptosis in colon cancer cells by a prostaglandin-independent pathway," Biochemical Pharmacology, (52):237-245, dated 1996.

Hessels et al., "Microbial flora in the gastrointestinal tract abolishes cytostatic effects of a-difluoromethylornithine in vivo," Int. J. Cancer, 43: 1155-1164, dated 1989.

Hixson et al., "Ornithine decarboxylase and polyamines in colorectal neoplasia and mucosa," Cancer Epidemiology Biomarkers Prev., 2:369-374, dated 1993.

Hixson et al., "Sources of variability in measurements of ornithine decarboxylase activity and polyamine contents in colorectal mucosa," Cancer Epidemoil. Biomarkers Prev., 3:317-323, dated 1994.

Hogarty et al., "ODC1 is a critical determinant of MYCN oncogenesis and a therapeutic target in neuroblastoma," Cancer Res., 68:9735-9745, dated 2008.

Hubner et al., "Ornithine decarboxylase G316A genotype is prognostic for colorectal adenoma recurrence and predicts efficacy of aspirin chemoprevention," Clin. Cancer Res., 14(8):2303-9, dated 2008.

Hughes, et al., "Polyamines reverse non-steroidal anti-inflammatory drug-induced toxicity in human colorectal cancer cells", Biochem J, 374:481-8, dated 2003.

Ignatenko et al., "Dietary putrescine reduces the intestinal anticarcinogenic activity of sulindac in a murine model of familial adenomatous polyposis," Nutrition and Cancer, 56(2): 172-181, dated 2006.

Ignatenko et al., "Role of c-Myc in intestinal tumorigenesis of the ApcMin/+ mouse," Cancer Biol. Ther., 5(12):1658-64, dated 2006.

International Preliminary Report on Patentability, issued in International Application No. PCT/US2016/017751, dated Aug. 24, 2017.

Iwamoto et al., "Expression of beta-catenin and full-length APC protein in normal and neoplastic colonic tissues," Carcinogenesis, 21:1935-40, dated 2000.

Jass et al., "Emerging concepts in colorectal neoplasia," Gastroenterology, 123:862-876, dated 2002.

Johnson et al. "Relationships between drug activity in NCI preclinical in vitro and in vivo models and early clinical trials." British Journal of Cancer 84.10: 1424, dated 2001.

(56)        References Cited

OTHER PUBLICATIONS

Kawamori, et al., "Chemopreventive activity of celecoxib, a specific cyclooxygenase-2 inhibitor, against colon carcinogenesis," Cancer Research, 58:409-412, dated 1998.

Kelloff et al., "Chemopreventive drug development: perspectives and progress," Cancer Epidemiology Biomarks and Prevention, 3:85-98, dated 1994.

Kelloff et al., "New agents for cancer chemoprevention," J. Cell. Biochem., 265:1-28, dated 1996.

Kelloff et al., "Perspectives on chemoprevention agent selection and short term clinical prevention trials," European J. Cancer Prevention, 5(Supp. 2):79-85, dated 1996.

Kingsnorth et al., "Effects of alpha-difluoromethylornithine and 5-fluorouracil on the proliferation of a human colon adenocarcinoma cell line," Cancer Res., 43(9):4035-8, dated 1983.

Koomoa, Dana-Lynn T., et al. "DFMO/eflornithine inhibits migration and invasion downstream of MYCN and involves p27Kip1 activity in neuroblastoma." International Journal of Oncology 42.4: 1219-1228, dated 2013.

Koomoa, Dana.-Lynn T., et al. "Inhibition of S-adenosylmethionine decarboxylase by inhibitor SAM486A connects polyamine metabolism with p53-Mdm2-Akt/protein kinase B regulation and apoptosis in neuroblastoma." Molecular Cancer Therapeutics 8.7: 2067-2075, dated 2009.

Koomoa, Dana-Lynn T., et al. "Ornithine decarboxylase inhibition by a-difluoromethylornithine activates opposing signaling pathways via phosphorylation of both Akt/protein kinase B and p271Kip1 in neuroblastoma." Cancer Research 68.23: 9825-9831, dated 2008.

Kruh et al., "Expression Pattern of MRP in Human Tissues and Adult Solid Tumor Cell Lines," J. Natl. Cancer Inst., 87(16):1256-1258, dated 1995.

Ladenheim et al., "Effect of sulindac on sporadic colonic polyps," Gastroenterology, 108:1083-1087, dated 1995.

Lange, Ingo, et al. "Novel interaction of ornithine decarboxylase with sepiapterin reductase regulates neuroblastoma cell proliferation." Journal of Molecular Biology 426.2: 332-346, dated 2014.

Lanza et al., "Peptic ulcer and gastrointestinal hemorrhage associated with nonsteroidal anti-inflammatory drug use in patients younger than 65 years. A large health maintenance organization cohort study," Arch. Intern. Med., 155:1371-1377, dated 1995.

Le et al., "Effects of socioeconomic status and treatment disparities in colorectal cancer survival," Cancer Epidemiol. Biomarkers Prev., 17:1950-62, dated 2008.

Levin, Victor A., et al. "Relationship between ornithine decarboxylase levels in anaplastic gliomas and progression-free survival in patients treated with DFMO—PCV chemotherapy." International journal of cancer 121.10: 2279-2283, dated 2007.

Levin, Victor A., et al. "Phase III randomized study of postradiotherapy chemotherapy with combination a-difluoromethylornithine-PCV versus PCV for anaplastic gliomas." Clinical Cancer Research 9.3: 981-990, dated 2003.

Levin, Victor A., et al. "Phase III randomized study of postradiotherapy chemotherapy with a-difluoromethylornithine-procarbazine, N-(2-chloroethyl)-N'-cyclohexyl-N-nitrosurea, vincristine (DFMO-PCV) versus PCV for glioblastoma multiforme." Clinical Cancer Research 6.10: 3878-3884, dated 2000.

Linsalata et al., "Nutritional factors and polyamine metabolism in colorectal cancer," Nutrition, 24:382-389, dated 2008.

Lipkin, "New rodent models for studies of chemopreventive agents," J. Cell Biochem. Suppl., 28-29:144-7, dated 1997.

Love et al., "Randomized phase I chemoprevention dose-seeking study of alpha-difluoromethylornithine," J. Natl. Cancer Inst., 85:732-7, dated 1993.

Lozier et al., "Targeting ornithine decarboxylase reverses the LIN28/Let-7 axis and inhibits glycolytic metabolism in neuroblastoma," Oncotarget, 6:196-206, dated 2015.

Luk and Baylin, "Ornithine decarboxylase as a biologic marker in familial colonic polyposis," N. Engl. J. Med., 311(2):80-83, dated 1984.

Lupulescu, "Control of precancer cell transformation into cancer cells: its relevance to cancer prevention," Cancer Detect. Prev., 20(6):634-637, dated 1996.

Mackenzie, Gerardo G., et al. "Phospho-sulindac (OXT-328) combined with difluoromethylornithine prevents colon cancer in mice." Cancer prevention research 4.7: 1052-1060, dated 2011.

Martinez et al., "Pronounced reduction in adenoma recurrence associated with aspirin use and a polymorphism in the ornithine decarboxylase gene," Proc. Natl. Acad. Sci. USA, 100:7859-64, dated 2003.

Matsubara et al., "Association between high levels of ornithine decarboxylase activity and favorable prognosis in human colorectal carcinoma," Clinical Cancer Res., 1:665-71, dated 1995.

McGarrity et al., "Colonic polyamine content and ornithine decarboxylase activity as markers for adenomas," Cancer, 66:1539-1543, dated 1990.

McLaren et al., "Longitudinal assessment of air conduction audiograms in a phase III clinical trial of difluoromethylornithine and sulindac for prevention of sporadic colorectal adenomas," Cancer Prev. Res., 1(7):514-21, dated 2008.

Melino, G . . . et al. "Retinoic acid and alpha-difluoromethylornithine induce different expression of neural-specific cell adhesion molecules in differentiating neuroblastoma cells." Progress in Clinical and Biological Research 366: 283-291, dated 1991.

Melino, Gennaro, Maria Paola Ceru, and Mauro Piacentini. "Correlation between transglutaminase activity and polyamine levels in human neuroblastoma cells: effect of retinoic acid and a-difluoromethylornithine." Experimental Cell Research 179.2: 429-445, dated 1988.

Meyskens and Gerner, "Development of difluoromethylornithine as a chemoprevention agent for the management of colon cancer," J. Cell. Biochem., 22:126-131, dated 1995.

Meyskens et al., "Development of difluoromethylornithine (DFMO) as a chemoprevention agent," Clin. Cancer Res., 5:945-951, dated 1999.

Meyskens et al., "Difluoromethylornithine plus sulindac for the prevention of sporadic colorectal adenomas: a randomized placebo-controlled, double-blind trial," Cancer Prev. Res., 1(1):32-8, dated 2008.

Meyskens et al., "Dose de-escalation chemoprevention trial of alpha-difluoromethylornithine in patients with colon polyps," J. Natl. Cancer Inst., 86(15):1122-1130, dated 1994.

Meyskens et al., "Effect of alpha-difluoromethylornithine on rectal mucosal levels of polyamines in a randomized, double-blinded trial for colon cancer prevention," J. Natl. Cancer Inst., 90(16):1212-8, dated 1998.

Muscat et al., "Nonsteroidal antiinflammatory drugs and colorectal cancer," Cancer, 74:1847-1854, drafted 1994.

Nishimura et al., "Independent roles of eIF5A and polyamines in cell proliferation," Biochem. J., 385:779-785, dated 2005.

Norris, M. D. G., et al, "The ornithine decarboxylase G317A polymorphism is prognostic of outcome in primary neuroblastoma and differentially affects promoter binding by the MYCN oncogene." Advances in Neuroblastoma Research, dated 2014.

O'Brien et al., "Differences in ornithine decarboxylase and androgen receptor allele frequencies among ethnic groups," Molec. Carcinog., 41(2): 120-3, dated 2004.

Office Communication issued in European Patent Application No. 16749956.5, dated Sep. 12, 2018.

Office Communication issued in U.S. Appl. No. 12/780,592, dated Mar. 20, 2012.

Office Communication issued in U.S. Appl. No. 12/780,592, dated Aug. 14, 2012.

Office Communication issued in U.S. Appl. No. 13/709,753, dated Sep. 10, 2014.

Office Communication issued in U.S. Appl. No. 13/709,753, dated Apr. 21, 2015.

Office Communication issued in U.S. Appl. No. 14/841,750, dated Apr. 21, 2017.

Office Communication issued in U.S. Appl. No. 14/841,750, dated Nov. 24, 2017.

Office Communication issued in U.S. Appl. No. 15/319,857, dated Sep. 13, 2018.

(56) References Cited

OTHER PUBLICATIONS

Pardali and Moustakas, "Actions of TGF-beta as tumor suppressor and pro-metastatic factor in human cancer," Biochimica et Biophysica Acta, 1775:21-62, dated 2007.

Pasricha et al., "The effects of sulindac on colorectal proliferation and apoptosis in familial adenomatous polyposis," Gastroenterology, 109:994-998, dated 1995.

Paz et al., "Plyamines are oncometabolites that regulate the LIN28/let-7 pathway in colorectal cancer cells," Molecular Carcinogensis, dated 2013.

PCT International Search Report and Written Opinion, issued in International application No. PCT/US10/34974, dated Jul. 2, 2010.

PCT International Search Report and Written Opinion, issued in International Application No. PCT/US2014/042979, dated Jan. 29, 2015.

PCT International Search Report and Written Opinion, issued in International Application No. PCT/US2016/017751, dated Jul. 14, 2016.

Peel et al., "Characterization of hereditary nonpolyposis colorectal cancer families from a population-based series of cases," J. Natl. Cancer Inst., 92:1517-22, dated 2000.

Pegg, "Recent advances in the biochemistry of polyamines in eukaryotes," Biochem., 234(2):249-262, dated 1986.

Piazza et al., "Antineoplastic drugs sulindac sulfide and sulfone inhibit cell growth by inducing apoptosis," Cancer Res., (55):3110-3116, dated 1995.

Piazza et al., "Apoptosis primarily accounts for the growth-inhibitory properties of sulindac metabolites and involves a mechanism that is independent of cyclooxygenase inhibition, cell cycle arrest, and p53 induction," Cancer Res., (57):2452-2459, dated 1997.

Piazza et al., "Sulindac sulfone inhibits azoxymethane-induced colon carcinogenesis in rats without reducing prostaglandin levels," Cancer Res., (57):2909-2915, dated 1997.

Pollard and Luckert, "Prevention and treatment of primary intestinal tumors in rats by piroxicam," Cancer Res., 49:6471-6473, dated 1989.

Porter et al., "Polyamine biosynthetic activity in normal and neoplastic human colorectal tissue," Cancer, 60:1275-1281, dated 1987.

Prieto, Jenaro Garcia-Huidobro. "Molecular and Functional Consequences of Gentic Variability in the Ornithine Decarboxylase Gene in Colorectal Cancer." 2013.

Pugh, Trevor J. et al. "The genetic landscape of high-risk neuroblastoma." Nature Genetics 45.3: 279, dated 2013.

Quemener et al., "Polyamine deprivation: a new tool in cancer treatment", Institute of Anticancer Research, 14:443-448, dated 1994.

Raj et al., "Role of dietary polyamines in a phase III clinical trial of difluoromethylornithine (DFMO) and sulindac for prevention of sporadic colorectal adenomas", British Journal of Cancer, 108(3):512-518, dated 2013.

Reddy et al., "Chemoprevention of colon carcinogenesis by concurrent administration of piroxicam, a nonsteroidal antiinflammatory drug with D,L-alpha-difluoromethylornithine, an ornithine decarboxylase inhibitor, in diet," Cancer Research, 50:2562-2568, dated 1990.

Reddy et al., "Dose-related inhibition of colon carcinogenesis by dietary piroxicam, a nonsteroidal antiinflammatory drug, during different stages of rat colon tumor development," Cancer Res., 47:5340-5346, dated 1987.

Rial, Nathaniel S., Frank L. Meyskens, and Eugene W. Gerner. "Polyamines as mediators of APC-dependent intestinal carcinogenesis and cancer chemoprevention." Essays in Biochemistry 46: 111-124, dated 2009.

Roberts and Wakefield, "The two faces of transforming growth factor beta in carcinogenesis," Proc. Natl. Acad. Sci. USA, 100:8621-3, dated 2003.

Rounbehler et al., "Targeting ornithine decarboxylase impairs development of MYCN-amplified neuroblastoma," Cancer Res., 69:547-553, dated 2009.

Saletta et al., "Molecular profiling of childhood cancer: Biomarkers and novel therapies," BBA Clinical, 1:59-77, dated 2014.

Samaha et al., "Modulation of apopotsosi by sulindac, curcumin, phenylethyl-3-methylcaffeate, and 6-phenylhexyl isothiocyanate, apoptotic index as a biomarker in colon cancer chemoprevention and promotion," Cancer Res., (57):1301-1305, dated 1997.

Samal, Katherine, et al. "AMXT-1501, a novel polyamine transport inhibitor, synergizes with DFMO in inhibiting neuroblastoma cell proliferation by targeting both ornithine decarboxylase and polyamine transport." International Journal of Cancer 133.6: 1323-1333, dated 2013.

Sausville, Edward A., and Angelika M. Burger. "Contributions of human tumor xenografts to anticancer drug development." Cancer Research 66.7: 3351-3354, dated 2006.

Seiler and Knodgen, "High-performance liquid chromatographic procedure for the simultaneous determination of the natural polyamines and their monoacetyl derivatives," J. Chromatogr., 221(2):227-235, dated 1980.

Seiler et al., "Endogenous and exogenous polyamines in support of tumor growth", Cancer Research, 50:5077-5083, dated 1990.

Sholler et al., [abstract]. In: Proceedings of the 104th Annual Meeting of the American Association for Cancer Research; Washington, DC. Philadelphia (PA): AACR; Cancer Res 2013;73(8 Suppl):Abstract nr LB-179. doi:10.1158/1538-7445, dated Apr. 6, 2013.

Sholler, Giselle L. Saulnier, et al. "A phase I trial of DFMO targeting polyamine addiction in patients with relapsed/refractorr neuroblastoma." PLoS One 10.5: e0127246, dated 2015.

Silva et al., "Role of peripheral polyamines in the development of inflammatory pain," Biochemical Pharmacology, 82:269-277, dated 2011.

Simoneau et al., "Alpha-difluoromethylornithine and polyamine levels in the human prostate: results of a phase IIa trial," J. Natl. Cancer Inst., 93:57-9, dated 2001.

Simoneau et al., "The effect of difluoromethylornithine on decreasing prostate size and polyamines in men: results of a year-long phase IIb randomized placebo-controlled chemoprevention trial," Cancer Epidemiol. Biomarkers Prev., 17:292-9, dated 2008.

Singh and Reddy, "Molecular markers in chemoprevention of colon cancer. Inhibition of expression of ras-p21 and p53 by sulindac during azoxymethane-induced colon carcinogenesis," Annals. NY Acad. Sci., (768):205-209, dated 1995.

Scholler et al., Abstract LB-179: Phase I trial of relapsed neuroblastoma with DFMO alone and in combination with etoposide, American Association for Cancer Research, vol. 73, Issue 8 Suppl., 4 pages, dated Apr. 2013.

Scholler et al., A Phase I Trial of DFMO Targeting Polyamine Addiction in Patients with Relapsed/Refractory Neuroblastoma, PLoS One, 20 pages, dated May 27, 2015.

Lozier et al., Targeting ornithine decarboxylase reverses the LIN28/Let-7 axis and inhibits glycolytic metabolism in neuroblastoma, Oncotarget, vol. 6, No. 1, 196-206, 11 pages, dated Nov. 15, 2014.

Evageliou and Hogarty, Disrupting Polyamine Homeostasis as a Therapeutic Strategy for Neuroblastoma, Clin Cancer Res 2009;15(19), 7 pages, dated Oct. 1, 2009.

Gamble et al., Polyamine pathway inhibition as a novel therapeutic approach to treating neuroblastoma, Frontiers in Oncology, vol. 2, Article 162, 10 pages, date Nov. 16, 2012.

Hogarty et al., ODC1 is a critical determinant of MYCN oncogenesis and a therapeutic target in neuroblastoma, Cancer Res; 68(23): 9735-9745, 25 pages, dated Dec. 1, 2008.

Meyskens and Gerner, Development of Difluoromethylornithine (DFMO) as a Chemoprevention Agent, Clinical Cancer Research, vol. 6, 945-951, 8 pages, dated May 1999.

Rounbehler et al., Targeting Ornithine Decarboxylase Impairs Development of MYCN-Amplified Neuroblastoma, Cancer Res 2009; 69: (2), 8 pages, dated Jan. 15, 2009.

Zell et al., Associations of a polymorphism in the ornithine decarboxylase gene with colorectal cancer survival, Clin Cancer Res.; 15(19): 6208-621, 20 pages, dated Oct. 1, 2009.

VANIQATM Label, 10 pages, dated Jul. 27, 2000.

Johansson et al., J. of Pharmacokinetics and Pharmacodynamics, vol. 40, pp. 117-128, dated 2013.

(56)                References Cited

OTHER PUBLICATIONS

Bachmann, Abstract LB-179: Phase I Trial of Relapsed Neuroblastoma with DFMO Alone and in Combination with Etoposide, vol. 73, Supplement 8, LB-179, Apr. 15, 2013, dated Apr. 15, 2015.
"NCT01245816" retrieved from clinicaltrials.gov archive on Jan. 20, 2017, dated Apr. 23, 2015.
"NCT01483144" retrieved from clinicaltrials.gov archive on Jan. 20, 2017, dated Jul. 28, 2015.
"VANIQA" (eflornithine hydrochloride) Prescription Information, dated Jul. 2010.
Alberts et al., Do NSAIDs exert their colon cancer chemoprevention activities through the inhibition of mucosal prostaglandin synthetase?, J. Cell. Biochem. Supp., (22): 18-23, dated 1995.
Arber et al., "A K-ras oncogene increases resistance to sulindac-induces apoptosis in rat enterocytes," Gastroenterology, 113: 1892-1990, dated 1997.
Babbar et al., "Induction of spermidine/spermine N1-acetyltransferase (SSAT) by aspirin in Caco-2 colon cancer cells," Biochem. J., 394:317-24, dated 2006.
Bachmann, Andre S., Dirk Geerts, and Giselle L. Saulnier Sholler. "Neuroblastoma: Ornithine decarboxylase and polyamines are novel targets for therapeutic intervention." Neuroblastoma. Springer, Dordrecht, 91-103, dated 2012.
Bachrach et al., "Polyamines: new cues in cellular signal transduction," News Physiol. Sci., 16:106-109, dated 2001.
Barry et al., "Ornithine decarboxylase polymorphism modification of response to aspirin treatment for colorectal adenoma prevention," J. Natl. Cancer Inst., 98(20):1494-500, dated 2006.
Basuroy and Gerner, "Emerging concepts in targeting the polyamine metabolic pathway in epithelial cancer chemoprevention and chemotherapy," J. Biochem., 139:27-33, dated 2006.
Bedi et al., "Inhibition of apoptosis during development of colorectal cancer," Cancer Res., 55(9):1811-1816, dated 1995.
Bello-Fernandez et al., "The ornithine decarboxylase gene is a transcriptional target of c-Myc," Proc. Natl. Acad. Sci. USA, 90:7804-8, dated 1993.
Boolbol, et al., "Cyclooxygenase-2 overexpression and tumor formation are blocked by sulindac in a murine model of familial adenomatous polyposis," Cancer Research, 56:2556-2560, dated 1996.
Boone et al., "Biomarker end-points in cancer chemoprevention trails," IARC Scientific Publications, 142:273-280, dated 1997.
Bosslet, K., et al. "Monoclonal antibodies against epitopes on ganglioside GD 2 and its lactones." Cancer Immunology, Immunotherapy 29.3: 171-178 1989.
Boyle et al., "Polyamine contents in rectal and buccal mucosae in humans treated with oral difluoromethylornithine," Cancer Epidemiol. Biomarkers Prev., 1:131-135, dated 1992.
Brabender et al., "Upregulation of ornithine decarboxylase mRNA expression in Barrett's esophagus and Barrett's-associated adenocarcinoma," J. Gastrointest. Surg., 5:174-181; discussion 182, dated 2001.
Braverman et al., "Ornithine decarboxylase: an unreliable marker for the identification of population groups at risk for colonic neoplasia," Am. J. Gastronenterology, 85:723-726, dated 1990.
Castel et al., "Treatment of high-risk neuroblastoma with anti-GD2 antibodies," Clinical and Translational Oncology, 12:788-793, dated 2010.
Chapman, Sharon K. "Antitumor effects of vitamin A and inhibitors of ornithine decarboxylase in cultured neuroblastoma and glioma cells." Life Sciences 26.16: 1359-1366, dated 1980.
Chen, Kuang Yu, David Nau, and Alice YC Liu. "Effects of inhibitors of ornithine decarboxylase on the differentiation of mouse neuroblastoma cells." Cancer Research 43.6: 2812-2818, dated 1983.
Cheung; N. K., et al. "3F8 monoclonal antibody treatment of patients with stage 4 neuroblastoma: a phase II study." International Journal of Oncology 12.6: 1299-1605, dated 1998.
Childs et al., "Polyamine-dependent gene expression," Cell. Molec. Life Sci., 60:1394-1406, dated 2003.

Choi, Peter S., Yulin Li, and Dean W. Felsher. "Addiction to multiple oncogenes can be exploited to prevent the emergence of therapeutic resistance." Proceedings of the National Academy of Sciences 111.32: E3316-E3324, dated 2014.
Croghan et al., "Dose-related alpha-difluoromethylornithine ototoxicity," Am. J. Clin. Oncol., (14):331-5, dated 1991.
Derynck et al., "TGF-beta signaling in tumor suppression and cancer progression," Nature Genetics, 29:117-29, dated 2001.
DuBois et al., "G1 delay in cells overexpressing prostaglandin endoperoxide synthase-2," Cancer Res., 56:733-737, dated 1996.
Erdman et al., "Assessment of Mutations in Ki-ras and P53 in colon cancers from azoxymethane- and dimethylhydrazine-treated rats," Mol. Carcin., (19):137-144, dated 1997.
Erdman et al., "APC-dependent changes in expression of genes influencing polyamine metabolism, and consequences for gastrointestinal carcinogenesis, in the Min mouse," Carcinogenesis, 20(9):1709-13, dated 1999.
Ernestus, R. I., et al. "Polyamine metabolism in brain tumours: diagnostic relevance of quantitative biochemistry." Journal of Neurology, Neurosurgery & Psychiatry 71.1: 88-92, dated 2001.
Evageliou, Nicholas F., and Michael D. Hogarty. "Disrupting polyamine homeostasis as a therapeutic strategy for neuroblastoma." Clinical Cancer Research 15.19: 5956-5961, dated 2009.
Fearon et al., "A genetic model for colorectal tumorigenesis," Cell, 61:759-767, dated 1990.
Fultz and Gerner, "APC-dependent regulation of ornithine decarboxylase in human colon tumor cells," Mol. Carcinog., 34:10-8, dated 2002.
Gamble et al., "Polyamine pathway inhibition as a novel therapeutic approach to treating neuroblastoma," Frontier in Oncology, 2(162):1-10, dated 2012.
Gann et al., "Low-dose aspirin and incidence of colorectal tumors in a randomized trial," J. Natl. Cancer Inst., 85:1220-1224, dated 1993.
Geerts, Dirk, et al. "The polyamine metabolism genes ornithine decarboxylase and antizyme 2 predict aggressive behavior in neuroblastomas with and without MYCN amplification." International Journal of Cancer 126.9: 2012-2024, dated 2010.
Gerner and Meyskens, "Polyamines and cancer: old molecules, new understanding," Nature Rev. Cancer, 4:781-92, dated 2004.
Gerner et al., "Combination chemoprevention for colon cancer targeting polyamine synthesis and inflammation," Clinical Cancer Research, 15(3):758-761, dated 2009.
Singh et al., "Bifidobacterium longum, a lactic acid-producing intestinal bacterium inhibits colon cancer and modulates the intermediate biomarkers of colon carcinogenesis," Carcinogenesis, 18:833-841, dated 1997.
Singh et al., "Modulation of azoxymethane-induced mutational activation of ras protooncogenes by chemopreventive agents in colon carcinogenesis," Carcinogenesis, (15):1317-1323, dated 1994.
Smithson et al., "Discovery of potent and selective inhibitors of Trypanosoma brucei ornithine decarboxylase," The Journal of Biological Chemistry, 265(22):16771-16781, dated 2010.
Soda et al., "Polyamine-rich food decreases age-associated pathology and mortality in aged mice," Experimental Gerontology, 44: 727-732, dated 2009.
Su et al., "Multiple intestinal neoplasia caused by a mutation in the murine homolog of the APC gene," Science, (256):668-670, dated 1992.
Tabib et al., "Role of polyamines in mediating malignant transformation and oncogene expression," Int. J. Biochem. Cell. Biol., 31:1289-1295, dated 1999.
Tempero et al., "Chemoprevention of mouse colon tumors with difluoromethylornithine during and after carcinogen treatment," Cancer Res., 49(21):5793-7, dated 1989.
Third Party Observation, submitted in International Application No. PCT/US2016/017751, dated May 16, 2017.
Thomas and Thomas, "Polyamine metabolism and cancer," J. Cell Mol. Med., 7:113-26, dated 2003.
Thompson et al., "Inhibition of mammary carcinogenesis by sulfone metabolite of sulindac," J. Natl. Cancer Inst., (87):125-1260, dated 1995.

(56) References Cited

OTHER PUBLICATIONS

Thompson et al., "Levels of rectal mucosal polyamines and prostaglandin E2 predict ability of DFMO and sulindac to prevent colorectal adenoma," Gastroenterology, 139(3): 797-805, dated 2010.

Thompson, et al., "Sulfone metabolite of sulindac inhibits mammary carcinogenesis," Cancer Research, 57:267-271, dated 1997.

Vane and Botting, "Mechanism of action of anti-inflammatory drugs," Scand. J. Rheumatol., 25(Suppl. 102):9-21, dated 1996.

Vargas et al., "Dietary Polyamine intake and polyamines measured in urine," Nutrition and Cancer, 66(7): 1144-1153, dated 2014.

Visvanathan et al., "Association among an ornithine decarboxylase polymorphism, androgen receptor gene (CAG) repeat length and prostate cancer risk," J. Urol., 171(2 Pt 1): 652-5, dated 2004.

Wallace and Caslake, "Polyamines and colon cancer," Eur J Gastroenterol Helatol., 13(9): 1033-1039, dated 2001.

Wallace, "The physiological role of the polyamines," Eur. J. Clin. Invest., 30:1-3, dated 2000.

Wang et al., "Mucosal polyamine measurements and colorectal cancer risk," J. Cell. Biochem., 63:252-257, dated 1996.

Yu, Alice L., et al. "Anti-GD2 antibody with GM-CSF, interleukin-2, and isotretinoin for neuroblastoma." New England Journal of Medicine 363.14: 1324-1334, dated 2010.

Zell et al., "Associations of a polymorphism in the ornithine decarboxylase gene with colorectal cancer survival," Clin. Cancer Res., 15(19):6208-16, dated 2009.

Zell et al., "Ornithine decarboxylase (Odc)-1 gene polymorphism effects on baseline tissue polyamine levels and adenoma recurrence in a randomized phase III adenoma prevention trial of DFMO + sulindac versus placebo," J. Clin. Oncol., 26(15S):Abstract 1502, dated 2008.

Zell et al., "Ornithine decarboxylase-1 polymorphism, chemoprevention with eflornithine and sulindac, and outcomes among colorectal adenoma patients," J. Natl. Cancer Inst., 102:1513-1516, dated 2010.

Zell et al., "Risk and risk reduction involving arginine intake and meat consumption in colorectal tumorigenesis and survival," Intl. J. Cancer, 120:459-68, dated 2007.

Zell et al., "Risk of cardiovascular events in a randomized placebo-controlled, double-blind trial of difluoromethylornithine plus sulindac for the prevention of sporadic colorectal adenomas," Cancer Prev. Res., 2(3):209-12, dated 2009.

Zell et al., "Survival after colorectal cancer diagnosis is associated with colorectal cancer family history," Cancer Epidemiol. Biomarkers Prev., 17:3134-40, dated 2008.

Zeng, G. X., et al. "New concept and clinical application of colorectal intraepithelial neoplasia and carcinoma." Zhonghua wai ke za zhi [Chinese Journal of Surgery] 45.7: 449-451, dated 2007.

Ziogas and Anton-Culver, "Validation of family history data in cancer family registries," Am. J. Prev. Med., 24:190-8, dated 2003.

Zoumas-Morse et al., "Development of a polyamine database for assessing dietary intake," J. Am. Diet. Assoc., 107:1024-1027, dated 2007.

Office Communication issued in Japanese Patent Application No. 2017-560893, mailed Dec. 2, 2019, dated Dec. 2, 2019.

Jacob, Jeffrey, United States Securities and Exchange Commission, Cancer Prevention Pharamaceuticals, Inc., 215 pages, dated 2015.

Yu, Alice L., et al., Anti-GD2 Antibody with GM-CSF, Interleukin-2, and Isotretinoin for Neuroblastoma, N Engl J Med., 363(14): 1324-1334, 18 pages, dated Sep. 30, 2010.

Simon, Thorsten, et al., Long Term Outcome of High-Risk Neuroblastoma Patients After Immunotherapy with Antibody Ch14. 18 or oral Metronomic Chemotherapy, BMC Cancer 2011, 8 pages, dated 2011.

Matthay, Katherine K., Treatment of High-Risk Neuroblastoma with Intensive Chemotherapy, Radiotherapy, Autologous Bone Marrow Transplantation, and 13-CIS-Retinoic Acid, The New England Journal of Medicine, vol. 341, No. 16, 9 pages, dated Oct. 14, 1999.

Smith, Valeria et al., High-Risk Neuroblastoma Treatment Review, Children MDPI Journal, 7 pages, dated Aug. 28, 2018.

Monclair, Tom et al., The International Neuroblastoma Risk Group (INRG) Staging System: An INRG Task Force Report, Journal of Clinical Oncology, vol. 27, No. 2, 6 pages, dated Jan. 10, 2009.

Cohn, Susan L., et al., The International Neuroblastoma Risk Group (INRG) Classification System: An INRG Task Force Report, Journal of Clinical Oncology, vol. 27, No. 2, 9 pages, dated Jan. 10, 2009.

Sholler, Giselle L. Saulnier, et al., A Phase I Trial of DFMO Targeting Polyamine Addiction in Patients with Relapsed/Refractory Neuroblastoma, Supplemental S1 Table Enrollment Characteristics and Previous Relapse Therapies prior to Enrollment, https://doi.org/10.1371/journal.pone.0127246.s002, 16 pages, dated May 27, 2015.

Oesterheld, Javier, et al., Eflornithine as Postimmunotherapy Maintenance in High-Rish Neuroblastoma: Externally Controlled, Propensity Score-Matched Survival Outcome Comparisons, ASCO Journal of Clinical Oncology, 14 pages, dated Oct. 26, 2023.

Simoneau, Anne R., et al., The Effect of Difluoromethylornithine on Decreasing Prostate Size and Polyamines in Men: Results of a Year-Long Phase IIb Randomized Placebo-Controlled Chemoprevention Trial, Cancer Epidemiol Biomarkers, 16 pages, dated Feb. 17, 2008.

Meyskens, Frank L., et al., Effect of a-Difluoromethylornithine on Rectal Mucosal Levels of Polyamines in a Randomized, Double-Blinded Trial for Colon Cancer Prevention, Journal of the National Cancer Institute, vol. 90, No. 16, 8 pages, dated Aug. 19, 1998.

Meyskens, Frank L. Jr., et al., Difluoromethylornithine Plus Sulindac for the Prevention of Sporadic Colorectal Adenomas: A Randomized Placebo-Controlled, Double-Blind Trial, Cancer Prev Res, 14 pages, dated Jun. 1, 2008.

Carbone, Paul P., Phase I Chemoprevention Study of Difluoromethylornithine in Subjects with Organ Transplants, Cancer Epidemiology, Biomarkers & Prevention, vol. 10, 657-661, dated Jun. 2001.

Sinicrope, Frank A., et al., "Evaluation of Difluoromethylornithine for the Chemoprevention of Barrett's Esophagus and Mucosal Dysplasia," American Associated for Cancer Research, 11 pages, dated Jun. 2011.

Yu, Alice L., et al., Anti-GD2 Antibody with GM-CSF, Interleukin-2, and Isotretinoin for Neuroblastoma, The New England Journal of Medicine, 11 pages, dated Sep. 30, 2010.

Thomas, David W., Clinical Development Success Rates 2006-2015, 28 pages, dated 2016.

Lewis, Elizabeth C., et al., A subset analysis of a phase II trial evaluating the use of DFMO as maintenance therapy for high-risk neuroblastoma, Int. J. Cancer, 3152-3159, dated Apr. 23, 2020.

Sandler, Robert S., et al., Rectal Mucosal Ornithine Decarboxylase Activity is Not a Useful Marker of Risk for Colorectal Neoplasia, Digestive Diseases and Sciences, vol. 37, No. 11, pp. 1718-1724, dated Nov. 1992.

Desai, Tusar K., et al., Failure of Rectal Ornithine Decarboxylase to Identify Adenomatous Polyp Status, American Gastroenterological Association, pp. 1562-1567, dated Nov. 1992.

Abeloff, Martin D., et al., Phase II Trials of a-Difluoromethylornithine, an Inhibitor of Polyamine Synthesis in Advanced Small Cell Lung Cancer and Colon Cancer, Cancer Treatment Reports, vol. 70, No. 7, 3 pages, dated Jul. 1986.

Prados, Michael D., et al., Phase III Trial of Accelerated Hyperfractionation With or Without Difluromethylornithine (DFMO) Versus Standard Fractionated Radiotherapy With or Without DFMO for Newly Diagnosed Patients With Glioblastoma Multiforme, Int. J. Radiation Oncology Biol. Phys., vol. 49, No. 1, pp. 71-77, dated Sep. 25, 2000.

Fabian, Carol J., et al., A Phase II Breast Cancer Chemoprevention Trial of Oral-Difluoromethylornithine: Breast Tissue, Imaging, and Serum and Urine Biomarkers, Clinical Cancer Research, vol. 8, 3105-2117, dated Oct. 2002.

Vlastos, Anne-Therese, et al., Results of a Phase II Double-Blinded Randomized Clinical Trial of Difluoromethylornithine for Cervical Intraepithelial Neoplasia Grades 2 to 3, Clinical Cancer Research, vol. 11, 390-396, dated Jan. 1, 2005.

(56) References Cited

OTHER PUBLICATIONS

Malki, Ahmed, et al., Molecular Mechanisms of Colon Cancer Progression and Metastasis: Recent Insights and Advancements, International Journal of Molecular Sciences, 24 pages, dated Dec. 24, 2020.

Messing, Edward, et al., Randomized Prospective Phase III Trial of Difluoromethylornithine vs Placebo in Preventing Recurrence of Completely Resected Low Risk Superficial Bladder Cancer, The Journal of Urology, vol. 176, 500-504, dated Aug. 2006.

Sholler, Giselle L Saulnier et al., Maintenance DFMO Increases Survival in High Risk Neuroblastoma, Scientific Reports, 10 pages, dated Sep. 27, 2018.

Pearson, Andrew, et al., High-dose rapid and standard induction chemotherapy for patients aged over 1 year with stage 4 neuroblastoma: a randomised trial, Lancet Oncol, vol. 9, 10 pages, dated Mar. 2008.

* cited by examiner

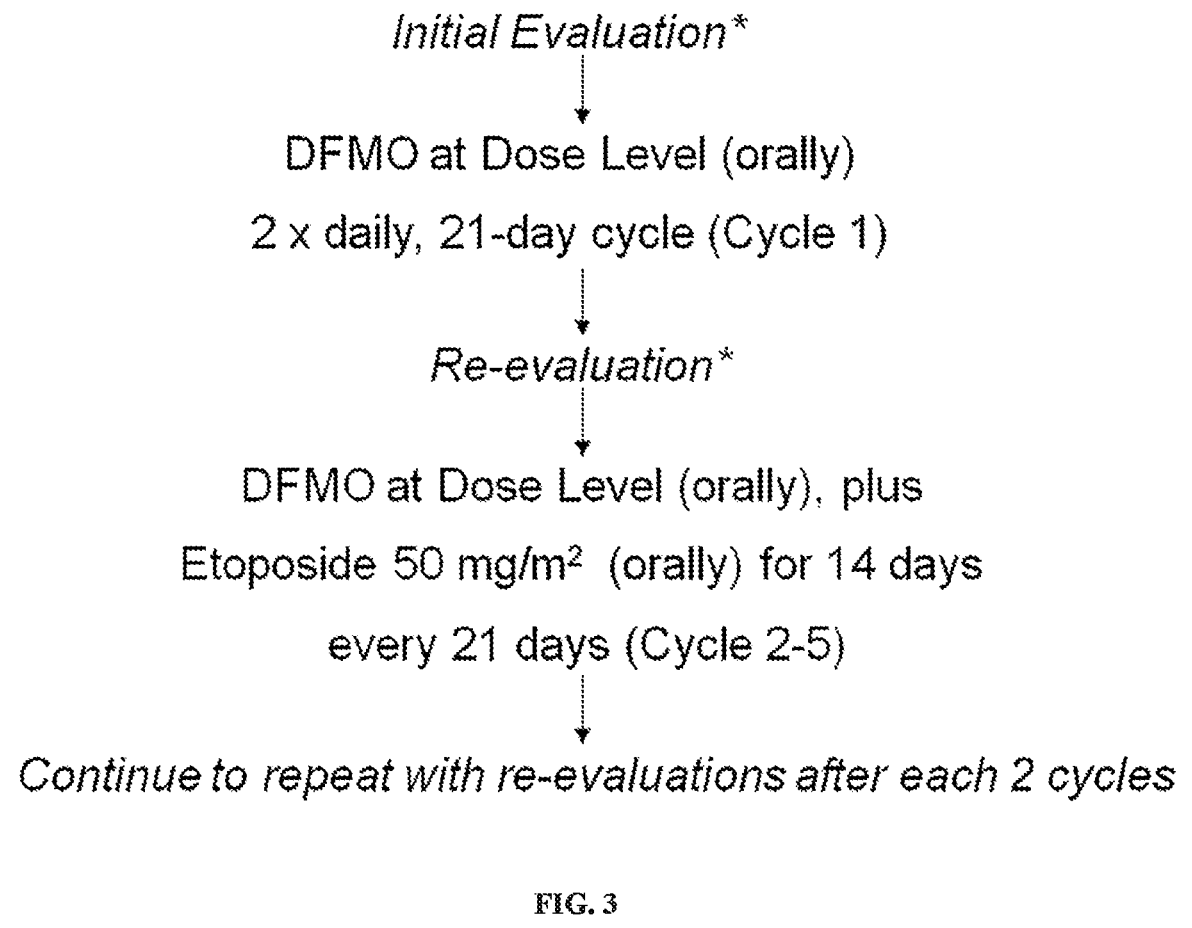

*Initial Evaluation**

↓

DFMO at Dose Level (orally)

2 x daily, 21-day cycle (Cycle 1)

↓

*Re-evaluation**

↓

DFMO at Dose Level (orally), plus

Etoposide 50 mg/m$^2$ (orally) for 14 days every 21 days (Cycle 2-5)

↓

*Continue to repeat with re-evaluations after each 2 cycles*

FIG. 3

METHODS FOR TREATING NEUROBLASTOMA

The present application is a continuation of U.S. application Ser. No. 18/230,601, filed Aug. 4, 2023, which is a continuation of U.S. application Ser. No. 17/147,697, filed Jan. 13, 2021, which is a continuation of U.S. application Ser. No. 15/550,595, filed Aug. 11, 2017, which is a national phase application under 35 U.S.C. § 371 of International Application No. PCT/US2016/017751, filed Feb. 12, 2016, which claims the priority benefit of U.S. provisional application No. 62/115,413, filed Feb. 12, 2015 and U.S. provisional application No. 62/154,804, filed Apr. 30, 2015, the entire contents of each of which are incorporated herein by reference.

The invention was made with government support under Grant Nos. R01 CA123065 and P50 CA095060 awarded by the National Institutes of Health. The government has certain rights in the invention.

BACKGROUND OF THE INVENTION

1. Field of the Invention

The present invention relates generally to the fields of cancer biology and medicine. More particularly, it concerns methods for the diagnosis, prevention, and treatment of carcinomas and risk factors thereof.

2. Description of Related Art

Neuroblastoma (NB) is a deadly childhood cancer that arises from neural crest cells of the sympathetic nervous system. The average age at diagnosis is 17 months and 50-60% of patients present with metastatic disease. NB is a heterogeneous disease, with varied risk groups (Maris, 2010). Up to 45% of patients are in a high-risk category that includes patients with MYCN amplification or other adverse clinicopathologic features. Despite advances in treatments that include chemotherapy, surgery, radiation, high dose chemotherapy with stem cell rescue, antibody-based therapy, and biologic-based therapy, the overall long-term survival of patients with high risk disease remains poor at approximately 50%. Approximately 20% of patients in this high-risk group fail to respond adequately to chemotherapy and develop progressive or refractory disease. Those which complete upfront therapy will have a >35% risk of relapse (Park et al., 2013; Yu et al., 2010; Modak et al., 2010).

Immunotherapy with antibodies directed against the cell surface expressed GD2 ganglioside, following induction and consolidation therapies, is associated with increased event free and overall survival in children with high-risk neuroblastoma (Yu et al., 2010). Anti-GD2 immunotherapy, however, is associated with intense visceral pain and pain in response to touch (allodynia) (Cheung et al., 1987; Wallace et al., 1997). Reducing immunotherapy-associated pain is a major unmet medical need in the treatment of patients with high-risk neuroblastoma. As such, new therapies for patients, especially those with relapsed or refractory NB, are needed.

SUMMARY OF THE INVENTION

In accordance with the present invention, there are provided methods for the preventative or curative treatment of neuroblastoma in a patient in need thereof comprising administering to the patient an effective amount of a pharmaceutical therapy comprising α-difluoromethylornithine (DFMO). In some embodiments, the pharmaceutical therapy further comprises a second agent. In some embodiments, the second agent is a non-steroidal anti-inflammatory drug (NSAID), a polyamine transporter inhibitor, an eIF-5a antagonist, a chemotherapeutic, or an immunomodulatory agent. In some embodiments, the non-aspirin containing NSAID is sulindac, celecoxib, or aspirin. In some embodiments, the NSAID is a non-aspirin containing NSAID. In some embodiments, the polyamine transporter inhibitor is AMTX1501. In some embodiments, the eIF-5a antagonist is GC7 or a proteasome inhibitor. In some embodiments, the proteasome inhibitor is bortezomib. In some embodiments, the chemotherapeutic is etoposide, cyclophosphamide, topotecan, a PI3K inhibitor, or an aurora kinase inhibitor. In some embodiments, the immunomodulatory agent is a GD2 antibody, a GD2 vaccine, GM-CSF, IL-2, or a retinoid. In some embodiments, the retinoid is isotretinoin.

In accordance with the present invention, there are provided methods for the preventative or curative treatment of neuroblastoma in a patient comprising, (a) obtaining results from a test that determines the patient's genotype at position +263 of at least one ODC1 allele; and (b) if the results indicate that the patient's genotype at position +263 of at least one allele of the ODC1 gene is T, administering to the patient an effective amount of a pharmaceutical therapy comprising α-difluoromethylornithine (DFMO). In some embodiments, the methods may be used to prevent the formation of new neuroblastomas within the patient.

In some embodiments, the results obtained in step (a) are obtained by receiving a report containing said genotype or taking a patient history that reveals the results. In some embodiments, step (a) comprises testing the patient's genotype at position +263 of at least one ODC1 allele. In some embodiments, the test determines the nucleotide base at position +263 of one allele of the ODC1 gene in the patient. In some embodiments, the test determines the nucleotide bases at position +263 of both alleles of the ODC1 gene in the patient. In some embodiments, the results indicate that the patient's genotype at position +263 of both alleles of the ODC1 gene is TT. In some embodiments, the results indicate that the patient's genotype at position +263 of both alleles of the ODC1 gene is TG.

In some embodiments, the methods further comprise obtaining results from a test that determines the patient's genotype at position +316 of at least one ODC1 allele and administering to the patient an effective amount of the pharmaceutical therapy if the results indicate that the patient's genotype at position +316 of at least one allele of the ODC1 gene is G. In certain embodiments, the methods may be used to prevent ototoxicity or the risk thereof within the patient.

In some embodiments, the methods further comprise obtaining results from a test that determines an expression level of an ODC1 gene product in a tumor sample obtained from the patient and administering to the patient an effective amount of the pharmaceutical therapy if the results indicate that the expression level of the ODC1 gene product in the tumor sample is elevated relative to a control sample (e.g., a non-tumor sample obtained from the patient or a sample obtained from a healthy patient).

In some embodiments, the methods further comprise increasing the dosage of the pharmaceutical therapy if the patient was already being treated with the pharmaceutical therapy, but at a lower dosage, prior to obtaining to the results of the test. In some embodiments, the pharmaceutical therapy further comprises a second agent. In some embodiments, the second agent is a non-steroidal anti-inflammatory drug (NSAID), a polyamine transporter inhibitor, an eIF-5a antagonist, a chemotherapeutic, or an immunomodulatory agent. In some embodiments, the non-aspirin containing NSAID is sulindac, celecoxib, or aspirin. In some embodiments, the NSAID is a non-aspirin containing NSAID. In some embodiments, the polyamine transporter inhibitor is AMTX1501. In some embodiments, the eIF-5a antagonist is GC7 or a proteasome inhibitor. In some embodiments, the proteasome inhibitor is bortezomib. In some embodiments, the chemotherapeutic is etoposide, cyclophosphamide, topotecan, a PI3K inhibitor, or an aurora kinase inhibitor. In some embodiments, the immunomodulatory agent is a GD2 antibody, a GD2 vaccine, GM-CSF, IL-2, or a retinoid. In some embodiments, the retinoid is isotretinoin.

In one aspect, there are provided methods for evaluating the suitability of a patient for preventative or curative treatment of neuroblastoma, comprising, (a) obtaining results from a test that determines the patient's genotype at position +263 of at least one ODC1 allele; and (b) if the results indicate that the patient's genotype at position +263 of at least one allele of the ODC1 gene is T, identifying the patient as suitable for treatment by a pharmaceutical therapy comprising an effective amount of α-difluoromethylornithine (DFMO). In some embodiments, the methods may be used to prevent the formation of new neuroblastomas within the patient.

In some embodiments, the results obtained in step (a) are obtained by receiving a report containing said genotype or taking a patient history that reveals the results. In some embodiments, step (a) comprises testing the patient's genotype at position +263 of at least one ODC1 allele. In some embodiments, the test determines the nucleotide base at position +263 of one allele of the ODC1 gene in the patient. In some embodiments, the test determines the nucleotide bases at position +263 of both alleles of the ODC1 gene in the patient. In some embodiments, the results indicate that the patient's genotype at position +263 of both alleles of the ODC1 gene is TT. In some embodiments, the results indicate that the patient's genotype at position +263 of both alleles of the ODC1 gene is TG.

In some embodiments, the methods further comprise obtaining results from a test that determines the patient's genotype at position +316 of at least one ODC1 allele and administering to the patient an effective amount of the pharmaceutical therapy if the results indicate that the patient's genotype at position +316 of at least one allele of the ODC1 gene is G. In certain embodiments, the methods may be used to prevent ototoxicity or the risk thereof within the patient.

In some embodiments, the methods further comprise obtaining results from a test that determines an expression level of an ODC1 gene product in a tumor sample obtained from the patient and administering to the patient an effective amount of the pharmaceutical therapy if the results indicate that the expression level of the ODC1 gene product in the tumor sample is elevated relative to a control sample (e.g., a non-tumor sample obtained from the patient or a sample obtained from a healthy patient).

In some embodiments, the methods further comprises increasing the dosage of the pharmaceutical therapy if the patient was already being treated with the pharmaceutical therapy, but at a lower dosage, prior to obtaining to the results of the test. In some embodiments, the pharmaceutical therapy further comprises a second agent. In some embodiments, the second agent is a non-steroidal anti-inflammatory drug (NSAID), a polyamine transporter inhibitor, an eIF-5a antagonist, a chemotherapeutic, or an immunomodulatory agent. In some embodiments, the non-aspirin containing NSAID is sulindac, celecoxib, or aspirin. In some embodiments, the NSAID is a non-aspirin containing NSAID. In some embodiments, the polyamine transporter inhibitor is AMTX1501. In some embodiments, the eIF-5a antagonist is GC7 or a proteasome inhibitor. In some embodiments, the proteasome inhibitor is bortezomib. In some embodiments, the chemotherapeutic is etoposide, cyclophosphamide, topotecan, a PI3K inhibitor, or an aurora kinase inhibitor. In some embodiments, the immunomodulatory agent is a GD2 antibody, a GD2 vaccine, GM-CSF, IL-2, or a retinoid. In some embodiments, the retinoid is isotretinoin.

In one aspect, there are provided methods for preventing the development or recurrence of a neuroblastoma in a patient at risk therefor comprising, (a) obtaining results from a test that determines the patient's genotype at position +263 of at least one ODC1 allele; and (b) administering to the patient an effective amount of α-difluoromethylornithine (DFMO) if the results indicate that the patient's genotype at position +263 of at least one allele of the ODC1 gene is T. In some embodiments, the methods may be used to prevent the formation of new neuroblastomas within the patient.

In some embodiments, the patient comprises cancer stem cells, a precancerous lesion with associated ODC hyperactivity, or a precancerous lesion and elevated cellular polyamine levels. In some embodiments, the patient has previously undergone at least one round of anti-cancer therapy. In some embodiments, the patient is in cancer remission.

In some embodiments, the results obtained in step (a) are obtained by receiving a report containing said genotype or taking a patient history that reveals the results. In some embodiments, step (a) comprises testing the patient's genotype at position +263 of at least one ODC1 allele. In some embodiments, the test determines the nucleotide base at position +263 of one allele of the ODC1 gene in the patient. In some embodiments, the test determines the nucleotide bases at position +263 of both alleles of the ODC1 gene in the patient. In some embodiments, the results indicate that the patient's genotype at position +263 of both alleles of the ODC1 gene is TT. In some embodiments, the results indicate that the patient's genotype at position +263 of both alleles of the ODC1 gene is TG.

In some embodiments, the methods further comprise obtaining results from a test that determines the patient's genotype at position +316 of at least one ODC1 allele and administering to the patient an effective amount of therapy if the results indicate that the patient's genotype at position +316 of at least one allele of the ODC1 gene is G. In certain embodiments, the methods may be used to prevent ototoxicity or the risk thereof within the patient.

In some embodiments, the methods further comprise obtaining results from a test that determines an expression level of an ODC1 gene product in a tumor sample obtained from the patient and administering to the patient an effective amount of the pharmaceutical therapy if the results indicate that the expression level of the ODC1 gene product in the tumor sample is elevated relative to a control sample (e.g., a non-tumor sample obtained from the patient or a sample obtained from a healthy patient).

In some embodiments, the methods further comprise increasing the dosage of the pharmaceutical therapy if the patient was already being treated with the pharmaceutical therapy, but at a lower dosage, prior to obtaining to the results of the test. In some embodiments, the pharmaceutical therapy further comprises a second agent. In some embodiments, the second agent is a non-steroidal anti-inflammatory drug (NSAID), a polyamine transporter inhibitor, an eIF-5a antagonist, a chemotherapeutic, or an immunomodulatory agent. In some embodiments, the non-aspirin containing NSAID is sulindac, celecoxib, or aspirin. In some embodiments, the NSAID is a non-aspirin containing NSAID. In some embodiments, the polyamine transporter inhibitor is AMTX1501. In some embodiments, the eIF-5a antagonist is GC7 or a proteasome inhibitor. In some embodiments, the proteasome inhibitor is bortezomib. In some embodiments, the chemotherapeutic is etoposide, cyclophosphamide, topotecan, a PI3K inhibitor, or an aurora kinase inhibitor. In some embodiments, the immunomodulatory agent is a GD2 antibody, a GD2 vaccine, GM-CSF, IL-2, or a retinoid. In some embodiments, the retinoid is isotretinoin.

In one aspect, there are provided methods for preventing the development or recurrence of a carcinoma in a patient at risk therefor comprising, (a) obtaining results from a test that determines the presence of cancer stem cells in a sample from the patient; and (b) administering to the patient an effective amount of α-difluoromethylornithine (DFMO) if the results indicate that the patient's sample comprises cancer stem cells. In some embodiments, the methods may be used to prevent the formation of new neuroblastomas within the patient.

In some embodiments, the presence of cancer stem cells is determined by detecting the presence of a cancer stem cell biomarker. In some embodiments, the patient has a metastatic cancer. In some embodiments, the patient has previously undergone at least one round of anti-cancer therapy. In some embodiments, the patient is in cancer remission.

In some embodiments, the carcinoma is colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, or glioblastoma.

In some embodiments, the patient comprises a precancerous lesion associated with ODC hyperactivity. In some embodiments, the patient comprises a precancerous lesion and elevated cellular polyamine levels.

In some embodiments, the results obtained in step (a) are obtained by receiving a report containing said genotype or taking a patient history that reveals the results. In some embodiments, step (a) comprises testing the patient's genotype at position +263 of at least one ODC1 allele. In some embodiments, the test determines the nucleotide base at position +263 of one allele of the ODC1 gene in the patient. In some embodiments, the test determines the nucleotide bases at position +263 of both alleles of the ODC1 gene in the patient. In some embodiments, the results indicate that the patient's genotype at position +263 of both alleles of the ODC1 gene is TT. In some embodiments, the results indicate that the patient's genotype at position +263 of both alleles of the ODC1 gene is TG.

In some embodiments, the methods further comprise obtaining results from a test that determines the patient's genotype at position +316 of at least one ODC1 allele and administering to the patient an effective amount of the pharmaceutical therapy if the results indicate that the patient's genotype at position +316 of at least one allele of the ODC1 gene is G. In certain embodiments, the methods may be used to prevent ototoxicity or the risk thereof within the patient.

In some embodiments, the methods further comprise obtaining results from a test that determines an expression level of an ODC1 gene product in a tumor sample obtained from the patient and administering to the patient an effective amount of the pharmaceutical therapy if the results indicate that the expression level of the ODC1 gene product in the tumor sample is elevated relative to a control sample (e.g., a non-tumor sample obtained from the patient or a sample obtained from a healthy patient).

In some embodiments, the methods further comprise increasing the dosage of the pharmaceutical therapy if the patient was already being treated with the pharmaceutical therapy, but at a lower dosage, prior to obtaining to the results of the test. In some embodiments, the pharmaceutical therapy further comprises a second agent. In some embodiments, the second agent is a non-steroidal anti-inflammatory drug (NSAID), a polyamine transporter inhibitor, an eIF-5a antagonist, a chemotherapeutic, or an immunomodulatory agent. In some embodiments, the non-aspirin containing NSAID is sulindac, celecoxib, or aspirin. In some embodiments, the NSAID is a non-aspirin containing NSAID. In some embodiments, the polyamine transporter inhibitor is AMTX1501. In some embodiments, the eIF-5a antagonist is GC7 or a proteasome inhibitor. In some embodiments, the proteasome inhibitor is bortezomib. In some embodiments, the chemotherapeutic is etoposide, cyclophosphamide, topotecan, a PI3K inhibitor, or an aurora kinase inhibitor. In some embodiments, the immunomodulatory agent is a GD2 antibody, a GD2 vaccine, GM-CSF, IL-2, or a retinoid. In some embodiments, the retinoid is isotretinoin.

In one aspect, there are provided methods for predicting the efficacy of DFMO therapy comprising assessing a urinary polyamine level in a patient to be treated with DFMO, wherein a high urinary polyamine level predicts improved efficacy for DFMO therapy. In some embodiments, the patient has cancer, such as, for example, colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, or glioblastoma. In some embodiments, a high urinary polyamine level is a level that is at least twice the level found in healthy control subjects.

In one aspect, there are provided methods for the preventative or curative treatment of neuroblastoma in a patient comprising administering to the patient effective amounts of a pharmaceutical therapy comprising an anti-GD2 therapy and a first agent that inhibits ornithine decarboxylase (ODC) within the patient. In some embodiments, the anti-GD2 therapy comprises a GD2 antibody and/or a GD2 vaccine. In some embodiments, the methods reduce the risk of allodynia within the patient compared with methods that administer to the patient an effective amount of a pharmaceutical therapy comprising an anti-GD2 therapy without an agent that inhibits ornithine decarboxylase (ODC) within the patient. In some embodiments, the first agent is alpha-difluoromethylornithine (DFMO). In some embodiments, the DFMO is administered to the patient at least about 6 hours, 12 hours, 24 hours, 36 hours, 48 hours, 3 days, 4 days, 5 days, 6 days, 1 week, 2 weeks, 3 weeks, 1 month, 2 months, or 3 months after the administration of the anti-GD2 therapy. In some embodiments, the DFMO is administered to the patient at least about 6 hours, 12 hours, 24 hours, 36 hours, 48 hours, 3 days, 4 days, 5 days, 6 days, 1 week, 2 weeks, 3 weeks, 1 month, 2 months, or 3 months before the administration of the anti-GD2 therapy. In some embodiments, the methods further comprise administering a second agent that modulates the polyamine pathway to reduce overall polyamine content within the patient when combined with the agent that inhibits ornithine decarboxylase (ODC) within the patient. In some embodiments, the second agent that modulates the polyamine pathway to reduce overall polyamine content within the patient is a non-steroidal anti-inflammatory drug (NSAID), such as, for example, aspirin, sulindac, or celecoxib. In some embodiments, the patient has previously undergone at least one round of anti-cancer therapy. In some embodiments, the patient is in cancer remission.

In some embodiments, the methods further comprise obtaining results from a test that determines that patient's genotype at position +316 of at least one ODC1 allele promoter and administering to the patient effective amounts of the pharmaceutical therapy if the results indicate that the patient's genotype at position +316 of at least one ODC1 allele promoter is G. In some embodiments, the results are obtained by receiving a report containing said genotype or taking a patient history that reveals the results. In some embodiments, the methods comprise testing the patient's genotype at position +316 of at least one ODC1 allele. In some embodiments, the test determines the nucleotide base at position +316 of one allele of the ODC1 gene in the patient. In some embodiments, the test determines the nucleotide bases at position +316 of both alleles of the ODC1 gene in the patient. In some embodiments, the results indicate that the patient's genotype at position +316 of both alleles of the ODC1 gene is GG. In some embodiments, the results indicate that the patient's genotype at position +316 of both alleles of the ODC1 gene is GA. In certain embodiments, the methods may be used to prevent ototoxicity or the risk thereof within the patient.

In some embodiments, the methods further comprise obtaining results from a test that determines that patient's genotype at position +263 of at least one ODC1 allele promoter and administering to the patient effective amounts of the pharmaceutical therapy if the results indicate that the patient's genotype at position +263 of at least one ODC1 allele promoter is T. In some embodiments, the results are obtained by receiving a report containing said genotype or taking a patient history that reveals the results. In some embodiments, the results are obtaining by testing the patient's genotype at position +263 of at least one ODC1 allele. In some embodiments, the methods comprise testing the patient's genotype at position +263 of at least one ODC1 allele. In some embodiments, the test determines the nucleotide base at position +263 of one allele of the ODC1 gene in the patient. In some embodiments, the test determines the nucleotide bases at position +263 of both alleles of the ODC1 gene in the patient. In some embodiments, the results indicate that the patient's genotype at position +263 of both alleles of the ODC1 gene is TT. In some embodiments, the results indicate that the patient's genotype at position +263 of both alleles of the ODC1 gene is TG.

In variations on any of the above embodiments, DFMO is administered systemically. In some embodiments, DFMO and a second agent are administered by distinct routes. In some embodiments, the DFMO or the second agent are administered orally, intraarterially or intravenously. In some embodiments, the DFMO is administered orally. In some embodiments, the effective amount of DFMO is 500 mg/day. In some embodiments, the DFMO is administered intravenously. In some embodiments, the effective amount of DFMO is from about 0.05 to about 5.0 g/m²/day. In some embodiments, the DFMO and the second agent are formulated for oral administration. In some embodiments, the DFMO is formulated for pediatric administration, such as an oral liquid, an oral powder, a coated tablet, or a chewable tablet. In some embodiments, the DFMO or the second agent is formulated as a hard or soft capsule or a tablet. In some embodiments, the DFMO is administered every 12 hours. In some embodiments, the DFMO is administered every 24 hours. In some embodiment, DFMO is administered before the second agent. In some embodiments, the DFMO is administered at least about 6 hours, 12 hours, 24 hours, 36 hours, 48 hours, 3 days, 4 days, 5 days, 6 days, 1 week, 2 weeks, 3 weeks, 1 month, 2 months, or 3 months before the administration of the second agent. In some embodiments, DFMO is administered after the second agent. In some embodiments, the DFMO is administered at least about 6 hours, 12 hours, 24 hours, 36 hours, 48 hours, 3 days, 4 days, 5 days, 6 days, 1 week, 2 weeks, 3 weeks, 1 month, 2 months, or 3 months after the administration of the second agent. In some embodiments, DFMO is administered before and after the second agent. In some embodiments, DFMO is administered concurrently with the second agent. In some embodiments, DFMO is administered at least a second time. In some embodiments, the second agent is administered at least a second time.

In variations on any of the above embodiments, the patient has a solid tumor, and said method may further comprise resection of said solid tumor. In some embodiments, DFMO and the second agent are administered prior to said resection. In some embodiments, DFMO and the second agent are administered after said resection.

In variations on any of the above embodiments, the carcinoma is colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, or glioblastoma.

In variations on any of the above embodiments, the patient is human patient. In some embodiments, the human patient is a pediatric patient.

In variations on any of the above embodiments, the DEMO is eflornithine hydrochloride monohydrate, including, for example, a racemic mixture of its two enantiomers.

In variations on any of the above embodiments, the NSAID is a metabolite of sulindac.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3. Design of NMTRC 002-Safety Study for Refractory or Relapsed Neuroblastoma with DFMO Alone and in Combination with Etoposide. *Evaluation includes: 1. Response evaluation: CT, MIBG, VMA, Bone Marrow; 2. Biological evaluation: Tumor cells isolated from bone marrow were evaluated for MYCN status. Spot urine samples were tested for polyamine levels. DFMO dose escalation: Level 1=500 mg/m² BID, Level 2=750 mg/m² BID, Level 3=1000 mg/m² BID, Level 4=1500 mg/m² BID.

FIG. 6A. EFS and OS for All Patients. FIG. 6B. EFS for patients enrolled previously on ANBL0032 (top solid line) compared to the ANBL0032 Trial results (bottom solid line). FIG. 6C. OS for patients enrolled previously on ANBL0032 compared to the ANBL0032 Trial results.

DESCRIPTION OF ILLUSTRATIVE EMBODIMENTS

Figure 1:
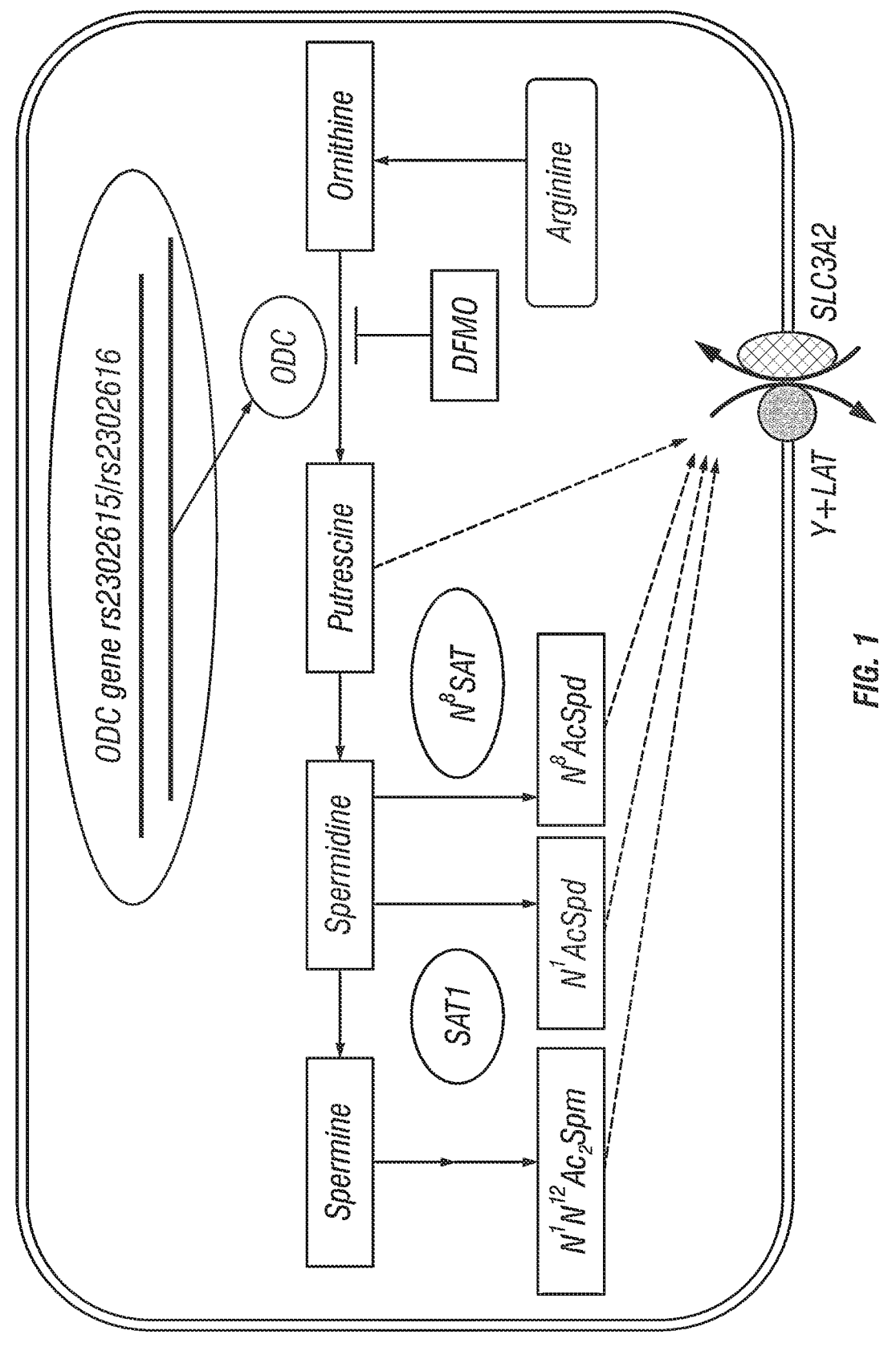
FIG. 1. Genetic and metabolic markers of DFMO efficacy in neuroblastoma. ODC transcription is influenced by specific genetic variability, including the SNPs rs2302615 (Martinez et al., 2003; Zell et al., 2009) and rs2302616 (Garcia-Huidobro et al., 2014a). The DFMO target, ODC, decarboxylates ornithine to form the diamine putrescine, which is then metabolized into longer chain amines. Spermidine is a substrate for two acetyltransferases that monoacetylate this amine at either the $N^1$ or $N^8$ positions. Spermine is a substrate for one of these transferases (SAT1), which diacetylates this amine. Putrescine, the monoacetyl-spermidines ($N^1AcSpd/N^8AcSpd$) and diacetylspermine ($N^1N^{12}Ac_2Spm/DAS$) are all substrates for the solute carrier transporter SLC3A2/Y+LAT, which exports these amines.

High risk neuroblastoma (NB) remains a challenge in pediatric oncology, accounting for 15% of all pediatric cancer deaths. While most patients are able to attain remission, approximately 50% will relapse. Once relapsed, there is currently no curative treatment for these children, and for these children the 5-year survival rate is <10%. As such, new therapeutic approaches are needed to treat these children. Relapsed patients who are able to obtain a second remission are not eligible for relapse therapeutic trials since they have no evidence of disease and yet they are likely to relapse within 6 months to one year. Prevention of relapse is one such approach to improve outcome in these patients. The therapeutic methods provided herein address this concept, while using, in some embodiments, a well-tolerated targeted medication for children in remission.

Reported herein is the first clinical study of an oral dosing form of DFMO in any pediatric population. It was found that DFMO doses of 500-1500 mg/m² administered twice per day by mouth are well tolerated by pediatric patients. The results of this trial corroborate the safety of this agent noted in cancer chemoprevention studies in adults, where oral DFMO doses were 250-500 mg/m² daily and ranged from 3-4 years in treatment duration (Meyskens et al., 2008; Bailey et al., 2010). Doses used in this trial, similar to adult dosing, were chosen to attain biological activity as shown by the decrease in urinary polyamines and responses seen.

Children with the minor T allele at rs2302616 of the ODC gene with relapsed or refractory NB were found to have higher levels of urinary polyamine markers and responded better to therapy containing DFMO, compared to those with the major G allele at this locus. In some embodiments, this patient subset displays dependence on polyamines and is well suited to benefit from therapies targeting this pathway. Furthermore, immunotherapy with antibodies directed against the cell surface expressed GD2 ganglioside, following induction and consolidation therapies, has been found to be associated with increased event free and overall survival in children with high-risk neuroblastoma (Yu et al., 2010). However, anti-GD2 immunotherapy is associated with intense visceral pain and pain in response to touch (allodynia) (Cheung et al., 1987; Wallace et al., 1997). Silva et al. (2011) have reported that allodynia and edema induced by Freund's adjuvant injection in paws of rats induces expression and activity of ODC1, that injection of putrescine or other polyamines induced allodynia and edema in the absence of other stimuli, and that DFMO (at doses of 10 μmol per paw) suppressed allodynia and edema induced by adjuvant in an animal model of inflammation-induced pain. Thus, as shown in Example 6, methods for the preventative or curative treatment of neuroblastoma in a patient may comprise administering to the patient effective amounts of a pharmaceutical therapy comprising an anti-GD2 therapy and DFMO.

I. POLYAMINES IN CANCER AND DEMO

The identification of novel inhibitors of enzymes involved in polyamine biosynthesis with antitumor activities has recently revived interest in polyamine homeostasis and in designing strategies of cancer chemotherapy (Mamont et al., 1978; Porter et al., 1992; Seiler et al., 1998). Selective pharmacological interference of polyamine synthesis results in tumor cell growth inhibition under both in vitro and in vivo conditions (Mamont et al., 1978; McCann and Pegg, 1992). Furthermore, the dramatic increases in the activity of ODC in certain tumor cells have been linked to G1-S transition (Fuller et al., 1977; Kahana and Nathans, 1984; Kaczmarek et al., 1987). Without being bound by theory, the molecular basis for this derives from the fact that ODC is among those genes that can be regulated by c-Myc and MYCN (Bello-Fernandez et al., 1993; Pena et al., 1993; Wagner et al., 1993; Lutz et al., 1996; Lu et al., 2003), both of which regulate entry into and exit from the cell cycle. Because cell growth is dependent on polyamines, interference with polyamine biosynthesis has been considered as a potentially promising therapeutic approach against proliferative diseases, including various malignancies (Heby and Persson, 1990; Auvinen et al., 1992; McCann and Pegg, 1992). α-Difluoromethylornithine (DFMO or eflornithine or 2-(difluoromethyl)-dl-ornithine), an enzyme-activated irreversible inhibitor of ODC (Metcalf et al., 1978; Poulin et al., 1992), has been the prototype tool for the study of therapeutic effectiveness of polyamine depletion in experimental tumors (McCann and Pegg, 1992; Meyskens and Gerner, 1999). DFMO is known to inhibit cell growth of many cancer cells and induce cell differentiation (Chapman, 1980; Melino et al., 1988). These processes are accompanied by an apparent depletion of putrescine (Put) and spermidine (Spd) pools (Pegg, 1988; Heby and Persson, 1990; McCann and Pegg, 1992). DFMO has also been shown to induce apoptosis and inhibit metastasis in a human gastric cancer model (Takahashi et al., 2000).

DFMO decreases APC-dependent intestinal tumorigenesis in mice (Erdman et al., 1999). Oral DFMO administered daily to humans inhibits ODC enzyme activity and polyamine contents in a number of epithelial tissues (Love et al., 1993; Gerner et al., 1994; Meyskens et al., 1994; Meyskens et al., 1998; Simoneau et al., 2001; Simoneau et al., 2008). DFMO, in combination with the non-steroidal anti-inflammatory drug (NSAID) sulindac, has been reported to markedly lower the adenoma recurrence rate among individuals with colonic adenomas when compared to placebo in a randomized clinical trial (Meyskens et al., 2008).

DFMO and its use in the treatment of benign prostatic hypertrophy are described in two patents, U.S. Pat. Nos. 4,413,141, and 4,330,559. U.S. Pat. No. 4,413,141 describes DFMO as being a powerful inhibitor of ODC, both in vitro and in vivo. Administration of DFMO causes a decrease in putrescine and spermidine concentrations in cells in which these polyamines are normally actively produced. Additionally, DFMO has been shown to be capable of slowing neoplastic cell proliferation when tested in standard tumor models. U.S. Pat. No. 4,330,559 describes the use of DFMO and DEMO derivatives for the treatment of benign prostatic hypertrophy. Benign prostatic hypertrophy, like many disease states characterized by rapid cell proliferation, is accompanied by abnormal elevation of polyamine concentrations.

Side effects observed with DFMO include effects on hearing at high doses of 4 $g/m^2$/day that resolve when it is discontinued. These effects on hearing are not observed at lower doses of 0.4 $g/m^2$/day when administered for up to one year (Meyskens et al., 1994). In addition, a few cases of dizziness/vertigo are seen that resolve when the drug is stopped. Thrombocytopenia has been reported predominantly in studies using high "therapeutic" doses of DFMO (>1.0 $g/m^2$/day) and primarily in cancer patients who had previously undergone chemotherapy or patients with compromised bone marrow. Although the toxicity associated with DFMO therapy are not, in general, as severe as other types of chemotherapy, in limited clinical trials it has been found to promote a dose-related thrombocytopenia. Moreover, studies in rats have shown that continuous infusion of DFMO for 12 days significantly reduces platelet counts compared with controls. Other investigations have made similar observations in which thrombocytopenia is the major toxicity of continuous i.v. DFMO therapy. These findings suggest that DFMO may significantly inhibit ODC activity of the bone marrow precursors of megakaryocytes. DFMO may inhibit proliferative repair processes, such as epithelial wound healing.

Hearing loss/change by audiometry testing has been reported in 8.4% of patients on high dose DFMO (4 $g/m^2$/day) that resolve when it is discontinued. Rash and alopecia have been reported in 3% of patients. Anorexia and abdominal pain have been reported in 2% of patients treated with DFMO. Rare but serious side effects, including dizziness (1%), headaches (2%), and seizures (8%), have been reported in patients on intravenous DFMO. Myelosuppression (including leukopenia, [37%], anemia [55%], and thrombocytopenia [14%]) have been reported at high intravenous doses, but do not usually occur at low dose (500 mg).

TABLE 1

| Toxicity for DFMO Potential Risk | | |
| --- | --- | --- |
| Likely | Less Likely | Rare |
| Happens to 10-30 patients out of every 100 | Happens to 3-10 patients out of every 100 | Happens to fewer than 3 patients out of every 100 |
| Fewer red and white blood cells | Nausea | Loss of appetite |
| | Hearing Loss | Abdominal Pain |
| a) a low number of red blood cells can make you feel tired and weak and may require transfusion. | Ringing in ears | Flatulence (gas) |
| | Diarrhea | Dizziness |
| | Headache | Skin Rash |
| | Weakness | Seizures |
| | | Sores in the mouth |
| b) a low number of white blood cells can make it easier to get infections | | Runny nose |
| | | Difficulty sleeping |
| | | Infections |
| Decrease in the number of platelets made in the bone marrow | | Dry mouth |
| | | Constipation |
| | | Dry skin |
| | | Menstrual disorders |
| | | Sore throat |
| | | Vomiting |
| | | Vasodilation (the relaxation of blood vessels possibly causing low blood pressure) |
| | | Emotional ups and downs |
| | | Itchiness |
| | | Body aches |
| | | Pain |

A phase III clinical trial assessed the recurrence of adenomatous polyps after treatment for 36 months with DFMO plus sulindac or matched placebos. Temporary hearing loss is a known toxicity of treatment with DFMO, thus a comprehensive approach was developed to analyze serial air conduction audiograms. The generalized estimating equation method estimated the mean difference between treatment arms with regard to change in air conduction pure tone thresholds while accounting for within-subject correlation due to repeated measurements at frequencies. Based on 290 subjects, there was an average difference of 0.50 dB between subjects treated with DFMO plus sulindac compared with those treated with placebo (95% confidence interval, −0.64 to 1.63 dB; P=0.39), adjusted for baseline values, age, and frequencies. In the normal speech range of 500 to 3,000 Hz, an estimated difference of 0.99 dB (−0.17 to 2.14 dB; P=0.09) was detected. Dose intensity did not add information to models. There were 14 of 151 (9.3%) in the DFMO plus sulindac group and 4 of 139 (2.9%) in the placebo group who experienced at least 15 dB hearing reduction from baseline in two or more consecutive frequencies across the entire range tested (P=0.02). Follow-up air conduction done at least six months after the end of treatment showed an adjusted mean difference in hearing thresholds of 1.08 dB (−0.81 to 2.96 dB; P=0.26) between treatment arms. There was no significant difference in the proportion of subjects in the DFMO plus sulindac group who experienced clinically significant hearing loss compared with the placebo group. The estimated attributable risk of ototoxicity from exposure to the drug was 8.4% (95% confidence interval, −2.0% to 18.8%; P=0.12). There was a <2 dB difference in mean threshold for patients treated with DFMO plus sulindac compared with those treated with placebo. The results of this study were discussed in greater detail in McLaren et al. (2008), which is incorporated herein by reference in its entirety.

II. EFLORNITHINE

The terms "eflornithine," "α difluoromethylornithine", and "DFMO" are synonymous. When any of these terms is used by itself and free of context refers to 2,5-diamino-2-(difluoromethyl) pentanoic acid in any of its forms, including non-salt and salt forms (e.g., eflornithine HCl), anhydrous and hydrate forms of non-salt and salt forms (e.g., eflornithine hydrochloride monohydrate), solvates of non-salt and salts forms, its enantiomers (R and S forms, which may also by identified as d and I forms), and mixtures of these enantiomers (e.g., racemic mixture). Specific forms of eflornithine include eflornithine hydrochloride monohydrate (i.e., CAS ID: 96020-91-6; MW: 236.65), eflornithine hydrochloride (i.e., CAS ID: 68278-23-9; MW: 218.63), and free eflornithine (i.e., CAS ID: 70052-12-9; MW: 182.17). Where necessary, the specific form of eflornithine has been further specified. In some embodiments, the eflornithine of the present disclosure is eflornithine hydrochloride monohydrate (i.e., CAS ID: 96020-91-6). The terms "eflornithine" and "DFMO" are used interchangeably herein. DFMO is an abbreviation for difluoromethylornithine. Other synonyms of eflornithine and DFMO include: α-difluoromethylornithine, 2-(difluoromethyl)-DL-ornithine, 2-(difluoromethyl)-dl-ornithine, 2-(Difluoromethyl) ornithine, DL-α-difluoromethylornithine, N-Difluoromethylornithine, αδ-diamino-α-(difluoromethyl) valeric acid, and 2,5-diamino-2-(difluoromethyl) pentanoic acid.

Eflornithine is an enzyme-activated irreversible inhibitor of ornithine decarboxylase (ODC), the rate limiting enzyme of the polyamine biosynthetic pathway. As a result of this inhibition of polyamine synthesis, the compound is effective in preventing cancer formation in many organ systems, inhibiting cancer growth, and reducing tumor size. It also has synergistic action with other antineoplastic agents.

Eflornithine has been shown to decrease APC-dependent intestinal tumorigenesis in mice (Erdman et al., 1999). Oral eflornithine administered daily to humans inhibits ODC enzyme activity and polyamine contents in a number of epithelial tissues (Love et al., 1993; Gerner et al., 1994; Meyskens et al., 1994; Meyskens et al., 1998; Simoneau et al., 2001; Simoneau et al., 2008). Eflornithine in combination with the non-steroidal anti-inflammatory drug (NSAID) sulindac, has been reported to markedly lower the adenoma recurrence rate among individuals with colonic adenomas when compared to placebos in a randomized clinical trial (Meyskens et al., 2008).

Eflornithine was originally synthesized by Centre de Recherche Merrell, Strasbourg. Current U.S. Food and Drug Administration (FDA) approvals include:
  a) African sleeping sickness. High dose systemic IV dosage form—not marketed (Sanofi/WHO)
  b) Hirsutis (androgen-induced excess hair growth) topical dosage form While no oral formulations of eflornithine have yet been approved by the FDA, topical and injectable forms have been approved. Vaniqa® is a cream, which contains 15% w/w eflornithine hydrochloride monohydrate, corresponding to 11.5% w/w anhydrous eflornithine (EU), respectively 13.9% w/w anhydrous eflornithine hydrochloride (U.S.), in a cream for topical administration. Ornidyl® is an eflornithine HCl solution suitable for injection or infusion. It is supplied in the strength of 200 mg eflornithine hydrochloride monohydrate per ml (20 g/100 mL).

Eflornithine and its use in the treatment of benign prostatic hypertrophy are described in U.S. Pat. Nos. 4,413,141, and 4,330,559. The '141 Patent describes eflornithine as being a powerful inhibitor of ODC, both in vitro and in vivo. Administration of eflornithine is reported to cause a decrease in putrescine and spermidine concentrations in cells in which these polyamines are normally actively produced. Additionally, eflornithine has been shown to be capable of slowing neoplastic cell proliferation when tested in standard tumor models. The '559 Patent describes the use of eflornithine and eflornithine derivatives for the treatment of benign prostatic hypertrophy. Benign prostatic hypertrophy, like many disease states characterized by rapid cell proliferation, is accompanied by abnormal elevation of polyamine concentrations.

Eflornithine can potentially be given continuously with significant anti-tumor effects. This drug is relatively non-toxic at low doses of 0.4 g/m²/day to humans while producing inhibition of putrescine synthesis in tumors. Studies in a rat-tumor model demonstrate that eflornithine infusion can produce a 90% decrease in tumor putrescine levels without suppressing peripheral platelet counts.

Side effects observed with eflornithine include effects on hearing at high doses of 4 g/M²/day that resolve when it is discontinued. These effects on hearing are not observed at lower doses of 0.4 g/M²/day when administered for up to one year (Meyskens et al., 1994). In addition a few cases of dizziness/vertigo are seen that resolve when the drug is stopped. Thrombocytopenia has been reported predominantly in studies using high "therapeutic" doses of eflornithine (>1.0 g/m²/day) and primarily in cancer patients who had previously undergone chemotherapy or patients with compromised bone marrow. Although the toxicity associated with eflornithine therapy are not, in general, as severe as other types of chemotherapy, in limited clinical trials it has been found to promote a dose-related thrombocytopenia. Moreover, studies in rats have shown that continuous infusion of eflornithine for 12 days significantly reduces platelet counts compared with controls. Other investigations have made similar observations in which thrombocytopenia is the major toxicity of continuous i.v. eflornithine therapy. These findings suggest that eflornithine may significantly inhibit ODC activity of the bone marrow precursors of megakaryocytes. Eflornithine may inhibit proliferative repair processes, such as epithelial wound healing.

A phase III clinical trial assessed the recurrence of adenomatous polyps after treatment for 36 months with DFMO plus sulindac or matched placebos. Temporary hearing loss is a known toxicity of treatment with DFMO, thus a comprehensive approach was developed to analyze serial air conduction audiograms. The generalized estimating equation method estimated the mean difference between treatment arms with regard to change in air conduction pure tone thresholds while accounting for within-subject correlation due to repeated measurements at frequencies. Based on 290 subjects, there was an average difference of 0.50 dB between subjects treated with DFMO plus sulindac compared with those treated with placebo (95% confidence interval, −0.64 to 1.63 dB; P=0.39), adjusted for baseline values, age, and frequencies. There is a <2 dB difference in mean threshold for patients treated with DFMO plus sulindac compared with those treated with placebo. The results of this study are discussed in greater detail in McLaren et al., 2008, which is incorporated herein by reference in its entirety. Provided herein are methods of producing and compositions of fixed dose combinations of eflornithine and sulindac.

III. NSAIDS

NSAIDs are anti-inflammatory agents that are not steroids. In addition to anti-inflammatory actions, they have analgesic, antipyretic, and platelet-inhibitory actions. They are used primarily in the treatment of chronic arthritic conditions and certain soft tissue disorders associated with pain and inflammation. They act by blocking the synthesis of prostaglandins by inhibiting cyclooxygenase, which converts arachidonic acid to cyclic endoperoxides, precursors of prostaglandins. Inhibition of prostaglandin synthesis accounts for their analgesic, antipyretic, and platelet-inhibitory actions; other mechanisms may contribute to their anti-inflammatory effects. Certain NSAIDs also may inhibit lipoxygenase enzymes or phospholipase C or may modulate T-cell function. (AMA Drug Evaluations Annual, 1814-5, 1994).

The nonsteroidal anti-inflammatory drugs (NSAIDs), including aspirin, ibuprofen, piroxicam (Reddy et al., 1990; Singh et al., 1994), indomethacin (Narisawa, 1981), and sulindac (Piazza et al., 1997; Rao et al., 1995), effectively inhibit colon carcinogenesis in the AOM-treated rat model. NSAIDs also inhibit the development of tumors harboring an activated Ki-ras (Singh and Reddy, 1995). NSAIDs appear to inhibit carcinogenesis via the induction of apoptosis in tumor cells (Bedi et al., 1995; Lupulescu, 1996; Piazza et al., 1995; Piazza et al., 1997b). A number of studies suggest that the chemopreventive properties of the NSAIDs, including the induction of apoptosis, is a function of their ability to inhibit prostaglandin synthesis (reviewed in DuBois et al., 1996; Lupulescu, 1996; Vane and Botting, 1997). Studies, however, indicate that NSAIDs may act through both prostaglandin-dependent and -independent mechanisms (Alberts et al., 1995; Piazza et al., 1997a; Thompson et al., 1995; Hanif, 1996). Sulindac sulfone, a metabolite of the NSAID sulindac, lacks COX-inhibitory activity yet induces apoptosis in tumor cells (Piazza et al., 1995; Piazza et al., 1997b) and inhibits tumor development in several rodent models of carcinogenesis (Thompson et al., 1995; Piazza et al., 1995, 1997a).

Several NSAIDs have been examined for their effects in human clinical trials. A phase IIa trial (one month) of ibuprofen was completed and even at the dose of 300 mg/day, a significant decrease in prostoglandin $E_2$ ($PGE_2$) levels in flat mucosa was seen. A dose of 300 mg of ibuprofen is very low (therapeutic doses range from 1200-3000 mg/day or more), and toxicity is unlikely to be seen, even over the long-term. However, in animal chemoprevention models, ibuprofen is less effective than other NSAIDs.

In some embodiments, the methods provided herein comprise administering pharmaceutically acceptable amounts of an NSAID, including for example, any of the NSAIDS discussed herein.

A. Aspirin

Aspirin, also known as acetylsalicylic acid, is a salicylate drug, often used as an analgesic to relieve minor aches and pains, as an antipyretic to reduce fever, and as an anti-inflammatory medication. Aspirin was first isolated by Felix Hoffmann, a chemist with the German company Bayer in 1897. Salicylic acid, the main metabolite of aspirin, is an integral part of human and animal metabolism. While in humans much of it is attributable to diet, a substantial part is synthesized endogenously. Today, aspirin is one of the most widely used medications in the world, with an estimated 40,000 tons of it being consumed each year. In countries where Aspirin is a registered trademark owned by Bayer, the generic term is acetylsalicylic acid (ASA).

Aspirin also has an antiplatelet effect by inhibiting the production of thromboxane, which under normal circumstances binds platelet molecules together to create a patch over damaged walls of blood vessels. Because the platelet patch can become too large and also block blood flow, locally and downstream, aspirin is also used long-term, at low doses, to help prevent heart attacks, strokes, and blood clot formation in people at high risk of developing blood clots. It has also been established that low doses of aspirin may be given immediately after a heart attack to reduce the risk of another heart attack or of the death of cardiac tissue. Aspirin may be effective at preventing certain types of cancer, particularly colorectal cancer.

The main undesirable side effects of aspirin taken by mouth are gastrointestinal ulcers, stomach bleeding, and tinnitus, especially in higher doses. In children and adolescents, aspirin is no longer indicated to control flu-like symptoms or the symptoms of chickenpox or other viral illnesses, because of the risk of Reye's syndrome.

Aspirin is part of a group of medications called nonsteroidal anti-inflammatory drugs (NSAIDs), but differs from most other NSAIDS in the mechanism of action. Though aspirin, and others in its group called the salicylates, have similar effects (antipyretic, anti-inflammatory, analgesic) to the other NSAIDs and inhibit the same enzyme cyclooxygenase, aspirin (but not the other salicylates) does so in an irreversible manner and, unlike others, affects more the COX-1 variant than the COX-2 variant of the enzyme.

B. Sulindac and its Major Metabolites, Sulidac Sulfone and Sulindac Sulfide

Sulindac is a nonsteroidal, anti-inflammatory indene derivative with the following designation; (Z)-5-fluoro-2-methyl-1-((4-(methylsulfinyl)phenyl)methylene)-1H- chemical indene-3-acetic acid (Physician's Desk Reference, 1999). Without being bound by theory, the sulfinyl moiety is converted in vivo by reversible reduction to a sulfide metabolite and by irreversible oxidation to a sulfone metabolite (exisulind). See U.S. Pat. No. 6,258,845, which is incorporated herein by reference in its entirety. Sulindac, which also inhibits Ki-ras activation, is metabolized to two different molecules which differ in their ability to inhibit COX, yet both are able to exert chemopreventive effects via the induction of apoptosis. Sulindac sulfone lacks COX-inhibitory activity, and most likely facilitates the induction of apoptosis in a manner independent of prostaglandin synthesis. Available evidence indicates that the sulfide derivative is at least one of the biologically active compounds. Based on this, sulindac may be considered a prodrug.

Sulindac (Clinoril®) is available, for example, as 150 mg and 200 mg tablets. The most common dosage for adults is 150 to 200 mg twice a day, with a maximal daily dose of 400 mg. After oral administration, about 90% of the drug is absorbed. Peak plasma levels are achieved in about 2 hours in fasting patients and 3 to 4 hours when administered with food. The mean half-life of sulindac is 7.8 hours: the mean half-life of the sulfide metabolite is 16.4 hours. U.S. Pat. Nos. 3,647,858 and 3,654,349 cover preparations of sulindac, both are incorporate by reference herein in their entireties.

Sulindac is indicated for the acute and long-term relief of signs and symptoms of osteoarthritis, rheumatoid arthritis, ankylosing spondylitis, acute gout, and acute painful shoulder. The analgesic and antiinflammatory effects exerted by sulindac (400 mg per day) are comparable to those achieved by aspirin (4 g per day), ibuprofen (1200 mg per day), indometacin (125 mg per day), and phenylbutazone (400 to 600 mg per day). Side effects of sulindac include mild gastrointestinal effects in nearly 20% of patients, with abdominal pain and nausea being the most frequent complaints. CNS side effects are seen in up to 10% of patients, with drowsiness, headache, and nervousness being those most frequently reported. Skin rash and pruritus occur in 5% of patients. Chronic treatment with sulindac can lead to serious gastrointestinal toxicity such as bleeding, ulceration, and perforation.

The potential use of sulindac for chemoprevention of cancers, and in particular colorectal polyps, has been well studied. Two recent U.S. Pat. Nos. 5,814,625 and 5,843,929, detail potential chemopreventive uses of sulindac in humans. Both patents are incorporated herein in their entireties. Doses of sulindac claimed in U.S. Pat. No. 5,814,625 range from 10 mg to 1500 mg per day, with preferred doses of 50 mg to 500 mg per day. However, at the higher doses, the biggest problem with the use of sulindac as a single agent in chemoprevention is its well-known toxicities and moderately high risk of intolerance. The elderly appear to be especially vulnerable, as the incidence of side effects is higher in those over the age of 60. It is noted that this age group is most likely to develop colorectal cancer, and therefore, most likely to benefit from chemoprevention. Sulindac has been shown to produce regression of adenomas in Familial Adenomatous Polyposis (FAP) patients (Muscat et al., 1994), although at least one study in sporadic adenomas has shown no such effect (Ladenheim et al., 1995). Sulindac and its sulfone metabolite exisulind have been tested and continue to be tested clinically for the prevention and treatment of several cancer types.

A combination therapy of DFMO and sulindac was shown to be effective in reducing adenomas in these mice. See U.S. Pat. No. 6,258,845, which is incorporated herein by reference in its entirety.

C. Piroxicam

Piroxicam is a non-steroidal anti-inflammatory agent that is well established in the treatment of rheumatoid arthritis and osteoarthritis with the following chemical designation: 4 hydroxy-2-methyl-N-2-pyridyl-2H-1,2-benzothiazine-3-carboxamide 1,1-dioxide. Its usefulness also has been demonstrated in the treatment of musculoskeletal disorders, dysmenorrhea, and postoperative pain. Its long half-life enables it to be administered once daily. The drug has been shown to be effective if administered rectally. Gastrointestinal complaints are the most frequently reported side effects.

Piroxicam has been shown to be effective chemoprevention agent in animal models (Pollard and Luckert, 1989; Reddy et al., 1987), although it demonstrated side effects in a recent IIb trial. A large meta-analysis of the side effects of the NSAIDs also indicates that piroxicam has more side effects than other NSAIDs (Lanza et al., 1995).

The combination of DFMO and piroxicam has been shown to have a synergistic chemopreventive effect in the AOM-treated rat model of colon carcinogenesis (Reddy et al., 1990), although DFMO exerted a greater suppressive effect than piroxicam on Ki-ras mutation and tumorigenesis when each agent was administered separately (Reddy et al., 1990). In one study, administration of DFMO or piroxicam to AOM-treated rats reduced the number of tumors harboring Ki-ras mutations from 90% to 36% and 25%, respectively (Singh et al., 1994). Both agents also reduced the amount of biochemically active p21 ras in existing tumors.

D. Celecoxib

Celecoxib is a non-steroidal anti-inflammatory agent that is well established in the treatment of osteoarthritis, rheumatoid arthritis, acute pain, ankylosing spondylitis, and to reduce the number of colon and rectal polyps in patients with FAP with the following chemical designation: 4-[5-(4-Methylphenyl)-3-(trifluoromethyl) pyrazol-1-yl]benzenesulfonamide. Celecoxib is marketed under the brand names Celebrex, Celebra, and Onsenal by Pfizer. Celecoxib is a selective COX-2 inhibitor. Side effects of celecoxib include a 30% increase in rates of heart and blood vessel disease. Additionally, the risk of gastrointestinal side effects are greater than 80%.

E. Combinations of NSAIDs

Combinations of various NSAIDs are also used for various purposes. By using lower doses of two or more NSAIDs, it is possible to reduce the side effects or toxicities associated with higher doses of individual NSAIDs. For example, in some embodiments, sulindac may be used together with celecoxib. In some embodiments, the one or both of the NSAIDS are selective COX-2 inhibitors. Examples of NSAIDS that back be used either alone or in combination include, but are not limited to, the following: ibuprofen, naproxen, fenoprofen, ketoprofen, flurbiprofen, oxaprozin, indomethacin, sulindac, etodolac, diclofenac, piroxicam, meloxicam, tenoxicam, droxicam, lornoxicam, isoxicam, mefenamic acid, meclofenamic acid, flufenamic acid, tolfenamic acid, celecoxib rofecoxib valdecoxib parecoxib, lumiracoxib, or etoricoxib.

IV. DIAGNOSIS AND TREATMENT OF PATIENTS

In some embodiments, the treatment methods may be supplemented with diagnostic methods to improve the efficacy and/or minimize the toxicity of the anti-cancer thera-pies comprising administration of the compositions pro-vided herein. Such methods are described, for example, in U.S. Pat. Nos. 8,329,636 and 9,121,852, U.S. Patent Publi-cation US20130217743 and PCT Patent Publication WO2014070767, which are all incorporated herein by ref-erence. For example, compositions and formulations of the present disclosure may be administered to a subject with a genotype at position +316 of at least one allele of the ODC1 gene promoter is G. In some embodiments, the genotype at position +316 of both alleles of the patient's ODC1 gene promoters may be GG. In some embodiments, the genotype at position +316 of both alleles of the patient's ODC1 gene promoters may be GA.

In addition, a statistically significant interaction was detected for ODC1 genotype and treatment in a full model for adenoma recurrence, such that the pattern of adenoma recurrence among placebo patients was: GG 50%, GA 35%, AA 29% versus eflornithine/sulindac patients: GG 11%, GA 14%, AA 57%. The adenoma-inhibitory effect of eflornithine and sulindac was greater among those with the major G homozygous ODC1 genotype, in contrast to prior reports showing decreased risk of recurrent adenoma among CRA patients receiving aspirin carrying at least one A allele (Martinez et al., 2003; Barry et al., 2006; Hubner et al., 2008). These results demonstrate that ODC1 A allele carriers differ in response to prolonged exposure with eflornithine and sulindac compared to GG genotype patients, with A allele carriers experiencing less benefit in terms of adenoma recurrence, and potential for elevated risk of developing ototoxicity, especially among the AA homozygotes.

In other aspects, the fixed dose combination of the present invention is administered to a patient with a low cell or tissue let-7 level. In other aspects, the present compositions are administered to a patient with a high cell or tissue HMGA2 level.

In other aspects, the compositions of the present inven-tions are administered to a patient with a high cell or tissue LIN28 level.

V. NEUROBLASTOMA

Neuroblastoma (NB) is a tumor of the autonomous ner-vous system originating from the adrenal medulla and autonomous ganglia in the chest and abdomen. After leuke-mia and brain tumors, NB is the most frequent cancer in infancy, the third most frequent malignant tumor of child-hood, and the leading cause of death due to solid tumors in children. The incidence in the United States is approxi-mately one in 7,000 children (Ater et al., 1998).

Therapy for NB is very intense, especially in advanced stages of the disease with widespread metastases to liver, bone, lymph nodes, and bone marrow. The current state of treatment for relapsed/refractory and high-risk NB patients is in flux, with many leading institutions using different approaches to therapy. Surgery, radiation therapy, chemo-therapy, and high-dose chemotherapy with subsequent bone marrow transplantation followed by differentiating therapy, along with antibody therapy, stem cell transplants and bio-logic therapy with retinoic acid are used in attempts to treat this patient group. More recently, immunotherapy has been added using monoclonal antibodies to the GD2 glycolipid antigen that is heavily expressed by NB cells (Bosslet et al., 1989; Cheung et al., 1998). Treatment associated toxicities are significant issues, especially in this pediatric population. Some patients are excluded from some of these treatment options (e.g., antibody therapy excludes patients with other than minimal residual disease). A recent phase I study found that no children in a group of 55 patients with relapsed or refractory NB and treated with irinotecan and temozolomide survived longer than three years (Children's Oncology Group).

Over the last 30 years, significant therapeutic progress has been made with an increase in the five-year relative survival rate from approximately 25% to 55%. However, almost 50% of patients are estimated to die of their tumor, and over the past decade improvement in the five-year survival rate of NB patients has been slow (Harras, 1996). NB has a par-ticularly poor prognosis in patients older than 2 years at diagnosis, advanced stage disease, and/or disease character-ized by MYCN gene amplification (Seeger et al., 1985; Brodeur, 2003). These more aggressive forms of NB respond poorly to chemotherapeutic approaches, and there-fore, there is great need for a better understanding of the cellular regulation of MYCN-amplified NB tumors in an effort to search for alternative molecular drug targets. Although a role for the MYCN oncoprotein has been estab-lished in NB pathogenesis, the mechanism by which MYCN contributes to both the development of this disease and its poor prognosis is still unclear. The MYCN oncoprotein functions as a transcriptional regulator (Ben-Yosef et al., 1998) and thus may influence tumorigenesis and patient survival by regulating the expression of key genes involved in the NB malignant phenotype. MYCN regulates the expression of genes that encode ornithine decarboxylase (ODC), the multi-drug resistance-associated protein 1 (MRP1), and MDM2 (Slack et al., 2005).

ODC is the rate-limiting enzyme in the production of polyamines (Marton and Pegg, 1995). Although polyamines, and therefore ODC, are essential for normal cell prolifera-tion, increased ODC activity can induce cellular transfor-mation in vitro (Auvinen et al., 1992), and high ODC levels are associated with a variety of tumors, including those of the brain and prostate (Mohan et al., 1999; Ernestus et al., 2001). In 2004, studies began investigating DFMO for the treatment of high-risk NB (Bachmann, 2004). DFMO is an enzyme-activated inhibitor of ornithine decarboxylase (ODC) and ODC is a rate-limiting enzyme of polyamine biosynthesis. Preclinical studies with DFMO showed that polyamine depletion is an effective therapeutic strategy in NB (Wallick et al., 2005). DFMO alters the polyamine-regulated p27Kip1/Rb signaling pathway that leads to G1 cell cycle arrest and prevents NB migration/invasion of cells (Wallic et al., 2005; Koomoa et al., 2008; Koomoa et al., 2013). ODC expression is a negative risk factor for NB independent of MYCN amplification (Geerts et al., 2010). ODC gene expression is directly activated by MYCN, and in a subset of patients is co-amplified with MYCN (Hogarty et al., 2008), suggesting that MYCN gene amplification leads to high ODC expression and subsequent high polyamine levels, which contribute to the malignant phenotype and the maintenance of NB tumorigenesis (Auvinen et al., 1992; Auvinen et al., 1995; Auvinen et al., 2003; Lutz et al., 1996; Ben-Yosef et al., 1998; Lu et al., 2003; Bachmann et al., 2012).

The secretion of polyamines in the urine as markers of neoplasia was proposed over 40 years ago (Russell and Levy, 1971). Technology and limited understanding of the metabolism and transport of these polycationic molecules restricted their development. It is now appreciated that export of the polyamines is a highly regulated process, involving acetylation of spermidine and spermine, which enables them to act as counterions for a solute carrier transporter that facilitates arginine transport (Xie et al., 1997; Uemura et al., 2008; Uemura et al., 2010), as depicted in FIG. 1. Substrates for the exporter of tissue polyamines have the general structure $R_1$—$NH_2^+$—$(CH_2)_{n>2}$—$NH_2^+$—$R_2$ (Xie et al., 1997). Thus, putrescine, monoacetylspermidine, and diacetylspermine, but neither spermidine nor spermine, are substrates for this exporter and might be expected to appear in the urine as a consequence of tissue attempts at homeostatic regulation under conditions of elevated polyamine metabolism. Spermidine, spermine, and mono-acetylspermine appear in the urine, but are likely either systemic degradation products resulting from cell lysis, serum amine oxidases (e.g., spermidine) or products of non-mammalian flora.

The relevance of seven polyamine metabolites in the urine, including those that are substrates for the polyamine exporter SLC3A2 and include putrescine, $N^1AcSpd$ and $N^1N^{12}Ac_2Spm$, were assessed. Only $N^1AcSpd$ was affected in a statistically significant manner by DFMO treatment during the first few weeks of therapy. This species is one of the most prevalent polyamine metabolites in urine and is notable in that it is targeted for export by acetylation by the SAT1 gene product, which is physically linked to the SLC3A2 exporter (Uemura et al., 2008). SAT1 also associates with ODC to form a potential metabolic channel for putrescine and polyamine synthesis and export.

DFMO treatment reduced urinary $N^1AcSpd$ contents during the first two weeks of treatment in the population as a whole. Reductions in urinary polyamine levels were most significant in patients with the ODC minor T risk allele at rs2302616. Disease progression was associated with increases in urinary levels of especially DAS, although putrescine and monoacetylspermidine levels were elevated in some patients. Diacetylspermine has previously been identified as a marker for tumor progression in adults with colon and breast cancer (Kawakita et al., 2011; Hiramatsu et al., 2005). Although the present study was a small study of 21 patients, urinary levels of polyamines, especially DAS appear to fluctuate with disease state and may be a marker of disease state that can be evaluated during therapy. These associations are currently under investigation in other phase I and II trials in patients with DFMO in NB. These increases could reflect mechanisms of resistance including elevated ODC enzyme levels requiring increased amounts of DFMO. It should be noted that no obvious DFMO dose-dependent responses were observed for either reductions of urinary polyamines or increases in PFS responses in this study. Subsequent studies investigating DFMO dose escalation in more detail are in progress.

VI. ROLE OF POLYAMINES IN NB CELL DIFFERENTIATION

The fluctuation in the levels of intracellular polyamines such as Put, Spd, and spermine (Spm) has been observed in association with cell differentiation (Heby, 1981; Tabor and Tabor, 1984; Pegg, 1986), and inhibition of ODC by DFMO and reduction in polyamine pools stimulates various cancer cells to differentiate (Chen et al., 1983; Melino et al., 1988; Melino et al., 1991). DFMO treatment of NB cells can change the triangular NB morphology by inducing a different phenotype; one which resembles elongated fibroblast-like cells without typical neuritic processes. By comparison, treatment with retinoic acid (RA) induces neural differentiation of NB cells as indicated by the outgrowth of definite neurites (Melino et al., 1988; Melino et al., 1991; Wainwright et al., 2001).

While the importance of ODC and polyamines in tumor growth has been well established (Casero and Marton, 2007; Pegg and Feith, 2007), the usefulness of DFMO in the treatment of pediatric NB had not been considered until recently (Bachmann, 2004; Wallick et al., 2005) and provided herein is the first trial to evaluate DFMO clinically in NB patients. Orally administered DFMO is an experimental therapy that has never received regulatory approval for any indication. High-dose intravenous (IV) DFMO received regulatory approval in 1990 for first-line treatment of West African sleeping sickness (trypanosomiasis), and is used by the World Health Organization in combination with nifurtimox, also referred to as Nifurtimox-Eflornithine-Combination-Therapy (NECT) (Priotto et al., 2009; Alirol et al., 2013). Topical DFMO is the active component of a commercial therapy for hirsutism (excess facial hair) (Blume-Peytavi and Hahn, 2008).

Further evidence of the importance of ODC in NB tumorigenesis is available from recent studies with human NB tumors. The expression levels of ODC mRNA from 88 NB patients were analyzed and significant correlations between ODC expression and the overall survival probability were found. High levels of ODC were predictive of low survival probability and vice versa. Most surprisingly, ODC was also predictive in tumors without MYCN amplification, thus suggesting that ODC also plays a role in NB tumorigenesis independent of MYCN amplification (AACR 2009, Abstract #3208). These findings were independently confirmed by two other groups (Hogarty et al., 2008; Rounbehler et al., 2009).

VII. RESULTS OF THE PHASE II PREVENTION TRIAL

High Risk Neuroblastoma (HRNB) remains a challenge in pediatric oncology, accounting for 15% of all pediatric cancer deaths. While most patients are able to attain remission, the natural history of HRNB is well documented with approximately half of patients relapsing within 5 years after completion of immunotherapy. The study in Example 7 evaluated the effectiveness of the ODC inhibitor difluoromethylornithine (DFMO), which targets cancer stem cell pathways in HRNB, as a maintenance therapy to prevent relapse in HRNB patients who were in complete remission at the completion of standard therapy. This study was an open label, single agent, multicenter study. Enrollment began in June 2012 and ended in February 2016. Subjects received 27 4-week cycles of oral DFMO at a dose of 500-1000 mg/m² twice daily. Event free survival (EFS) and overall survival (OS) were determined on an intention-to-treat basis. A total of 94 subjects received DFMO, 91 were eligible for the intention to treat (ITT) population. For all ITT subjects, EFS was 91% (±4%) and OS 98% (±2%) at 2 years. For the subgroup of subjects (n=74) who were previously enrolled on the ANBL0032 study, the 2 year EFS was 95% (±3%) and OS 98%. This is a significant improvement in comparison to ANBL0032 study which showed a conservative EFS of 76% 2 years post antibody therapy (p<0.01) and OS of 89% (p<0.01 based on parametric model). The one subject who relapsed and died from disease received only 50% dosing due to parent error. DFMO was well tolerated, with grade 2-3 transaminitis being the most common toxicity reported in <10% of patients. Administration of DFMO at 500-1000 mg/m² BID is an effective and safe dose. Following the completion of standard therapy for high-risk neuroblastoma DFMO treatment was associated with improved EFS and OS decreasing the high rate of relapse in children with HRNB.

High risk Neuroblastoma (HRNB) remains a challenge in pediatric oncology, accounting for 15% of all pediatric cancer deaths. There are 650-700 new cases of NB each year in US. While most patients are able to attain remission, the natural history of HRNB is well characterized showing that approximately 30% will relapse at 2 years and 50% will relapse by 5 years following completion of therapy (Simon et al., 2004; Yu et al., 2010; Cheung et al., 2012; Berthold et al., 2005). There is currently no curative treatment for children who relapse, and their 5-year survival rate is <10%.

Current treatment for HRNB consists of 5-6 cycles of induction chemotherapy (typically including cyclophosphamide, topotecan, cisplatin, etoposide, doxorubicin, and vincristine), surgical resection of the primary tumor, 1-2 cycles of high dose chemotherapy with autologous stem cell transplant (ASCT) followed by radiation therapy and maintenance with isotretinoin combined with chimeric anti-GD2 antibody (ch14.18) immunotherapy. Despite this intensive therapy, the 2-year event free survival (EFS) from the start of immunotherapy is reported to be 66±5% Yu et al., 2010 and, due to continued late relapses, the 4-year EFS was recently reported to be 59±5% Alice et al., 2014. Thus, prevention of post-therapy relapse is an important target to improve survival of HRNB patients.

Difluoromethylornithine (DFMO) is an enzyme-activated inhibitor of ornithine decarboxylase (ODC), which is a rate-limiting enzyme of polyamine biosynthesis. High polyamine content and elevated ODC expression has been shown in NB as well as many other tumors, and suppression of polyamine levels in cancer cells reduces tumor cell proliferation (Samal et al., 2013; Hixson et al., 1993). ODC inhibition by DFMO decreases LIN28 and increases Let7 levels, thus reversing an important cancer stem cell (CSC) pathway, and also has been shown to decrease neurosphere formation (Lozier et al., 2015).

Results of a Phase 1 study of DFMO in children with relapsed/refractory NB were recently published (Saulnier Sholler et al., 2015). The doses used in that trial normalized urine polyamines, indicating effective inhibition of the biologic target. The median progression free survival (PFS) for all 18 evaluable subjects was 80.5 days (95% CI: 62-418 days). More significantly, three subjects remain alive without progression of disease between 2-4.5 years after starting DFMO and 1-3 years following completion of DFMO therapy without receiving further treatment. DFMO was safe at all dose levels studied with no dose-limiting toxicities (DLTs) or drug related serious adverse events (SAEs).

The Phase II study was designed to evaluate further the effectiveness of DFMO in preventing relapse of HRNB patients who were in complete remission at the completion of standard upfront therapy.

NMTRC003 evaluated DFMO as maintenance therapy for children with HRNB in complete remission after completion of standard therapy that included chemotherapy, surgery, high-dose chemotherapy with ASCT, radiation, and anti-GD2 antibody with isotretinoin. The results indicate that 500-1000 mg/m² twice daily of DFMO can prevent relapse and improve EFS and OS for this patient population, with a 2-year EFS of 91% and OS of 98%. There have been no late relapses following completion of DFMO therapy with the longest follow-up being 3.5 years from enrollment.

Subject characteristics with regards to the incidence of high risk features and the number of subjects receiving single vs. double transplant prior to antibody therapy were not significantly different than those previously reported for subjects enrolled on COG ANBL0032. Indeed, 74 subjects who enrolled on this study had been previously enrolled and treated on ANBL0032. While this cohort would be expected to follow the survival curves for ANBL0032 (Yu et al., 2010) in which, after statistical correction for the run in period during which patients were receiving antibody, the 2-year EFS for those who were progression-free at the completion of antibody therapy can be conservatively estimated at 76%, the observed 2-year EFS on our study was 95% (+/−3%). Furthermore, while event-free survival of subjects enrolled on ANBL0032 continues to drift lower after the 2-year post-antibody time point, our results have stayed stable up to 3.5 years from enrollment, suggesting that treatment with DFMO continues to protect against relapse even after discontinuing the drug. While subjects on ANBL0032 with a response status of CR or Very Good Partial Response (VGPR) prior to high-dose therapy/ASCT had better outcomes compared to those with a Partial Response, subjects on this study did equally well regardless of disease status pre-transplant. Similarly, subjects on ANBL0032 with a Curie score>0 (n=15/100) immediately pre-immunotherapy had a 3-year EFS of 28.9%±6.8% (Yanik et al., 2013), while all of the 4/52 subjects on this study identified with Curie score>0 prior to immunotherapy remain in remission at greater than 2 years.

DFMO does not appear to act as a standard anti-neoplastic agent by inducing death of dividing cancer cells. Preclinical work has shown that ODC inhibition, through effects on the LIN28/Let7 pathway, may induce irreversible changes in the phenotype of CSCs, thus reducing the potential for this cell population to support tumor recurrence (Samal et al., 2013; Lozier et al., 2015). Targeting of HRNB CSC, is potentially the mechanism by which DFMO is acting to prevent relapse and should be further studied.

The current study is limited by the absence of a randomized control group; however, the fact that the vast majority of subjects who enrolled on this protocol did so following enrollment on ANBL0032 suggests that the data for the ANBL0032 protocol does constitute a valid comparison group. In addition, a disease status of CR was required for entry on this protocol which might also have biased results. However, while ANBL0032 did enroll patients with residual disease, the published analysis of efficacy specifically excluded those subjects who had biopsy-proven residual disease at the time of study entry. Furthermore, subjects on ANBL0032 whose disease status assessed prior to high-dose chemotherapy and ASCT as VGPR had almost identical outcomes to those with a disease status of CR (Yu et al., 2010). Together, these data suggest that any bias that might have been introduced by the eligibility requirement for CR (as defined by this study) would be minimal and quite inadequate to account for the magnitude of the observed difference in EFS and OS between this study and the ANBL0032 experience.

DEMO doses similar to doses used in this study have been shown to be effective in decreasing urinary polyamine levels (Phase I), in decreasing colonic mucosal levels of polyamines (Meyskens et al., 1993) and in significantly inhibiting phorbol ester-induced skin ODC activity (Bailey et al., 2010). DFMO at this dose appears to be a very safe medication. It has been used for approximately 30 years by the WHO for African sleeping sickness, and is approved in the US in the form of a skin cream for hair removal. Prior trials of oral DFMO at 500 mg/m²/day revealed it to be safe (Bailey et al., 2010) and a prior phase I study in adults who were given doses of 3.75 g/m²/day—5 times higher than doses given in this study—demonstrated no clinically significant renal, hepatic, auditory or hematologic toxicities (Griffin et al., 1987). The present study confirmed the safety of DFMO at this dose in children with HRNB, specifically with regards to significant or irreversible ototoxicity.

Long term side effects from standard treatment for children with HRNB include cardiotoxicity, ototoxicity, hypothyroidism, second malignancies and post-transplant complications (Martin et al., 2014; Simon et al., 2002; Laverdiere et al., 2009). This study demonstrates that DFMO at 500-1000 mg/m$^2$ BID is safe and significantly decreases the high rate of relapse in children with HRNB in the first 2 years following standard upfront therapy, prolonging EFS and OS.

VIII. CANCER STEM CELLS

As used in the specification and claims, the terms "cancer stem cell(s)" and "CSC" are interchangeable and refer to solid cancer stem cells. CSCs are mammalian, and in preferred embodiments, these CSC are of human origin, but they are not intended to be limited thereto.

One hypothesis to explain how tumors grow and metastasize is the cancer stem cell hypothesis, which states that there is a small, distinct subset of cells within each tumor that is capable of indefinite self-renewal and of developing into the more adult tumor cell(s), which are relatively limited in replication capacity. It has been hypothesized that these cancer stem cells (CSC) might be more resistant to chemotherapeutic agents, radiation or other toxic conditions, and thus, persist after clinical therapies and later grow into secondary tumors, metastases or be responsible for relapse. See, for example, Chaffer and Weinberg (2015).

Solid tumors are thought to arise in organs that contain stem cell populations. The tumors in these tissues consist of heterogeneous populations of cancer cells that differ markedly in their ability to proliferate and form new tumors; this difference in tumor-forming ability has been reported for example with breast cancer cells and with central nervous system tumors. While the majority of the cancer cells have a limited ability to divide, recent literature suggests that a population of cancer cells, termed cancer stem cells, has the exclusive ability to extensively self-renew and form new tumors. Growing evidence suggests that pathways that regulate the self-renewal of normal stem cells are deregulated or altered in cancer stem cells, resulting in the continuous expansion of self-renewing cancer cells and tumor formation.

Cancer stem cells comprise a unique subpopulation (often 0.1%-10% or so) of a tumor that, relative to the remaining 90% or so of the tumor (i.e., the tumor bulk), are more tumorigenic, relatively more slow-growing or quiescent, and often relatively more chemoresistant than the tumor bulk. Given that conventional therapies and regimens have, in large part, been designed to attack rapidly proliferating cells (i.e., those cancer cells that comprise the tumor bulk), cancer stem cells, which are often slow-growing, may be relatively more resistant than faster growing tumor bulk to conventional therapies and regimens. Cancer stem cells can express other features that make them relatively chemoresistant, such as multi-drug resistance and anti-apoptotic pathways. The aforementioned would constitute a key reason for the failure of standard oncology treatment regimens to ensure long-term benefit in most patients with advanced stage cancers—i.e., the failure to adequately target and eradicate cancer stem cells. In some instances, a cancer stem cell(s) is the founder cell of a tumor (i.e., it is the progenitor of the cancer cells that comprise the tumor bulk).

In certain embodiments, a method comprises the steps of obtaining a biological sample from a subject to be tested; detecting the presence of cancer stem cells in the sample, wherein if cancer stem cells are present, then the subject has an increased likelihood of having a tumor enriched with cancer stem cells. In one embodiment, the biological sample is a blood sample or a cell sample from a tumor in the subject.

Detecting the presence of cancer stem cells may comprise detecting the presence of a biomarker expressed on cancer stem cells, such as the absence of CD38 or the presence of CD34, ALDH, NOTCH, CD133, CD44, CD24, EpCAM, THY1, CD200, SSEA-1, and/or EGFR. A biomarker may be detected using any method known in the art, such as, for example, quantitative or qualitative detection of mRNA (e.g., qPCR, microarray, in situ hybridization, Northern blotting, nuclease protection, etc.) or quantitative or qualitative detection of protein (e.g., mass spectrometry, FACS, ELISA, western blotting, etc.)

IX. EFFECT OF DFMO IN A TRANSGENIC NEUROBLASTOMA ANIMAL MODEL

Two groups (Hogarty et al., 2008; Rounbehler et al., 2009) confirmed the effect of DFMO in vivo using the TH-MYCN NB mouse model. DFMO in combination with cisplatin and cyclophosphamide increased the tumor-free survival of TH-MYCN homozygous mice (Hogarty et al., 2008). Additional studies have revealed that DFMO combined with SAM486A act synergistically and result in a significantly reduced tumor burden in TH-MYCN mice (AACR 2009, Abstract #3203).

X. POLYMORPHISM ANALYSIS

Single nucleotide polymorphisms (SNPs) in the ODC gene have been associated with risk of specific cancers (Martinez et al., 2003; Visvanathan et al., 2004; Brown et al., 2009). The minor A allele at rs2302615 in the ODC gene was found to be a risk allele for survival in patients with prior colorectal cancer (Zell et al., 2009), but a protective allele in patients with NB (Norris et al., 2014). The SNP at rs2302615 affects binding to the surrounding DNA elements of e-box transcription factors (Martinez et al., 2003; Zell et al., 2009; Norris et al., 2014), which interact with transcription factors acting at an upstream SNP (rs2302616) (Garcia-Huidobro et al., 2014a). The minor T allele at rs2302616 disrupts a G-quadraplex structure in the ODC gene, increases ODC promoter activity, and is associated with increased putrescine content in rectal tissues from patients with risk of colorectal cancer (Garcia-Huidobro et al., 2014a; Garcia-Huidobro et al., 2014b). Patients in a colorectal adenoma prevention trial with this genotype also display maximal response to a combination of agents targeting the polyamine pathway (Garcia-Huidobro et al., 2014b), suggesting that the minor T-allele at rs2302616 may convey a "polyamine addiction" phenotype.

The genotype of ODC1 of a patient can determined using the methods provided below, including the specific methods described in the Examples section. These methods can be further modified and optimized using the principles and techniques of molecular biology as applied by a person skilled in the art. Such principles and techniques are taught, for example, in Small et al. (2002), which is incorporated herein by reference. General methods employed for the identification of single nucleotide polymorphisms (SNPs) are provided below. The reference of Kwok and Chen (2003)

and Kwok (2001) provide overviews of some of these methods; both of these references are specifically incorporated by reference.

SNPs relating to ODC1 can be characterized by the use of any of these methods or suitable modification thereof. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism, or any other biochemical interpretation.

A. DNA Sequencing

A commonly used method of characterizing a polymorphism is direct DNA sequencing of the genetic locus that flanks and includes the polymorphism. Such analysis can be accomplished using either the "dideoxy-mediated chain termination method," also known as the "Sanger Method" (Sanger et al., 1975) or the "chemical degradation method," also known as the "Maxam-Gilbert method" (Maxam et al., 1977). Sequencing in combination with genomic sequence-specific amplification technologies, such as the polymerase chain reaction, may be used to facilitate the recovery of the desired genes (Mullis et al., 1986; European Patent Application 50,424; European Patent Application 84,796; European Patent Application 258,017; European Patent Application. 237,362; European Patent Application. 201,184; U.S. Pat. Nos. 4,683,202; 4,582,788; and 4,683,194), all of the above incorporated herein by reference.

B. Exonuclease Resistance

Other methods that can be employed to determine the identity of a nucleotide present at a polymorphic site use a specialized exonuclease-resistant nucleotide derivative (U.S. Pat. No. 4,656,127). A primer complementary to an allelic sequence immediately 3' to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known, one can determine the specific nucleotide present in the polymorphic site of the DNA.

C. Microsequencing Methods

Several other primer-guided nucleotide incorporation procedures for assaying polymorphic sites in DNA have been described (Komher et al., 1989; Sokolov, 1990; Syvanen 1990; Kuppuswamy et al., 1991; Prezant et al., 1992; Ugozzoll et al., 1992; Nyren et al., 1993). These methods rely on the incorporation of labeled deoxynucleotides to discriminate between bases at a polymorphic site. As the signal is proportional to the number of deoxynucleotides incorporated, polymorphisms that occur in runs of the same nucleotide result in a signal that is proportional to the length of the run (Syvanen et al., 1990).

D. Extension in Solution

French Patent 2,650,840 and PCT Application WO91/02087 discuss a solution-based method for determining the identity of the nucleotide of a polymorphic site. According to these methods, a primer complementary to allelic sequences immediately 3' to a polymorphic site is used. The identity of the nucleotide of that site is determined using labeled dideoxynucleotide derivatives that are incorporated at the end of the primer if complementary to the nucleotide of the polymorphic site.

E. Genetic Bit Analysis or Solid-Phase Extension

PCT Application WO92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here the primer or the target molecule is immobilized to a solid phase.

F. Oligonucleotide Ligation Assay (OLA)

This is another solid phase method that uses different methodology (Landegren et al., 1988). Two oligonucleotides, capable of hybridizing to abutting sequences of a single strand of a target DNA are used. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide by using avidin. Other nucleic acid detection assays, based on this method, combined with PCR, have also been described (Nickerson et al., 1990). Here PCR is used to achieve the exponential amplification of target DNA, which is then detected using the OLA.

G. Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone and unlike the polymerase-based assays, this method enhances the specificity of the polymerase step by combining it with a second hybridization and a ligation step for a signal to be attached to the solid phase.

H. Invasive Cleavage Reactions

Invasive cleavage reactions can be used to evaluate cellular DNA for a particular polymorphism. A technology called INVADER® employs such reactions (e.g., de Arruda et al., 2002; Stevens et al., 2003, which are incorporated by reference). Generally, there are three nucleic acid molecules: 1) an oligonucleotide upstream of the target site ("upstream oligo"), 2) a probe oligonucleotide covering the target site ("probe"), and 3) a single-stranded DNA with the target site ("target"). The upstream oligo and probe do not overlap but they contain contiguous sequences. The probe contains a donor fluorophore, such as fluoroscein, and an acceptor dye, such as Dabcyl. The nucleotide at the 3' terminal end of the upstream oligo overlaps ("invades") the first base pair of a probe-target duplex. Then the probe is cleaved by a structure-specific 5' nuclease causing separation of the fluorophore/quencher pair, which increases the amount of fluorescence that can be detected. See Lu et al. (2004). In some cases, the assay is conducted on a solid-surface or in an array format.

I. Other Methods to Detect SNPs

Several other specific methods for polymorphism detection and identification are presented below and may be used as such or with suitable modifications in conjunction with identifying polymorphisms of ODC1 in the present invention. Several other methods are also described on the SNP web site of the NCBI on the World Wide Web at ncbi.nlm.nih.gov/SNP, incorporated herein by reference.

In a particular embodiment, extended haplotypes may be determined at any given locus in a population, which allows one to identify exactly which SNPs will be redundant and which will be essential in association studies. The latter are referred to as 'haplotype tag SNPs (htSNPs)', markers that capture the haplotypes of a gene or a region of linkage disequilibrium. See Johnson et al. (2001) and Ke and Cardon (2003), each of which is incorporated herein by reference, for exemplary methods.

The VDA-assay utilizes PCR amplification of genomic segments by long PCR methods using TaKaRa LA Taq reagents and other standard reaction conditions. The long amplification can amplify DNA sizes of about 2,000-12,000 bp. Hybridization of products to a variant detector array (VDA) can be performed by an Affymetrix High Throughput Screening Center and analyzed with computerized software.

A method called Chip Assay uses PCR amplification of genomic segments by standard or long PCR protocols. Hybridization products are analyzed by VDA, Halushka et al. (1999), incorporated herein by reference. SNPs are generally classified as "Certain" or "Likely" based on computer analysis of hybridization patterns. By comparison to alternative detection methods, such as nucleotide sequencing, "Certain" SNPs have been confirmed 100% of the time; and "Likely" SNPs have been confirmed 73% of the time by this method.

Other methods simply involve PCR amplification following digestion with the relevant restriction enzyme. Yet others involve sequencing of purified PCR products from known genomic regions.

In yet another method, individual exons or overlapping fragments of large exons are PCR-amplified. Primers are designed from published or database sequences and PCR-amplification of genomic DNA is performed using known conditions. Thermal cycling is performed and resulting PCR-products are analyzed by PCR-single strand conformation polymorphism (PCR-SSCP) analysis, under a variety of conditions, e.g, 5% or 10% polyacrylamide gel with 15% urea, with or without 5% glycerol. Electrophoresis is performed overnight. PCR-products that show mobility shifts are reamplified and sequenced to identify nucleotide variation.

XI. PHARMACEUTICAL FORMULATIONS AND ROUTES OF ADMINISTRATION

The therapeutic compounds of the present disclosure may be administered by a variety of methods, e.g., orally or by injection (e.g., subcutaneous, intravenous, intraperitoneal, etc.). Depending on the route of administration, the active compounds may be coated in a material to protect the compound from the action of acids and other natural conditions that may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

Formulations for oral administration may be specifically formulated for pediatric use. The therapeutic compound may be prepared as a powder, which may be packaged in individual (i.e., single-use) unit doses. The powder formulation may be in granulated form having, for example, a particle size within the range of about 1 µM to about 2000 µM in diameter. Individual unit doses may be in the form of sachets, capsules, etc. The powdered therapeutic compound in an individual unit dose may be formulated with one or more excipient, filler (e.g., starches, lactose, mannitol, Pearlitol™ SD 200, cellulose derivatives, sugar, and the like), binder (e.g., hydroxypropylcellulose (Klucel™-LF), hydroxypropyl methylcellulose or hypromellose (Methocel™), polyvinylpyrrolidone or povidone (PVP-K25, PVP-K29, PVP-K30, PVP-K90), plasdone S 630 (copovidone), powdered acacia, gelatin, guar gum, carbomer (e.g., carbopol), methylcellulose, polymethacrylates, and starch), disintegrant (e.g., carmellose calcium, carboxy methylstarch sodium, croscarmellose sodium, crospovidone, and low-substituted hydroxypropylcellulose), flavorant, or sweetener. The powdered therapeutic compound in an individual unit dose may be formulated without an excipient, filler, binder, disintegrant, flavorant, or sweetener. The powdered formulation may comprise an anti-adherent agent, such as, for example, talc, silica derivatives, or silicon dioxide. The powdered therapeutic compound may be administered as a powder. The powdered therapeutic compound may be reconstituted in food or drink prior to oral administration.

The therapeutic compound may be prepared as a liquid concentrate, which may be packaged in individual (i.e., single-use) unit dose or in multi-use dose formats. Concentrated liquid formulations may comprise the therapeutic agent and a solvent (e.g., an organic or aqueous solvent). Concentrated liquid formulations include solutions, syrups, etc. A concentrated liquid formulation may comprise a component to mask the taste of the therapeutic compound. A liquid composition for oral administration may be obtainable by mixing the concentrated liquid formulation with an aqueous medium. A multi-use dose format of concentrated liquid may be provided with an at-home dispending method.

The therapeutic compound may be prepared as a tablet coated for pediatric administration. A tablet may be scored. A scored table may comprise a single unit dose or multiple unit doses. A scored multiple unit dose tablet may be converted into single unit doses by cutting along said scoring. In some aspects, a tablet will readily dissolve in water for liquid administration.

The therapeutic compound may be prepared in a chewable form. Such a chewable form may be soft (e.g., gelatinous) or hard. The chewable form may comprise a chewable base(s) (e.g., xylitol, mannitol and sorbitol), binder(s) (e.g., hydroxypropyl cellulose, polyvinylpyrrolidone, pregelatinized starch and the like), disintegrants (e.g., crospovidone, sodium starch glycolate, starches such as maize starch and dried starch, croscarmellose sodium and cellulose products such as microcrystalline cellulose, microfine cellulose, low substituted hydroxypropylcellulose), lubricants (e.g., magnesium stearate, colloidal silicon dioxide and the like), sweetening agents (e.g., natural sweeteners such as sugars and artificial sweetening agents such as sodium saccharin or aspartame), coloring agents, and flavoring agents (e.g., fruit flavours, which may be natural or synthetic). Any of the foregoing formulations may be stable a room temperature. Any of the foregoing formulations may be stable at about 4° C.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is +10% of the blood glucose level of a non-diabetic subject.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the subject has eaten or will eat.

XII. COMBINATION THERAPY

Effective combination therapy may be achieved with a single composition or pharmacological formulation that includes both agents, or with two distinct compositions or formulations, wherein one composition includes a compound of this invention, and the other includes the second agent(s). In aspects involving two distinct compositions or formulations, the other agent may be administered before, concurrently with, or following administration of e.g., DFMO. The therapy may precede or follow the other agent treatment by intervals ranging from minutes to months. In some aspects, one would ensure that a significant period of time did not expire between the time of each delivery, such that each agent would still be able to exert an advantageously combined effect. In such instances, it is contemplated that one would typically administer e.g., DFMO and the other therapeutic agent within about 12-24 hours of each other and, more preferably, within about 6-12 hours of each other. In some aspects, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, such as where "A" represents the first agent (e.g., DFMO) and "B" represents a secondary agent, non-limiting examples of which are described below:

| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A |
| B/A/B/A | B/A/A/B | A/A/A/B | B/A/A/A | A/B/A/A | A/A/B/A |

It is contemplated that agents that modulate the polyamine pathway may be used in conjunction with the treatments of the current invention. For example, non-steroidal anti-inflammatory drugs (NSAIDs), polyamine transporter inhibitors, eIF-5A antagonists, chemotherapeutic agents, radiotherapy, and immunomodulatory agents may be used.

A. NSAIDs

NSAIDs are anti-inflammatory agents that are not steroids. In addition to anti-inflammatory actions, they have analgesic, antipyretic, and platelet-inhibitory actions. They are used primarily in the treatment of chronic arthritic conditions and certain soft tissue disorders associated with pain and inflammation. They act by blocking the synthesis of prostaglandins by inhibiting cyclooxygenase, which converts arachidonic acid to cyclic endoperoxides, precursors of prostaglandins. Inhibition of prostaglandin synthesis accounts for their analgesic, antipyretic, and platelet-inhibitory actions; other mechanisms may contribute to their anti-inflammatory effects. Certain NSAIDs also may inhibit lipoxygenase enzymes or phospholipase C or may modulate T-cell function. Examples of NSAIDS that may be used either alone or in combination include, but are not limited to, aspirin, ibuprofen, naproxen, fenoprofen, ketoprofen, flurbiprofen, oxaprozin, indomethacin, sulindac, etodolac, diclofenac, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib parecoxib, lumiracoxib, and etoricoxib.

B. Polyamine Transporter Inhibitors

Inhibitors of the polyamine transport include, but are not limited to, 4-bis(3-aminopropyl)-piperazine (BAP) and compounds disclosed in U.S. Patent Publn. No. 2011/0256161 (e.g., AMXT1501); U.S. Patent Publn. No. 2012/0172449; PCT Publn. No. WO 1999/054283; U.S. Pat. Nos. 6,083,496; and 5,456,908.

C. eIF-5A Antagonists

Hypusine (NE-(4-amino-2 (R)-hydroxybutyl) lysine) is a unique amino acid that is formed on a synthesized protein by posttranslational modification. Hypusine is only known to occur in a single protein, eukaryotic translation initiation factor 5A (eIF-5A). The formation of hypusine occurs by two distinct steps involving modification of a single lysyl amino acid residue on the eIF-5A protein. This process is required for the biosynthesis of bioactive eIF-5A. Inhibitors of this process include, but are not limited to, N1-guanyl-1,7-diaminoheptane (GC7), and proteasome inhibitors (e.g., bortezomib, disulfiram, epigallocatechin-3-gallate, salinosporamide, carfilzomib, ONX 0912, CEP-18770, MLN9708, and epoxomicin).

D. Chemotherapeutic Agents

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; sizofiran; spirogermanium; tenuazonic acid; triaziquone; 2,2',2"-razoxane; rhizoxin; trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, PI3K inhibitors (e.g., perifosine, idelalisib, PX-866, IPI-145, BAY 80-6946, BEZ235, RP6530, TGR 1202, SF1126, INK1117, GDC-0941 BKM120, XL147 (also known as SAR245408), XL765 (also known as SAR245409), palomid 529, GSK1059615, ZSTK474, PWT33597, IC87114, TG100-115, CAL263, RP6503, PI-103, GNE-477, CUDC-907, AEZS-136), aurora kinase inhibitors (e.g., ZM447439, hesperadin, VX-680, and those disclosed in U.S. Pat. No. 8,815,872 and WO 2012/135641), transplatinum, and pharmaceutically acceptable salts, acids, or derivatives of any of the above.

E. Immunomodulatory Agents

The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule (e.g., an anti-GD2 chimeric antigen receptor) that interacts, either directly or indirectly, with a tumor cell target. See, e.g., U.S. Patent Publn. No. 2014/0004132. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include GD2, CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; U.S. Pat. Nos. 5,830,880 and 5,846,945); and monoclonal antibodies, e.g., anti-CD20, anti-ganglioside GM2, anti-GD2 [e.g., Ch14.18] (Yu et al., 2010; U.S. Patent Appln. Publn. Nos. 20130216528 and 20140170155; PCT Appln. Publn. WO 2014144763; U.S. Pat. Nos. 6,451,995, 8,507,657 and 8,278,065), and anti-p185 (Hollander, 2012; Hanibuchi et al., 1998; U.S. Pat. No. 5,824,311). It is contemplated that one or more anti-cancer therapies may be employed with the antibody therapies described herein.

F. Radiotherapy

Other factors that cause DNA damage and have been used extensively include what are commonly known as $\gamma$-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

G. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

H. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

XIII. DEFINITIONS

As used in the claims, when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The term "effective," as that term is used in the specification and/or claims, means adequate to accomplish a desired, expected, or intended result.

As used herein, the term "$IC_{50}$" refers to an inhibitory dose which is 50% of the maximum response obtained.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Effective amount," "therapeutically effective amount," or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

XIV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Patient and Methods

Patient Eligibility. Patients were enrolled into the Neuroblastoma and Medulloblastoma Translational Research Consortium (NMTRC) 002 study from March 2010 to October 2012. This was an open label, multicenter, phase I dose escalation study with seven subjects from Vermont Children's Hospital, eight subjects from the Helen DeVos Children's Hospital, four subjects from the Arnold Palmer Hospital for Children, one subject from the Levine Children's Hospital, and one subject from the Children's Hospital of Orange County. To be eligible for this study, subjects had to fulfill the following criteria: (a) age 0-21 years at the time of diagnosis; (b) histologic verification at either the time of original diagnosis or relapse of NB; (c) disease status verified as refractory or relapsed NB; (d) measurable disease based on measurable tumor (>10 mm by CT or MRI), positive MIBG, and abnormal urinary catecholamine levels or positive bone marrow biopsy/aspirate; (e) disease state was one for which there was no known curative therapy; (f) negative urine pregnancy test for female subjects of child bearing potential (onset of menses or ≥13 years of age); and (g) adequate liver function as defined by AST and ALT<10× normal. Exclusion criteria were life expectancy<2 months, Lansky score<30%, or subjects who were concurrently receiving another investigational drug or anticancer agent. Subjects had to be fully recovered from the effects of prior chemotherapy (hematological and bone marrow suppression effects). Subjects were excluded if they had an uncontrolled infection until the infection was controlled. Subjects who were not able to comply with the safety monitoring requirements of the study were also excluded. This trial was approved by the Western Institutional Review Board as well as by local Institutional Review Boards at each enrolling site. Informed consent from the patient or their guardian(s) and assent, as appropriate, were obtained prior to study entry. ClinicalTrials.gov Identifier: NCT01059071.

Patient Characteristics. Twenty-one subjects with refractory or recurrent NB were enrolled in this study between March 2010 and October 2012. The subject characteristics are shown in Table 2. Every subject had previously received standard therapy for their disease and had relapsed or was refractory to therapy. The median age was nine years old, with a range of 1-17 years old.

TABLE 2

Characteristics of patients enrolled in NMTRC 002
(ClinicalTrials.gov Identifier: NCT01059071)

| Enrollment | N |
|---|---|
| Total Enrolled | 21 |
| Total Received Drug | 21 |
| Evaluable | N (%) |
| Efficacy Evaluable | 18 (86) |
| Safety Evaluable | 21 (100) |
| Age | Years |
| Mean | 8.75 |
| Median | 9 |
| Sex | N (%) |
| Male | 14 (67) |
| Female | 7 (33) |
| Race | N (%) |
| Caucasian | 14 (67) |
| Hispanic | 3 (14) |
| Black or African American | 2 (9.5) |
| More than one race or unknown | 2 (9.5) |

Study Design and Treatment. The NMTRC 002 study design is shown in FIG. 3. This trial was a standard 3+3 Phase I dose escalation design. In order to address safety, patient replacement was allowed if a patient withdrew from the trial for non-drug related reasons prior to completion of 2 cycles of the protocol. Patients displaying a clinical response were allowed to remain on treatment until disease progression occurred or mutual decision of their physician and parents. Subjects were enrolled at one of four escalating doses. Three evaluable subjects were enrolled at 500 mg/m² BID, three evaluable subjects at 750 mg/m² BID, three evaluable subjects at 1000 mg/m² BID, and six evaluable subjects at 1500 mg/m² BID. Twenty-one subjects received at least one dose of DFMO as a single agent and were evaluable for safety. Eighteen of those subjects completed cycle 1 and were evaluable for efficacy. Fifteen subjects completed at least the first two cycles of DFMO (alone and in combination with etoposide) and comprise the population evaluable for dose limiting toxicity. Of the eighteen subjects that were evaluable for efficacy, two subjects completed 1 cycle, seven subjects completed 3 cycles, two subjects completed 5 cycles, one subject completed 7 cycles (cycles 6-7 DFMO alone), one subject completed 10 cycles, one subject completed 12 cycles (cycles 7-12 DFMO alone), lone subject completed 15 cycles (cycles 6-15 DFMO alone), two subjects completed 17 cycles (on subject cycles 6-17 DFMO alone), and one subject completed 43 cycles on study (cycles 7-43 DFMO alone).

Drug Formulation and Administration. Subjects received single agent DFMO administered orally on Days 1-21 of the first 21-day cycle. DFMO was supplied as a powder that was dissolved in juice or water prior to administration. The starting dose was 500 mg/m$^2$ PO BID (Dose Level 1). Dose escalation took place in a standard 3+3 design, in which doses increased by approximately 20%-25% in successive 3-subject cohorts. Enrollment of the next cohort occurred after the entire previous cohort had completed both cycles 1 (single agent) and 2 (combination) of treatment without any dose limiting toxicity (DLT), as reviewed by the Data and Safety Monitoring Committee. After the first cycle of single agent DFMO, subjects continued to receive BID DFMO at the dose established as safe and tolerable during cycle 1, and also received oral Etoposide at 50 mg/m$^2$/dose (rounded to the nearest 50 mg) once daily for the first 14 days of Cycles 2-5. The final cohort of DFMO received an additional 3 enrollments as a confirmation cohort, so that six subjects received the 1500 mg/m$^2$ BID dose of DFMO.

Patient Safety and Treatment Response Evaluation. Weekly monitoring for treatment related toxicities included a physical exam, vital signs (temperature, pulse rate, and sitting blood pressure) CBC, AST/ALT, LDH, bilirubin, electrolytes, BUN, creatinine, review and recording of concomitant medications, and monitoring of AE's with a review of concurrent illnesses. In addition, Lansky or ECOG score and urine catecholamines were measured prior to every 21 day cycle. An audiogram was performed at the end of cycles 1, 3, and 5. Subjects without bone marrow metastases were required to have adequate bone marrow function as defined by ANC>500/μL and platelets>50,000/μL before starting chemotherapy. Clinical and laboratory adverse events were graded according to the NCI common terminology criteria for adverse events (CTCAE) version 3.0.

Tumor and clinical responses were monitored as secondary endpoints. Eighteen subjects were evaluated for efficacy. This study used the (RECIST) Response Evaluation Criteria measurements in Solid Tumor from the NCI (27) modified for pediatrics as well as MIBG or PET and bone marrow response. Tumor assessments/imaging studies were obtained at baseline>7 days from prior therapy and <21 days from the start of study therapy. These were repeated at the end of the first cycle and again after every other cycle.

Pharmacokinetic (PK) Analytical Method and Sample Collection. Patients were consented for all pharmacokinetic sampling and analysis. DFMO analytical methods were performed in compliance with Good Laboratory Practice (GLP), under contract with inVentiv Health Clinique (Quebec, Canada). Briefly, the analyte DFMO and its internal standard were extracted from a 0.025 mL aliquot of human serum. The extracted samples were injected into a liquid chromatograph equipped with an Atlantis Hilic Silica, 50×4.6 mm, 3 μm column. The mobile phase A was a mixture of Milli-Q type water with acetonitrile and ammonium acetate. The validated calibration range for this assay was from 50 to 100,000 ng/mL. Blood was drawn from patients immediately prior to taking a morning oral DFMO dose during cycles 1 (DFMO alone) and 2 (DFMO+etoposide) and at 0.5, 1, 3 and 6 hours after drug administration. DFMO levels were then assessed in serum obtained from these blood samples. Blood was not collected beyond 6 hours post dose as this trial was conducted on an outpatient basis, and this was judged to be an undue burden on patients.

ODC Genotype. Patients were consented for genetic analysis in NMTRC 002. ODC rs2302615 and rs2302616 genotypes were determined from blood samples by pyrosequencing methods, under contract with EpigenDx (epigendx.com).

Urinary Polyamine Levels. Patients were consented for urine analysis in NMTRC 002. Spot urine (first void of the day) was collected on days 1, 8, and 15 of cycle 1 (DFMO only) and frozen at −80° C. until analysis of polyamines levels. Polyamines with at least one free primary amine were quantified using reverse-phase high-performance liquid chromatography (HPLC) as previously described (Thompson et al., 2010). Urinary N$^1$,N$^{12}$-diacetylspermine (N$^1$,N$^{12}$-Ac$_2$Spm or DAS) was determined using the auto DAS reagent kit (Alfresa Pharma Co., Osaka, Japan), according to the manufacturer's instructions. The assay involves the specific binding between a bovine serum albumin-acetyl-spermine conjugate, as a DAS mimic, and colloidal gold antibody complexes, and has been previously described (Kawakita et al., 2011).

Statistical Methods. Pharmacokinetic parameters $C_{max}$, $t_{max}$ and $AUC_{0-6}$ are presented as the mean and standard deviation of all observed values at each dose level, and were analyzed using SAS (ver. 9.2). Urinary polyamine levels were derived from duplicate measurements of individual samples. Significance of associations between urinary polyamine contents at baseline, or change in urinary polyamine contents from baseline after one week of DFMO therapy, progression free survival (PFS) and ODC genotype was assessed using the Student T-Test (Excel®). Fisher's Exact Test was used to assess the likelihood that increases in urinary polyamine levels were associated with disease progression. Friedman's test for repeated measures analysis of variance was used to assess changes in contents of individual urinary polyamines.

Example 1—Safety of Oral DFMO and Etoposide

The primary aim of the phase I clinical trial was to study the safety of the ODC inhibitor α-difluoromethylornithine (DFMO) alone and in combination with a cytotoxic chemotherapeutic drug in pediatric patients with refractory or recurrent NB. Etoposide was chosen for the combination, as it has reported efficacy in this patient group (Kushner et al., 2013) and is synergistic with DFMO in some cell models (Dorr et al., 1986). The secondary aims were to investigate the activity, pharmacokinetics and genetic and metabolic factors associated with ODC.

No dose-limiting toxicities (DLTs) or drug related serious adverse events (SAEs) were observed in this study. Study related (possibly, probably, and definitely related) toxicities observed during all cycles are summarized in Table 3. Those related to DFMO alone consisted of anemia (N=3), ANC decrease (N=2), decreased platelet count (N=2), ALT increase (N=1), AST increase (N=1), anorexia (N=1), constipation (N=1), diarrhea (N=1), infection (conjunctivitis) (N=1), hypoalbuminemia (N=1), hypophosphatemia (N=1), increased GGT (N=1), sleep disturbance (N=1), urinary retention (N=1), and vomiting (N=1). Six subjects were enrolled in the 1500 mg/m$^2$ BID dose and no DLTs were observed. Thus, the dose of DEMO recommended for Phase II evaluation is 1500 mg/m$^2$ BID. A maximum tolerated dose (MTD) was not established in this study.

TABLE 3

Study Safety Data: Toxicity of Oral DFMO and Etoposide

| | Maximum Grade of Toxic Effects, Cycle 1 (N = 21) | | | | Maximum Grade of Toxic Effects, Cycle 2-43 (N = 17) | | | |
|---|---|---|---|---|---|---|---|---|
| | Grade 2 | Grade 3 | Grade 4 | Grade 5 | Grade 2 | Grade 3 | Grade 4 | Grade 5 |
| Hamtologic Toxic Effects | | | | | | | | |
| Anemia | 2 (10%) | 0 | 1 (5%) | 0 | 4 (24%) | 1 (6%) | 0 | 0 |
| Neutrophil count decrease | 1 (5%) | 1 (5%) | 0 | 0 | 3 (18%) | 2 (12%) | 2 (12%) | 0 |
| Platelet count decrease | 1 (5%) | 1 (5%) | 0 | 0 | 0 | 0 | 1 (6%) | 0 |
| White blood cell decreased | 0 | 0 | 0 | 0 | 0 | 0 | 1 (6%) | 0 |
| Non-hematologic Toxic Effects | | | | | | | | |
| ALT elevation | 1 (5%) | 0 | 0 | 0 | 1 (6%) | 0 | 0 | 0 |
| Anorexia | 0 | 1 (5%) | 0 | 0 | 0 | 0 | 0 | 0 |
| AST elevation | 0 | 1 (5%) | 0 | 0 | 1 (6%) | 1 (6%) | 0 | 0 |
| Conjunctivitis | 1 (5%) | 0 | 0 | 0 | 0 | 0 | 0 | 0 |
| Constipation | 1 (5%) | 0 | 0 | 0 | 1 (6%) | 0 | 0 | 0 |
| Diarrhea | 1 (5%) | 0 | 0 | 0 | 0 | 0 | 0 | 0 |
| GGT elevation | 1 (5%) | 0 | 0 | 0 | 0 | 0 | 0 | 0 |
| Hypoalbumenia | 1 (5%) | 0 | 0 | 0 | 0 | 0 | 0 | 0 |
| Hypophosphatemia | 1 (5%) | 0 | 0 | 0 | 0 | 0 | 0 | 0 |
| Infection, sinus | 0 | 0 | 0 | 0 | 1 (6%) | 0 | 0 | 0 |
| Mouth pain | 0 | 0 | 0 | 0 | 1 (6%) | 0 | 0 | 0 |
| Nausea | 0 | 0 | 0 | 0 | 1 (6%) | 0 | 0 | 0 |
| Neuropathy | 0 | 0 | 0 | 0 | 1 (6%) | 0 | 0 | 0 |
| Pain | 0 | 0 | 0 | 0 | 1 (6%) | 0 | 0 | 0 |
| Rash | 0 | 0 | 0 | 0 | 1 (6%) | 0 | 0 | 0 |
| Sleep disturbance | 1 (5%) | 0 | 0 | 0 | 0 | 0 | 0 | 0 |
| Urinary retention | 1 (5%) | 0 | 0 | 0 | 0 | 0 | 0 | 0 |
| Vomiting | 1 (5%) | 0 | 0 | 0 | 0 | 0 | 0 | 0 |

Percentages are calculated as number of patients with an event divided by number of patients in group that received drug.
ALT = alanine aminotransferase;
AST = aspartate aminotransferase;
GGT = gamma-glutamyl transpeptidase.

Example 2—Pharmacokinetics of DFMO in Children with NB

Figure 4:
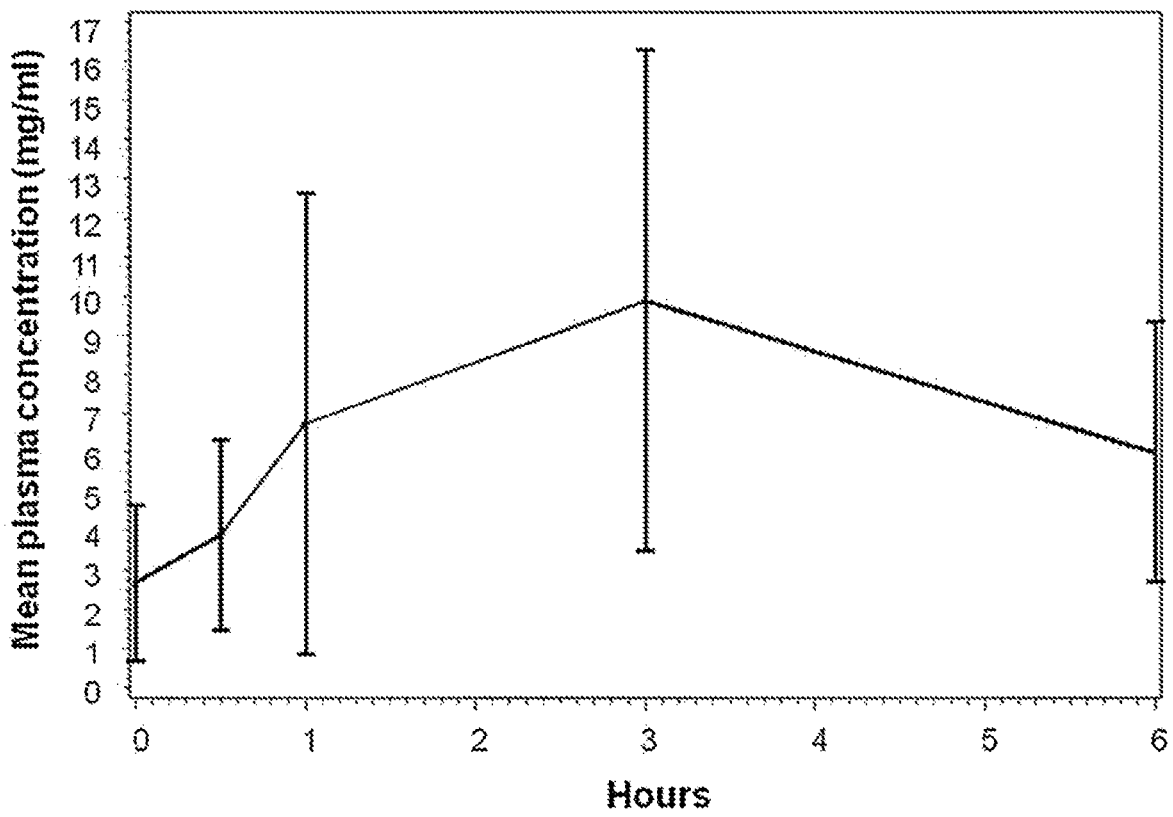
FIG. 4. Plasmsa DFMO concentration versus time measurements for three patients receiving 750 mg/m² during cycle 1 of therapy.
Figure 5:
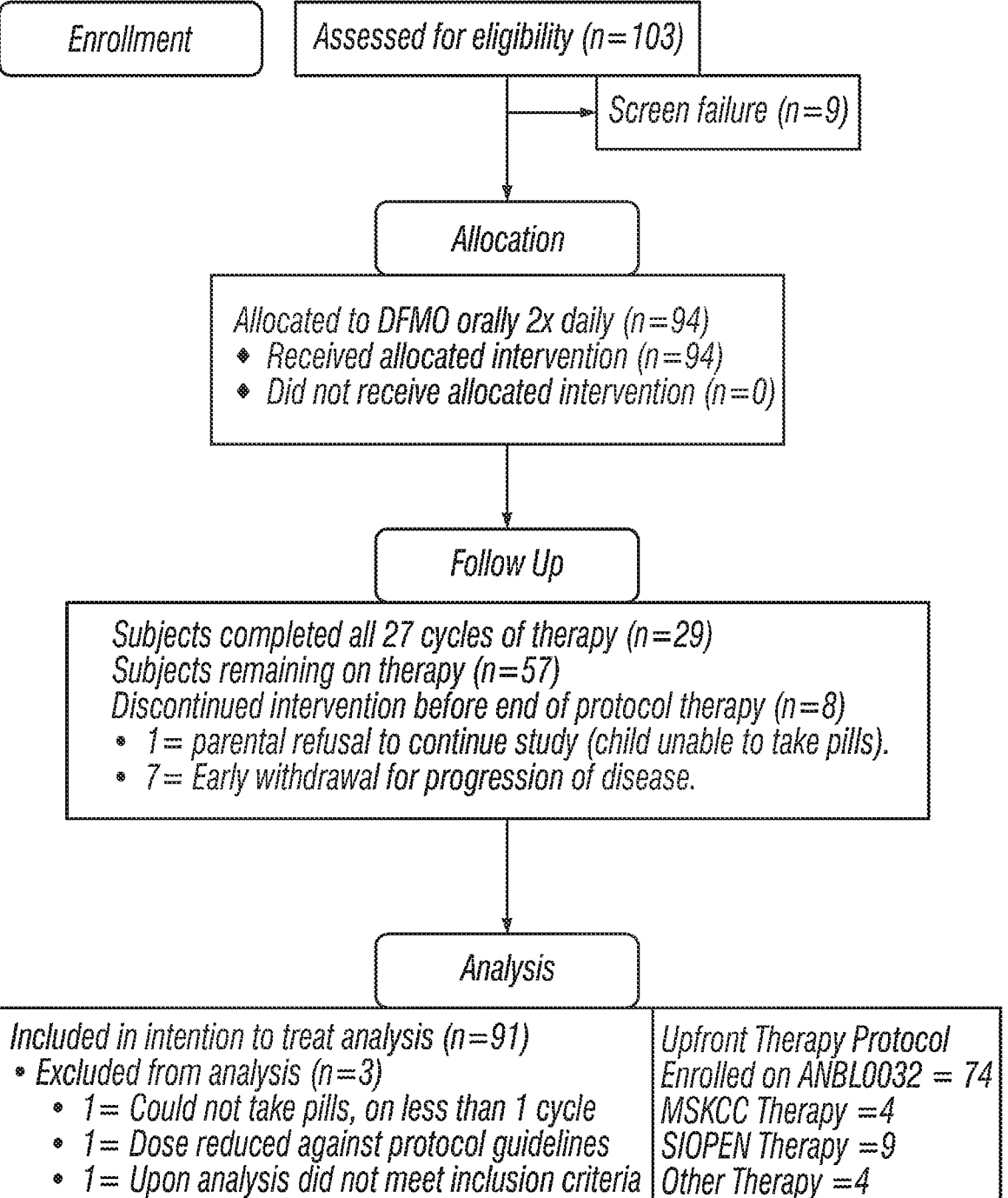
FIG. 5. NMTRC003 Stratum 1 CONSORT Flow Diagram.

DFMO serum measurements were performed in all 21 patients. Samples were collected from patients prior to, and again at times 0.5, 1, 3, and 6 hours following drug administration on days 1 and 8 of the first cycle. DFMO serum samples were also collected from selected patients in the higher dose groups (750, 1000, 1500 mg/m$^2$) during cycle 2. FIG. 4 shows the serum DFMO concentrations (mean and sd) in all patients receiving 750 mg/m$^2$ (mean±standard deviation). DFMO doses were administered orally twice daily over a 21 day cycle. Subsequent cycles commenced the day following the last day of the previous cycle. Maximum DFMO concentrations, relative to dose, are reported in Table 4. Overall average serum DFMO concentrations ranged from 9.54 μg/mL (52.24 μM) in patients receiving 500 mg/m$^2$ to 30.71 μg/mL (168.10 μM) in patients receiving 1500 mg/m$^2$. The mean t$_{max}$ occurred between 2.50 and 3.75 hours, in all dose groups. The mean AUC$_{0-6\ h}$ ranged from 39 hr-μg/mL at 500 mg/m$^2$, to 121 hr-μg/mL in the 1500 mg/m$^2$ dose group. The highest single serum concentration measured was 78.53 g/mL during cycle 1 in one patient in the highest dose group. This subject's serum levels were otherwise unremarkable when compared with the other subjects in this dose group. As seen in FIG. 4 and Table 4, there were significant variations in DFMO PK parameters among patients, possibly related to differences in dose administration time relative to sampling times, and the overall duration of sampling relative to the elimination half-life of DFMO, which is 2-4 hours in adults (Carbone et al., 2000). However, mean C$_{max}$ and AUC clearly increased in a linear fashion, in proportion to the oral doses administered, and mean t$_{max}$ was consistent across dose groups.

The PK findings in this work demonstrate that DFMO dosing in children yields serum DFMO concentrations that are very similar to those reported in adult studies, as the concentration ranges overlap, for equivalent oral doses (Pendyala et al., 1993; Carbone et al., 2000). The T$_{max}$ values observed in NB patients were also comparable to the values reported in adults (Carbone et al., 2000). The finding that clinical benefit was observed for a number of patients in this study, along with the reported efficacy of DFMO at these concentrations in adult cancer prevention studies, indicates that biologically effective doses of DFMO are in the 50-150 μM range. DFMO doses in this range do not kill NB cells (Samal et al., 2013), suggesting other mechanisms of DFMO action. One non-cytotoxic mechanism described recently is the suppression of metabolites involved in DNA synthesis (Witherspoon et al., 2013). Other non-cytotoxic mechanisms could involve inflammation (Babbar et al., 2007) and/or immune responses (Soda, 2011).

TABLE 4

DFMO pharmacokinetic parameters (mean ± SD) by dose level

| PO BID Dose (mg/m$^2$) | Cycle | C$_{max}$ (mcg/mL) mean ± SD | t$_{max}$ hours | AUC$_{0-6\ hrs}$ (mcg/mL) × hrs |
|---|---|---|---|---|
| 500 | 1 | 9.54 ± 5.36 | 3.75 ± 1.39 | 39.90 ± 24.16 |
| 750 | 1 | 11.93 ± 5.22 | 3.60 ± 1.26 | 47.36 ± 18.57 |
| | 2 | 14.23 ± 7.92 | 2.60 ± 0.89 | 62.84 ± 39.47 |
| 1000 | 1 | 14.71 ± 9.07 | 3.17 ± 1.60 | 60.05 ± 34.53 |
| | 2 | 14.33 ± 6.18 | 3.00 ± 0.00 | 50.18 ± 32.57 |

TABLE 4-continued

| DFMO pharmacokinetic parameters (mean ± SD) by dose level | | | | |
|---|---|---|---|---|
| PO BID Dose (mg/m$^2$) | Cycle | $C_{max}$ (mcg/mL) mean ± SD | $t_{max}$ hours | $AUC_{0-6\ hrs}$ (mcg/mL) × hrs |
| 1500 | 1 | 28.99 ± 14.96 | 2.88 ± 1.45 | 108.38 ± 53.23 |
| | 2 | 30.71 ± 8.18 | 2.50 ± 0.90 | 120.69 ± 31.22 |

Example 3—Rationale for Genetic and Metabolic Markers of Polyamine Metabolism and Pharmacodynamic (PD) Measures of DFMO Effect FIG. 1 depicts the polyamine metabolic pathway and highlights the relationship between ODC genotypes (rs2302615 and rs2302616), affecting ODC expression, and their relationship to urinary polyamines. The figure shows the substrate relationships for the diamine and acetylpolyamine exporter (Xie et al., 1997; Uemura et al., 2008; Uemura et al., 2010), which include putrescine, monoacetylspermidine and diacetylspermine (DAS) but not spermidine or spermine. Levels of these exported amines might be expected to reflect changes in tissue ODC expression, as polyamine export is known as one component of polyamine homeostatic regulation (Gerner and Meyskens, 2004).

First morning void spot urines from each patient were evaluated for polyamines as described in Methods. Table 5 shows data (means±SD) at baseline (cycle 1, day 1) for seven metabolites in the polyamine pathway, including putrescine, spermidine, spermine and the acetyl derivatives of spermidine and spermine. Listed in rank order in this table, N$^8$AcSpd was the most prevalent amine in the urines of these patients at baseline, followed by N$^1$AcSpd, putrescine, DAS, spermine, N$^1$-acetylspermine (N$^1$AcSpm) and spermidine. Values for each metabolite varied significantly, as indicated by the large standard deviation for each metabolite.

versus day 8, baseline versus day 15, and day 8 versus day 15). The paired comparisons show that there was a significant decline from Day 1 to 8 (P=0.018) for the N=19 patients with Day 1 and 8 data, and a significant decline from Day 1 to 15 (P=0.005) for N=16 patients with Day 1 and 15 data. No change was seen between Day 8 and 15 (P=1.000) for those N=16 patients with complete data.

A standard repeated measures analysis of variance was used to confirm the apparent changes in N$^1$AcSpd during the first two weeks of treatment. This parametric approach also used the 15 complete cases as did the paired comparisons analysis using the Friedman's test. The within subject results identify a significant linear effect (P=0.003) and a marginal quadratic effect (P=0.075). This analysis indicates that the mean values of N$^1$AcSpd decline over time with most of the decline occurring during the first week of treatment. The bending or bottoming out at Day 8 and 15 leads to the quadratic effect. This is consistent with the paired Friedman's comparisons. As was the case with the overall Friedman's test, the overall change with the univariate repeated measures model show a significant change over time (P=0.002).

Patterns of these metabolites were assessed in relationship to ODC genotypes and the treatment period to determine if changes might be associated with either genetic factors or therapy. Table 6 lists individual patients rank-ordered by PFS and includes ODC genotype and urinary polyamine contents. For simplicity, only the sum of putrescine, N$^1$AcSpd, N$^8$AcSpd and DAS, which are true substrates for the tissue polyamine exporter, are shown in Table 6. Table 7 presents results of associations of baseline and changes in urinary polyamines after one week of DFMO therapy and PFS with ODC genotypes. PFS was over 4 times greater in patients with any minor T allele, compared to GG, at rs2302616 (498 days compared to 110 days, P=0.048 by one-tailed t-test). Differences in PFS by rs2302615 were not statistically significant. The variation observed in baseline

TABLE 5

| Urinary polyamine metabolites from patients at baseline and during first two weeks of DFMO therapy | | | | |
|---|---|---|---|---|
| Polyamine | C1D1 Mean (N = 19) | Standard Deviation | P-value for decrease from C1D1 to C1D8 (N = 19)* | P-value for decrease from C1D1 to C1D15 (N = 16)* |
| N$^8$AcSpd | 4.72 | 3.18 | NS** | BS |
| N$^1$AcSpd | 3.96 | 3.18 | 0.018 | 0.005 |
| Putrescine | 1.93 | 7.02 | NS | NS |
| N$^1$N$^{12}$Ac2Spm | 0.80 | 0.62 | NS | NS |
| Spermine | 0.55 | 1.71 | NS | NS |
| N$^1$AcSpm | 0.33 | 0.74 | NS | NS |
| Spermidine | 0.26 | 0.25 | NS | NS |

C1D1 = cycle 1 day 1 (i.e., baseline);
C1D8 = cycle 1 day 8 after starting DFMO on day 1;
C1D15 = cycle 1 day 15 after starting DFMO on day 1;
*determine by Friedman two-way analysis of variance;
**not significant.

To determine if these baseline values were affected by treatment, all seven of these metabolites were evaluated for changes over the first two week period of treatment. Only N$^1$AcSpd (N=15 cases) showed a significant change over time (P=0.004 unadjusted and P=0.036 Bonferonni adjusted).

The changes in N$^1$AcSpd were then further evaluated by paired comparisons between each of the 3 days (baseline urinary polyamines seemed to be at least partially explained by ODC genotype. Levels of urinary substrates for the polyamine exporter were nearly twice as high in samples from patients with the minor T-allele, compared to those with the GG genotype, at rs2302616 (P=0.085 by two-tailed t-test). Urinary polyamines were higher for the GG genotype, compared to any A, at rs2302615, but this difference was not significant (P=0.381). The effect of DFMO treatment was more pronounced as a function of ODC genotype. Urinary polyamine levels decreased by nearly 50% from baseline values after one week of DFMO therapy in patients with the minor T allele at rs2302616, while increasing nearly 25% in patients with the GG genotype at rs2302616 (P=0.040). The effect of DFMO was also quantitatively greater in patients with the GG genotype, compared to any A allele, at rs2302615, but the difference was not statistically significant.

Urinary polyamines, especially DAS were also associated with disease progression. Urine samples were collected at intervals after baseline. For simplicity, Table 6 indicates whether DAS (or other urinary polyamine metabolites)

increased from baseline values. Data were available from 17 of 18 patients evaluable for PFS. Baseline samples were not available for one patient in this group. Total urinary polyamines (putrescine+$N^1$AcSpd+$N^8$AcSpd+DAS) increased on average 6.56±16.29 μmol/g Creatinine from baseline in patients that experienced disease progression less than 100 days after start of therapy. Urinary polyamines decreased on average 1.57±3.37 μmol/g Creatinine in patients in whom disease progression occurred after 100 days from start of therapy. Urinary DAS increased in 9/10 patients with disease progression occurring within 100 days of therapy start, but in only 1/7 patients progression free up to 100 days (P<0.01, Fisher's Exact Test).

TABLE 6

Rank-ordered PFS by DFMO dose, ODC genotype and urinary polyamines

| Patient # | PFS (days) | Best Response (CT/MIBG) | Status or Reason off study* | DFMO Dose (mg/m²) | ODC SNP rs2302615/ rs2302616 | UPA** Cycle 1 Day 1 | UPA** Cycle 1 Day 8 | DAS increase from Cycle 1 Day 1 |
|---|---|---|---|---|---|---|---|---|
| 1 | 1573 | SD/PR | Alive (PF) | 500 | GA/TG | NA*** | 15.70 | NA |
| 2 | 1559 | SD | Alive (PF) | 500 | GG/TG | 19.72 | 11.69 | No |
| 3 | 663 | SD/PR | Alive (PF) | 1500 | GG/TT | 9.00 | 5.61 | Yes |
| 4 | 418 | SD | PD | 750 | GA/GG | 2.25 | 7.80 | No |
| 5 | 239 | SD | PD | 1000 | GG/TG | 40.12 | 8.71 | No |
| 6 | 209 | (CT Neg)/PR | PD | 1500 | GA/TG | 12.23 | 3.98 | No |
| 7 | 136 | SD | $2^{nd}$ Leukemia | 1500 | GG/GG | 4.58 | 6.99 | No |
| 8 | 103 | SD | PD | 750 | GG/GG | 5.04 | NA*** | No |
| 9 | 94 | SD | PD | 500 | GG/TG | 10.18 | 4.20 | Yes |
| 10 | 67 | PD | PD | 750 | GG/GG | 26.75 | 22.08 | Yes |
| 11 | 64 | PD | PD | 1000 | AA/GG | 4.97 | 3.89 | Yes |
| 12 | 62 | SD | PD | 1500 | AA/GG | 2.85 | 3.77 | No |
| 13 | 62 | SD | PD | 1500 | GA/TG | 11.53 | 8.81 | Yes |
| 14 | 62 | SD | PD | 1500 | GA/TG | 15.35 | 7.38 | Yes |
| 15 | 59 | PD | PD | 1000 | GA/GG | 6.80 | 3.28 | Yes |
| 16 | 57 | SD | PD | 750 | GG/GG | 2.16 | 1.94 | Yes |
| 17 | 31 | PD | PD | 750 | GA/GG | 15.34 | 13.46 | Yes |
| 18 | 21 | PD | PD | 1500 | GG/TG | 7.49 | 5.93 | Yes |

*PF = progression free; PD = progressive disease, $2^{nd}$ Leukemia = secondary leukemia;

**Substrates for the tissue polyamine exporter SLC3A2 include the sum of putrescine, N1AcSpd, N8AcSpd, and DAS;

***NA = samples not available.

TABLE 7

Association of ODC genotypes with polyamine markers and treatment responses

| ODC SNP | rs2302615 | | | rs2302616 | | |
|---|---|---|---|---|---|---|
| Genotype | GG | Any A | P value | GG | Any T | P value |
| PFS | 326.7 ± 501.6 | 282.1 ± 499.6 | 0.426 | 110.8 ± 119.1 | 498.0 ± 635.4 | 0.048* |
| UPA C1D1 | 13.16 ± 12.10 | 9.15 ± 5.07 | 0.381 | 7.73 ± 7.69 | 15.18 ± 10.03 | 0.085** |
| UPA (C1D1 − C8D1)/ C1D1 × 100 | 23.26 ± 35.59 | 0.66 ± 92.00 | 0.531 | −24.46 ± 83.67 | 48.32 ± 18.24 | 0.040** |

*1 tail Student t-test;

**2 tail Student t-test;

D1C1 = day 1, cycle 1;

D8C1 = day 8, cycle 1.

Example 4—Response

Figure 2:
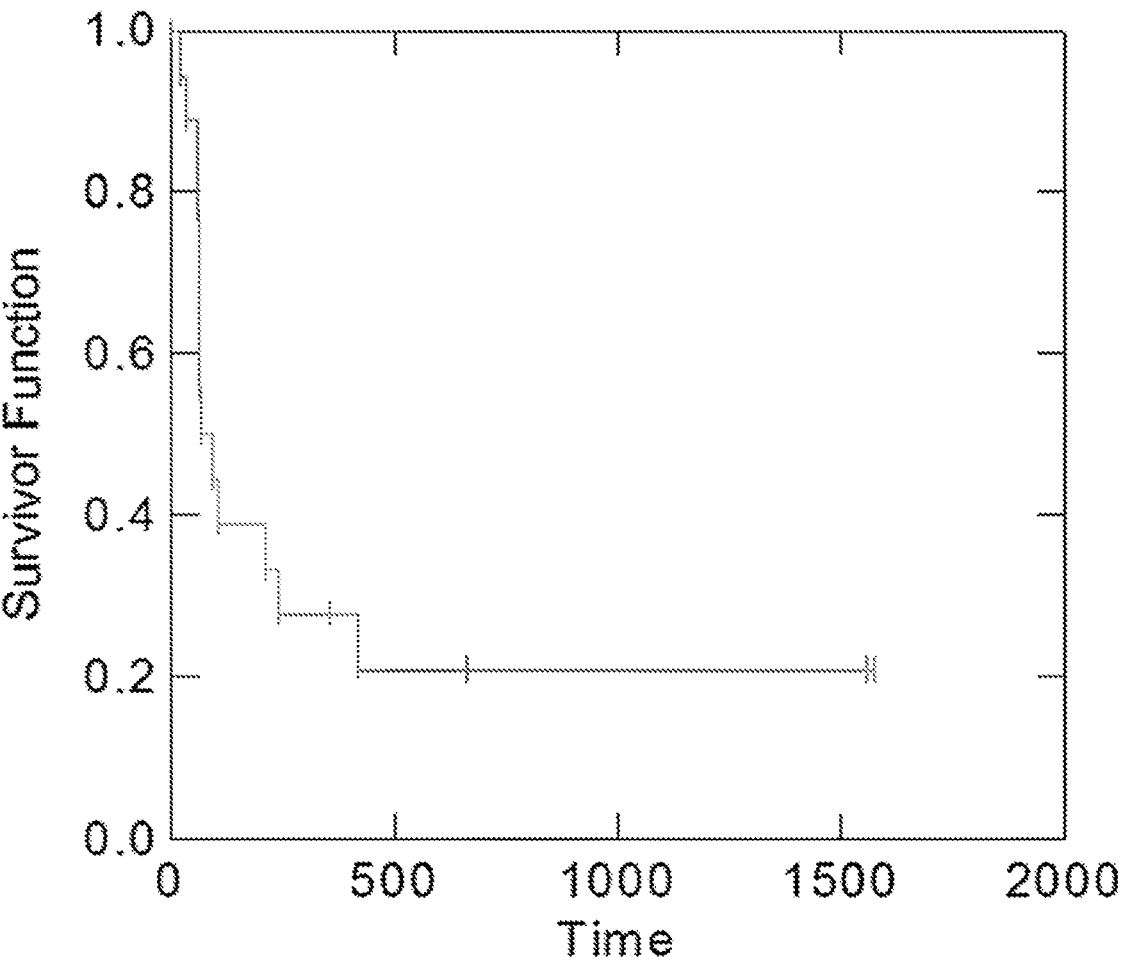
FIG. 2. Progression free survival (PFS) for all eligible patients enrolled in NMTRC 002 (N=21 with four censored [no progression]). The mean PFS=420 days.

Eighteen subjects were evaluable for efficacy following treatment. Overall response considering Response Evaluation Criteria In Solid Tumors (RECIST) criteria, MIBG evaluation and bone marrow disease showed: 1 patient had a best response of PR (MIBG evaluable disease only), 12 subjects has a best response of stable disease by RECIST (with 2 of these subjects having PR on MIBG and one subject having CR in bone marrow), and 5 had a best response of progressive disease. Three subjects who were evaluated by PET scans, two had a complete response and one a partial response, although it should be noted that PET scans were not routinely performed. These three patients are those that remain without progression on this study. PET response will be looked at in future studies. A Kaplan-Meyer plot of progression-free survival (PFS) is shown in FIG. 2. The mean progression free survival for all 18 evaluable subjects was 420 days. Three patients remain alive without progression of disease between 2-4.5 years after starting DFMO.

Some patients with the ODC risk allele did not respond to the DFMO plus etoposide therapy. Failures of therapies targeting single oncogenes may be due to resistance mechanisms arising from acquisition of other activating mutations affecting additional signaling pathways (Weinstein and Joe, 2008). Choi et al. (2014) have recently reported evidence in support of this concept. Their results suggest that DFMO combinations targeting other genetic features of NB (Pugh et al., 2013; Samal et al., 2013; Lange et al., 2014) may be beneficial to patients not responding adequately to DFMO±etoposide.

Example 5—Phase II Preventative Trial of DFMO in Patients with High-Risk Neuroblastoma in Remission ODC/polyamines present a therapeutic target for the treatment and prevention of recurrence of NB. This study will focus on the use of DFMO in high-risk neuroblastoma patients that are in remission as a strategy to prevent recurrence. This study will be conducted according to the principles of the 2004 version of the Declaration of Helsinki, the International Conference on Harmonization Guidance on Good Clinical Practice and the requirements of all local regulatory authorities regarding the conduct of clinical trials and the protection of human subjects.

An independent Data Safety and Monitoring Board (DSMB) will oversee the conduct of the study. The members of this Board will receive database summaries, including adverse event reports, and will convene either in person or via teleconference every 6 months. The Board will be responsible for decisions regarding possible termination and/or early reporting of the study.

A clinical monitor will make regularly scheduled trips to the investigational site to review the progress of the trial as defined in the Monitoring Plan. The actual frequency of monitoring trips will depend on the enrollment rate and performance at each site. At each visit, the monitor will review various aspects of the trial including, but not limited to, screening and enrollment logs; compliance with the protocol and with the principles of Good Clinical Practice; completion of case report forms; source data verification; study drug accountability and storage; facilities and staff data quality; regulatory documentation; and study integrity. In addition the site may be audited by representatives of Cancer Prevention Pharmaceuticals (CPP) and/or government inspectors who must be allowed access to CRFs, source documents and other study files. The site must promptly notify the study chair of any inspections scheduled by regulatory authorities, and also forward copies of the inspection reports to the study chair. The study chair will promptly forward this information to CPP.

During scheduled monitoring visits, the Investigator and the investigational site staff must be available to meet with the study monitor in order to discuss the progress of the trial, make necessary corrections to case report form entries, respond to data clarification requests and respond to any other trial-related inquiries of the monitor.

Patient Selection. All subjects (or patients' legal representatives) must provide written informed consent before any study specific assessments may be performed. Authorization from the patient (or patients' legal representatives) to use and/or disclose protected health information in compliance with the Health Insurance Portability and Accountability Act (HIPAA) but also be obtained.

The following screening procedures must be performed within 14 days prior to the first dose of study drug (7 days extra may be requested from the study chair in exceptional cases). Studies must be performed after last previous treatment for malignancy:

1. Signed informed consent form. All subjects (or patients' legal representatives) must provide written informed consent before any study specific assessments may be performed. Signed informed consent form for voluntary participation in correlative biologic analysis will also be obtained;
2. CT or MRI to confirm remission status;
3. MIBG scan to confirm remission status. Consider PET scan for non MIBG avid subjects;
4. Audiogram;
5. Bone marrow aspirate and biopsy;
6. Additional Optional Bone Marrow—for subjects with additional informed consent bone marrow samples for biological correlatives.

The following screening procedures must be performed up to 5 days prior to the first dose of study drug:

1. Complete medical and surgical history, including documentation of the histologic evidence of malignancy and prior treatments for cancer. Include all other pertinent medical conditions and a careful history of all prior medical treatments;
2. Demographics;
3. Physical examination (including height and weight), noting all abnormalities including baseline dermatologic and neurologic exam;
4. BSA calculation (from body weight and height);
5. Vital signs, including temperature, pulse rate, and blood pressure;
6. ECOG Performance status/Lansky Play status;
7. CBC with differential;
8. Serum electrolytes, blood urea nitrogen (BUN), creatinine, bilirubin, LDH, ALT, AST and ferritin;
9. C-reactive protein (CRP) and Erythrocyte sedimentation rate (ESR);
10. Urine for Vanillylmandelic Acid (VMA) & Homovanillic Acid (HVA);
11. Urine pregnancy test for female subjects of child bearing potential (onset of menses or ≥13 years of age);
12. Concomitant medications/therapies including documentation of steroid use and dose;
13. Confirmation of inclusion and exclusion requirements;
14. Urine for biological correlates.

Following completion of all required screening procedures and certification of all inclusion and exclusion criteria, the subject will be enrolled in the trial and a unique subject number assigned.

Inclusion criteria for the study are as follows:

1. Age: 0-21 years at the time of diagnosis.
2. Diagnosis: histologic verification at either the time of original diagnosis or a previous relapse of high-risk neuroblastoma.
3. Disease Status: Neuroblastoma that is in remission
4. Greater than 30 days from completion of cytotoxic and biologic therapy and less than 120 days from previous therapy.
5. A negative urine pregnancy test is required for female subjects of child bearing potential (onset of menses or ≥13 years of age).
6. Both male and female post-pubertal study subjects need to agree to use one of the more effective birth control methods during treatment and for six months after treatment is stopped. These methods include total abstinence (no sex), oral contraceptives ("the pill"), an intrauterine device (IUD), levonorgestrol implants (Norplant), or medroxyprogesterone acetate injections (Depo-provera shots). If one of these cannot be used, contraceptive foam with a condom is recommended.
7. ANC>500/μL and platelet count>50,000/μL.
8. Organ Function Requirements: Subjects must have adequate liver function as defined by:
   a. AST and ALT<10× upper limit of normal
   b. Serum bilirubin must be ≤2.0 mg/dl
   c. Serum creatinine based on age/gender as shown in Table 8.
9. Informed Consent: All subjects and/or legal guardians must sign informed written consent. Assent, when appropriate, will be obtained according to institutional guidelines.

TABLE 8

Serum creatinine levels based on age/gender

| Age | Maximum Serum Creatinine (mg/dL) | |
| --- | --- | --- |
| | Male | Female |
| 1 month to <6 months | 0.4 | 0.4 |
| 6 months to <1 year | 0.5 | 0.5 |
| 1 to <2 years | 0.6 | 0.6 |
| 2 to <6 years | 0.8 | 0.8 |
| 6 to <10 years | 1 | 1 |
| 10 to <13 years | 1.2 | 1.2 |
| 13 to <16 years | 1.5 | 1.4 |
| ≥16 years | 1.7 | 1.4 |

Exclusion criteria for the study are as follows:

1. Lansky score<60%
2. BSA (m²) of <0.25
3. Investigational Drugs: Subjects who are currently receiving another investigational drug are excluded from participation.
4. Anti-cancer Agents: Subjects who are currently receiving other anticancer agents are not eligible. Subjects must have fully recovered from the effects of prior chemotherapy (hematological and bone marrow suppression effects).
5. Infection: Subjects who have an uncontrolled infection are not eligible until the infection is judged to be well controlled in the opinion of the investigator.
6. Subjects who, in the opinion of the investigator, may not be able to comply with the safety monitoring requirements of the study, or in whom compliance is likely to be suboptimal, should be excluded.
7. Prior hypersensitivity to eflornithine.

All intercurrent medical conditions will be treated at the discretion of the Investigator according to acceptable community standards of medical care. All concomitant medications and treatments will be documented. The following medications are not permitted during the trial: any cytotoxic chemotherapy; any other investigational treatment; any other systemic anti-neoplastic therapy including, but not limited to, immunotherapy, hormonal therapy, targeted therapies, anti-angiogenic therapies, or monoclonal antibody therapy; and any radiotherapy, including systemically administered radioisotopes, unless administered with palliative intent. Erythropoietin, blood products, anti-emetics, steroids, and transfusions may be administered at the discretion of the Investigator based on established criteria.

Subjects may be withdrawn from the study treatment for the following reasons:

Progressive neoplastic disease

Subject or guardian withdraws consent to continue study drug

Subject develops an intercurrent illness that precludes further participation, or requires a prohibited concomitant treatment The Investigator withdraws the subject in the subject's best interests Subject is lost to follow-up (defined as the inability to contact the subject on 3 separate occasions over a period of 2 weeks)

Administrative reasons (e.g., the subject is transferred to hospice care)

An adverse event, which in the opinion of the Investigator, precludes further trial participation or fulfills the protocol requirements for withdrawal (e.g., the development of dose limiting toxicity despite a reduction in protocol therapy for a previous episode of dose limiting toxicity)

Death

Subjects may be withdrawn from the study for the following reasons:

Subject or guardian withdraws consent to continue in the trial

Subject is lost to follow-up (defined as the inability to contact the subject on 3 separate occasions over a period of 2 weeks)

Subject completes all protocol defined therapy including all follow-up time points.

Death

DFMO Treatment. In this study subjects will receive twenty-seven (27) cycles of oral DFMO (eflornithine hydrochloride designated chemically as 2-(difluoromethyl)-DL-ornithine monohydrochloride monohydrate) at a dose of 500 to 1000 mg/m² BID (per dosing chart in Table 9) on each day of a 28 day cycle. The dosage form to be used in this study will be provided as a yellow, film-coated convex tablet containing 250 mg of eflornithine HCl, monohydrate. The oral tablet form is not available outside of the clinical trial setting in the U.S., and the formulation used in this trial is similar to that used in the Phase III colon adenoma clinical trial in combination with sulindac (Meyskens et al., 2008).

Treatment will be administered on an outpatient basis unless hospitalization is required for another reason. Subjects will be advised to maintain a low polyamine diet during the duration of the study. A handout will be provided to subjects with foods they should avoid while on this study.

TABLE 9

| | DFMO Dosing | | |
| BSA (m²) | Tablets to be Dispensed for Each Dose | Total Tablets per Day | Actual mg/m² |
| --- | --- | --- | --- |
| >1.5 | Four (4) tablets orally twice a day | 8 | 625 and down per dose |
| 0.75 to 1.5 | Three (3) tablets orally twice a day | 6 | 500 to 1000 per dose |
| 0.5 to <0.75 | Two (2) tablets orally twice a day | 4 | 675 to 1000 per dose |
| 0.25 to <0.5 | One (1) tablet orally twice a day | 2 | 500 to 1000 per dose |
| <0.25 | Not eligible for trial | | |

Dose Modifications. Toxicities and dose modifications will be monitored in all cycles. Adjustments to the doses of study drug will be based upon toxicity, graded according to the NCI Common Toxicity Criteria (CTC), Version 4.0, if these were normal at baseline. Events that are not described in the NCI criteria will be assigned grades. Criteria for determining the relatedness of clinical adverse events to treatment will be utilized to determine the relationship of adverse events to the treatment.

Patients experiencing any toxicity attributable to DFMO or any intolerable toxicity will have their dose of DFMO held until toxicities have reverted to ≤Grade 2 toxicity. Upon resolution of the toxicity, subjects will receive a dose reduction of DFMO to one step down on the dosing table (Table 9). Subjects that are currently only taking one tablet per dose BID will be dose reduced to one tablet per day (QD). Subjects will be allowed to dose reduce for subsequent toxicities defined here as many times as they can until they reach the one tablet per day (QD) dosing. At that point if they experience another dose reducing toxicity they will be required to go off protocol therapy. Examples of dose reducing toxicities include: Grade 4 neutropenia or thrombocytopenia that persists for 7 days or longer after the discontinuation of study drug; >10× elevation of transaminases that persists for 7 days or longer after the discontinuation of study drug; any other Grade 3 non-hematologic toxicity, excluding alopecia, nausea, vomiting, and diarrhea that does not adequately respond to treatment. If there is no resolution of an above toxicity by 14 days, DFMO should be discontinued, and subjects should be discontinued from the study. For patients entering this trial with platelets less than 100,000/μL (those with poor bone marrow recovery after previous treatment), study drug should be held if platelets fall below 50% of the baseline value.

Response Evaluations. Scans will be obtained at various time points to evaluate response for subjects enrolled in this study. Response will be assessed according to set criteria to evaluate the potential benefit of DFMO in this patient population.

Treatment Phase—Cycle 1. The first cycle will be 28 days in duration. The following procedures must be completed on Cycle 1 Day1 (may be performed up to 5 days prior to DFMO administration unless otherwise indicated):

1. Physical examination (including body weight), including documentation of an update of all previous abnormalities, any new abnormalities, and a detailed neurological exam
2. Vital signs, including temperature, pulse rate, blood pressure (sitting) (to be done on Cycle 1 Day 1);
3. Review and recording of concomitant medications; (to be done on Cycle 1 Day 1)
4. Monitoring and documentation of all AEs and review of concurrent illnesses (to be done on Cycle 1 Day 1)

5. Urine for Biological Correlates (to be done on Cycle 1 Day 1 in addition to the screening sample)
6. Optional: Blood for biological correlates (additional consent required)
7. Dispense drug dosing diary The following evaluations will be performed on Cycle 1 Day 15 (+/−3 day window):

1. Physical exam
2. Vital signs, including temperature, pulse rate, and blood pressure (sitting)
3. CBC with differential;
4. Serum electrolytes, BUN, creatinine, bilirubin, ALT, AST; and LDH
5. Review and recording of concomitant medications;
6. Monitoring and documentation of all AEs and review of concurrent illnesses
7. Urine for biological correlates
8. Optional: Blood for biological correlates (additional consent required)

Treatment Phase—Cycles 2-27. All Cycles will be 28 days in duration. The following procedures must be completed on Cycle 2-27 Day 1 (may be performed up to 5 days prior to starting treatment):

1. Physical examination (including body weight), including documentation of an update of all previous abnormalities, any new abnormalities, and a detailed neurological exam
2. Vital signs, including temperature, pulse rate, blood pressure (sitting);
3. Review and recording of concomitant medications;
4. Monitoring and documentation of all AEs and review of concurrent illnesses
5. BSA calculation (from body weight and height);
6. ECOG Performance status/Lansky Play status;
7. CBC with differential;
8. Serum electrolytes, blood urea nitrogen (BUN), creatinine, bilirubin, LDH, ALT, and AST;
9. C-reactive protein (CRP) and Erythrocyte sedimentation rate (ESR)
10. Urine for Vanillylmandelic Acid (VMA) & Homovanillic Acid (HVA)
11. Urine for biological correlates
12. Optional: Blood for biological correlates (additional consent required)
13. Collection of previous cycle drug dosing diary and dispensing of new drug dosing diary
14. Urine pregnancy test for female subjects of child bearing potential (onset of menses or ≥13 years of age).

End of Cycles 3, 6, 9, 12, 15, 18, 21, 24, 27 and then per institutional standard of care for follow-up:

1. MIBG scan (for MIBG avid subjects only). Consider PET scan for non MIBG avid subjects.
2. CT/MRI (use same radiologic method as baseline)

3. Bone marrow biopsy and aspirate is to be performed if the treating physician has concerns for progression 4. Optional: Blood for biological correlates (additional consent required). This may be performed up to or on Day 1 of the next cycle.

At the end of Cycles 6, 12, and 27, an audiogram will be taken. Audiogram should also be performed at any time point for any suspected hearing loss.

Additional imaging or assessments may be done if clinically indicated. Type of imaging, type of assessment, and timing should be recorded as well as reason for imaging and/or assessment. Survival will be monitored on an ongoing basis during the study, then every 3 months from the time the subject is off-treatment for a period of 2 years, then yearly for up to five years or until subject death or subject is lost to follow up. Subjects who receive 27 total 28-day treatment cycles will be considered as having completed the protocol.

Off Therapy/30 Day follow-up visit evaluations will be conducted as follows:

1. Physical examination (including body weight), including documentation of an update of all previous abnormalities, any new abnormalities, and a detailed neurological exam;

2. ECOG Performance status/Lansky Play status;

3. Vital signs, including temperature, pulse rate, blood pressure (sitting);

4. CBC with differential;

5. Serum electrolytes, BUN, creatinine, bilirubin, LDH, ALT, AST;

6. C-reactive protein (CRP) and Erythrocyte sedimentation rate (ESR)

7. Urine for Vanillylmandelic Acid (VMA) & Homovanillic Acid (HVA)

8. Urine pregnancy test for female subjects of child bearing potential (onset of menses or ≥13 years of age);

9. Review and recording of concomitant medications;

10. Monitoring of AEs and review of concurrent illnesses

11. Collect previous cycles drug dosing diaries

12. MRI/CT; MIBG scan; if not already obtained within the previous three cycles. Consider PET scan for non MIBG avid subjects;

13. Bone marrow biopsy and aspirate (only if concern for progression);

14. Audiogram (if clinically indicated).

Adverse Events. Adverse events, regardless of suspected cause, will be collected for 30 days following the last dose of DFMO and until all current adverse events have resolved to baseline or ≤grade 2 (per Common Terminology Criteria for Adverse Events [CTCAE] version 4.0). Any subject with a suspected study drug-related toxicity at a follow-up visit must be followed until all current adverse events have resolved to baseline or ≤Grade 2. This may require additional clinical assessments and laboratory tests. Subjects that have started a new anti-cancer treatment since going off DFMO will be censored from any further AE collection at the date of starting the new therapy.

An adverse event is any untoward medical occurrence in a patient or clinical investigation subject administered a pharmaceutical product and which does not necessarily have to have a causal relationship with this treatment. An adverse event can therefore be any unfavorable and unintended sign (including an abnormal laboratory finding, for example), symptom, or disease temporally associated with the use of a medicinal product, whether or not considered related to the medicinal product. An untoward medical event which occurs outside the period of follow-up as defined in the protocol will not be considered an adverse event unless related to study drug. Worsening of a medical condition for which the efficacy of the study drug is being evaluated will not be considered an adverse event.

An unexpected adverse event is one for which the nature or severity of the event is not consistent with the applicable product information, e.g., the investigator's brochure. A serious adverse event is any untoward medical occurrence that at any dose:

Results in death

Is life-threatening (an event in which the patient was at risk of death at the time of the event; it does not refer to an event which hypothetically might have caused death if it were more severe)

Requires in-patient hospitalization or prolongation of existing hospitalization

Results in persistent or significant disability/incapacity

Is a congenital anomaly or birth defect

Other important medical events that may not be immediately life-threatening or result in death or hospitalization but may jeopardize the patient or may require intervention to prevent one of the other outcomes listed above. Examples of such events are intensive treatment in an emergency room for allergic bronchospasm; blood dyscrasias or convulsions that do not result in hospitalization; or development of drug dependency or drug abuse.

The term "severe" is often used to describe the intensity (severity) of an event; the event itself may be of relatively minor medical significance (such as a severe headache). This is not the same as "serious", which is based on patient/event outcome or action criteria usually associated with events that pose a threat to a patient's life or functioning.

Biological Studies. These studies will evaluate the level of polyamines and inflammatory markers in urine (first morning void urine samples will be collected on Days 1 and 15 of Cycle 1 and on Day 1 of Cycles 2-27). Subjects may voluntarily participate in additional correlative biological studies to evaluate the level of polyamines and inflammatory markers in blood (whole blood samples will be collected at enrollment; on Days 1 and 15 of Cycle 1; on Day 1 of Cycles 2-27; and at the end of Cycles 3, 6, 9, 12, 15, 18, 21, 24, and 27). These voluntary studies will evaluate microRNA levels in blood and ODC activity in white blood cells. They will also evaluate minimal residual disease in bone marrow. These biologic studies will be analyzed to identify molecular determinants of response to therapy and/or biomarkers to help guide future therapy.

Decarboxylated S-adenosylmethionine (dcSAM). Adenine and its derivatives are known to react with 2-chloroacetaldehyde to form highly fluorescent tricyclic derivatives. This reaction gives a sensitive and specific method for measuring de-SAM in urine and plasma samples. The reaction mixture will be incubated at 40° C. overnight. An aliquot of this mixture will be injected onto an Altex Ultrosphere column for chromatographic separation. Detection will be accomplished using a Perkin-Elmer LS-4 spectrofluorometer, as described by others (Haegele et al., 1987).

Polyamines. High performance liquid chromatography (HPLC) and other methods will be used, as per previous studies (Harras, 1996; Haegele et al., 1987), to detect putrescine, spermidine, spermine, monoacetylspermidine and monoacetylspermine and diacetylspermine. Samples will be adjusted to 0.2 N perchloric acid and analyzed directly. Acid hydrolysis methods will be employed to remove acetyl groups, and thus measure diacetylated amines. The detection level will be 1-10 pmol. Sources of error associated with these measures in colonic tissue have been previously reported (Hixson et al., 1994). Urinary creatinine levels will also be determined, using a commercial kit (Oxford Biochemical Research), to normalize urinary polyamines. In the method, picric acid reacts with creatinine and other urinary nm at alkaline pH. The creatinine reaction degrades rapidly when acidified. The difference in optical density is a direct measure of the creatinine concentration.

ODC SNP Analysis. The ODC G316A single nucleotide polymorphism (SNP) was associated with polyamine contents in prostate and colorectal mucosal biopsies. The lowest levels of polyamines are found in colorectal mucosal tissues from individuals homozygous for the A allele, with highest levels observed among carriers of the GG-genotype. There is no relationship between ODC G316A allele genotype and colorectal content of histamine, an amine not dependent on ODC for its synthesis. The effects of DFMO treatment on polyamine levels in patients with each ODC genotype will be determined. Ototoxicity associated with DFMO therapy is restricted to a small fraction of people with the ODC316AA genotype. These clinical trial results are corroborated by clinical translational studies that are based on molecular epidemiology investigations and have been replicated by three independent groups in humans showing that a polymorphism affecting the expression of ODC, the DFMO target protein, is highly associated with metachronous colon adenomas and sporadic breast cancer. In addition, two independent groups have reported that this same polymorphism is associated with prostate cancer progression and colon cancer survival. In order to develop algorithms predicting who will benefit, and who will have side effects of DFMO treatment, the ODC G263T and G316A types of all study participants will be determined by analyzing DNA obtained from nucleated blood cells using established methods. The levels of micro RNAs in serum (Gilad et al., 2008) will also be assessed as predictive markers of DFMO effect.

Biomarker Analysis. Subject biomarkers will be evaluated in blood plasma using antibody array analysis. Antibody arrays will be generated to target biomarker candidates derived from gene expression, proteomic, and glycomic studies of tumor tissue (obtained from related biological studies). These arrays will be used to quantify the various protein levels in order to identify proteins or panels of proteins that differentiate patients with poor prognosis from patients with good prognosis. Specific carbohydrate levels also will be characterized on each protein to determine the associations of those measurements with prognosis.

Circulating Tumor Cell Analysis. Circulating tumor cells (CTC) are emerging as novel tools in the detection and prognosis of several types of metastatic cancers. At present, CTC markers are limited to epithelial cancers and there are no specific markers available to detect mesenchymal and epithelial-mesenchymal transformed (EMT) CTCs. Utilizing a cell surface marker for detection of mesenchymal CTC, CTCs will be enumerated and isolated to aid in the early detection of tumors, metastasis, and relapse, which will contribute to the development of specific targeted therapies. The samples thus collected will be utilized to monitor the therapeutic outcome in patients.

Bone Marrow. Immunophenotyping of bone marrow samples using six-color analysis of the CD81 (PEdye), NCAM antigen CD56 (APC dye), CD9 (perCP-Cy5.5 dye) and possible stem cell antigen CD34 (PE-CY7 dye) and the absence of leukocytic antigen CD45 (APC-Hy dye) will be performed for evaluation of minimal residual disease present in bone marrow.

Statistical Analysis. The following data sets will be used in this study:

All enrolled and eligible subjects (ITT) population: All eligible subjects who have a signed informed consent form.

All treated and eligible subjects (Safety evaluable) population: All subjects who received at least one dose of study drug All eligible subjects treated to first evaluable time point with evaluation completed (generally 3 cycles) (as Treatment Efficacy) population, unless subjects have reached the study endpoint of progression of disease at an earlier time point.

Efficacy analyses will be performed on the Treatment evaluable population. Safety analysis will be performed on the Safety and Efficacy evaluable population. All baseline patient characteristics will be summarized. Safety data will be described for all subjects receiving at least one dose of DFMO. Safety data will include values for hematology, serum chemistry, vital signs, and adverse events. The proportion of subjects experiencing adverse events, serious adverse events, dose limiting toxicities and treatment delays will be summarized. Enrollment to study will not pause at interim analysis time points.

The event free survival (EFS) is defined as the period from the first day of administration of study drug until the first occurrence of relapse, progressive disease, secondary cancer, death or, if none of these events occurred, until the last contact with the subject. Progression is defined as the appearance of any new lesions>10 mm on CT/MRI, any new lesions on MIBG, or new disease present in the bone marrow. Overall survival (OS) will be defined as the first day of administration of study drug until death or will be censored at the last contact with the subject if death did not occur during the study. Overall survival will be monitored on an ongoing basis during the study, then every 3 months from the time the subject is off-study treatment up to a period of 2 years, then yearly for up to five years total.

Sample Size and Analysis—Stratum 1. A 70% 2-year EFS rate was selected as the Phase I baseline rate. The baseline 70% EFS rate at 2-years was based upon published data by Yu et al. (2010). It is hypothesized that DFMO will increase the 2-year EFS rate to 80% which represents an approximately 10% increase in the duration of the EFS rate at 2-years. Assuming a directional 5% one population binomial test, a sample size of n=127 patients will be required to achieve an 80% power to detect this 2-year difference in EFS (70% vs 80%).

The comparison of the biomarker prevalence rates assumes that the Stratum 1 cohort will experience a relapse rate of 30% and thus a 70% non-relapse rate at up to two years of follow-up. It is also assumed that the corresponding prevalence of an elevated biomarker will be 60% for the relapse group and 30% in the non-relapse group, respectively. This hypothesized prevalence difference will be detectable with 85% power with an overall sample size of N=127 patients (38 relapse and 89 non-relapse) using a Fisher's Exact Test and a non-directional Type I Error level of 5%.

The sequential biomarker data over the course of treatment for each patient will be classified as elevated or not based upon the following a priori study criteria and blinded to patient progression status. Elevation of the biomarker is defined as diacetylspermine levels>500 nmol/gm creatinine on 2 consecutive urine levels. The biomarker prevalence rates for the patients who progress (estimated to be n=38) and those who do not progress (estimated n=89) over the two years of the trial treatment will be compared using a Fisher's exact test of the equality of the two EFS prevalence rates implemented with a 5% two-tailed Type I error level. A 95% exact confidence interval for the absolute difference in prevalence rates along with a 95% exact confidence interval for the odds ratio for the resulting prevalence rates will be obtained to complement the formal hypothesis testing. Since OS will also be a secondary outcome for comparing the utility of the biomarker prevalence, time-to-event analyses will also be implemented using the Kaplan-Meier approach initially using the a priori biomarker definition. These initial time-to-event analyses will then be supplemented with a Cox proportional hazard modeling effort using the quantitative biomarker assessment to allow for an exploratory analysis of other cut-point definitions that can be used to contrast with that of the original a priori definition. Potential confounding clinical measures that are identified for the recurrent and non-recurrent patients will be incorporated in a limited fashion using Cox proportional hazard models that also include the biomarker effect. This exploration of confounders will need to be limited due to the anticipated small sample sizes. Data from this stratum will guide the statistical design for a Phase II study in this patient population.

Sample Size and Analysis—Stratum 2. Based upon tabled median EFS times all patients presented by Santana et al. (2008) for first and second recurrence times, a median first recurrence time of 8.7 months is equivalent to a 14.8% EFS at two years, and the median time to a subsequent second recurrence of 3.8 months is equivalent to an EFS rate of 1.3% at two years assuming an exponential time-to-event model. Assuming that two thirds of the relapse patient population will have had only a single relapse and that the other third of the patients will have had two or more relapses, then a weighted average of these two EFS rates (14.8% and 1.3%) equals 10.3%. A 10% historical EFS rate for two years was assumed for simplicity. Examination of an increase in EFS will require a sample size of n=33 subjects in Stratum 2 to test whether treatment with DFMO can prolong the overall estimated EFS at two years to 30% from the 10% two years estimate for the above historical data in this patient population. The sample size is based upon a one sample binomial test of proportions with a power 80% and a 5% two-tailed Type I error level.

An observation of 7 or more patients with at least a two year EFS rate out of the n=33 patients will result in the rejection of the null hypothesis of a 10% EFS in favor of the alternative of a 30% two year EFS rate. An exact binomial 95% confidence interval for the two year estimated EFS will complement the prior formal two-stage hypothesis test. Since the actual EFS time-to-event data is derived from the times to recurrence, a Kaplan-Meier analysis of the time-to-event data analysis will be conducted, and the median time to recurrence and a 95% confidence for this value will be obtained to supplement this EFS point estimate. Since this group of Stratum 2 patients will consist of patients with prior single and multiple recurrence histories, EFS and time to event data will be examined by prior recurrence histories. In particular, the impact of prior recurrence history on the time to recurrence will be explored using Kaplan-Meier analysis and Cox proportional hazard models. The response to DFMO therapy and subsequent recurrences will also be explored in combination with prior recurrence histories using Cox models.

Example 6—Pain Reduction by Eflornithine During Immunotherapy in Children Undergoing Treatment for Neuroblastoma Preclinical studies will be performed to determine if DFMO can reduce anti-GD2 induced allodynia in a rat model (Slart et al., 1997; Sorkin et al., 2002; Sorkin et al., 2010) as well as to determine the anti-tumor effects of DFMO+anti-GD2 in a murine syngeneic neuroblastoma model (Weiss et al., 1997). These preclinical studies will investigate DFMO doses from 0.15-1% in the drinking water for rodents, which corresponds to doses of 0.5-3.5 $gm/m^2$ PO BID in humans.

Clinical studies will be performed with the primary objective being to determine if DFMO as a single agent can reduce measures of pain in children with high risk neuroblastoma (HR-NB) undergoing immunotherapy without reducing (and preferably enhancing) markers of therapeutic efficacy. The study will be a double-blinded randomized study for pediatric and young adult patients with neuroblastoma that are undergoing treatment with anti-GD2 antibodies in combination with active DFMO or placebo DFMO. DFMO is an oral agent that will be administered daily at a $mg/m^2$ dose to be determined, rounded to nearest 250 mg DFMO tablet. Efficacy and pain/toxicity endpoints would be assessed at the end of X (X=1 or 5) 4 week cycle(s) of immunotherapy. Efficacy endpoint: on day 15 of the first cycle in ≥80% of patients, an increase of 500% and/or an absolute minimum increase to ≥100 cells/μl of CD16/CD56 positive NK cells and a measureable ch14.18/CHO level of at least 1 μg/ml. Pain-toxicity endpoint: i.v. morphine free ch14.18/CHO infusion schedule after the first 5 days during the first cycle in ≥80% of patients (Kushner et al., 2011). Patients will be assessed for pain using a numerical score of 1-10 over the course of treatment to generate a curve of pain intensity over time for each patient (Silvestri et al., 2008).

The study will be a Phase III trial of oral DFMO alone versus placebo in patients with high-risk neuroblastoma during maintenance treatment with immunotherapy. The primary endpoints will be assessed in a blinded manner after randomization to DFMO/placebo arms at the end of maintenance therapy with antibody (five 4-week cycles). Treatment duration will be daily DFMO for each cycle of immunotherapy. As the pain issue is especially problematic during the first cycle, the trial may be designed as only a single—the first—4 week cycle.

Secondary objectives of the clinical study include determining if this treatment can prolong event free survival (EFS) or overall survival (OS), determining the safety and tolerability of DFMO as a single agent in pediatric and young adult patients with high-risk neuroblastoma when added to standard maintenance therapy, and evaluating biological correlates, including genetic variability in the DFMO target gene ODC1 (germline single nucleotide polymorphisms [SNPs] rs2302615 and rs2302616) and levels of urinary and/or serum metabolites (putrescine, $N^1,N^{12}$-diacetylspermine, $N^1$ and $N^8$ monoacetylspermidine, decarboxylated S-adenosylmethionine, thymidine), that have been associated with disease prognosis or treatment responses. Secondary endpoints include OS, safety, germline ODC genotypes, and urinary polyamine metabolites.

Example 7—Results of a Phase II Preventative Trial of DEMO in Patients with High-Risk Neuroblastoma in Remission: DFMO Prevents Relapse and Increases Overall Survival in High Risk Neuroblastoma Study Design. This was an open label, single agent, multicenter clinical trial for patients with high-risk neuroblastoma in complete remission at the completion of standard therapy. Patients were enrolled onto the Neuroblastoma and Medulloblastoma Translational Research Consortium (NMTRC) 003/003B trial beginning in June 2012 and ending in February 2016. This trial was approved by the Western Institutional Review Board as well as by local Institutional Review Boards at each enrolling site. Prior to study entry, written informed consent was obtained from the subjects' parent(s) or guardian(s) and, when appropriate, written assent was obtained from subjects. ClinicalTrials.gov Identifiers: NCT01586260/NCT02395666.

Subjects were required to have histologically confirmed International Neuroblastoma Staging System (INSS) high-risk neuroblastoma at the time of diagnosis. Subjects must have completed standard high-risk neuroblastoma (HRNB) therapy with 5-7 cycles of induction chemotherapy, surgical resection of primary tumor (if feasible), consolidative therapy with high-dose chemotherapy/autologous stem cell support and radiation therapy as indicated, and anti-GD2 antibody therapy with isotretinoin for up to 6 cycles. Other eligibility criteria included: age at diagnosis under 21 years; disease status of complete remission at the end of upfront therapy; less than 120 days from completion of previous therapy until initiation of DFMO; and adequate hematologic parameters and organ function. To be considered in complete remission, subjects had to have no radiographic evidence for persistent neuroblastoma by CT or MRI (and by metaiodobenzylguanidine (MIBG) in subjects whose tumors were originally MIBG avid), histologically negative bone marrow aspirate/biopsy, and normal urinary catecholamines as assessed by ratios of vanillylmandelic acid and homovanillic acid to creatinine. Subjects with residual masses or bone changes visible on CT or MRI could still be considered in CR if the lesions were negative by both MIBG and PET scans.

Subjects received twenty-seven (27) 4-week cycles of oral DFMO at a dose of 500 to 1000 mg/m$^2$ twice daily. Dosing diaries were required to be completed for each cycle. DFMO was provided as 250 mg tablets. The primary endpoint was Event Free Survival (EFS); secondary objectives included Overall Survival (OS) and safety. EFS was defined as the period from the first day of administration of study drug to the first occurrence of relapse or death, and OS was defined as the first day of administration of study drug until death; subjects without an event were censored at the time of last contact. Safety analysis was conducted on all subjects who received at least one dose of study drug, and included the frequency, grading, expectedness and attribution of all adverse events as well as dose interruptions, dose reductions, and treatment discontinuation.

Statistical Analysis: Estimation and hypothesis testing based on survival data. Event-free and overall survival were estimated using the method of Kaplan and Meier (Meier, 1958) while standard errors were estimated using Greenwood's formula. The NMTRC003 population overlaps the ANBL0032 population with the majority of patients (74/94) on NMTRC 003 also enrolled and treated on ANBL0032, suggesting that published ANBL0032 results provide for a formal evaluation of the DFMO treatment effect. The work of Yu et al. (2010) provides failure times as well as numbers of patients at risk at one-year intervals; censor times were sampled based on these data and a piecewise constant hazard model was employed. However, NMTRC003 patients enrolled on ANBL0032 represent a subset of the ANBL0032 population, patients event-free at the start of NMTRC003 therapy (6-10 months after the start of ANBL0032 therapy) (Yu et al., 2010). Therefore, it was necessary to adjust the published ANBL0032 EFS using the definition of conditional probability for a direct comparison. Comparison with published ANBL0032 overall survival, however, requires an understanding of the bivariate survival distribution that is not available in the published marginal survival distributions. NMTRC003 overall survival was compared with ANBL0032 overall survival using both a formal upper bound on the non-parametric estimate and on a parametric model of the bivariate observations.

Comparison of event-free and overall survival between NMTRC003 and ANBL0032. Yu et al. (2010) reported event-free survival, $S_E$, and overall survival, $S_D$ for the ANBL0032 population, which overlaps the NMTRC003 population. For a direct comparison in the common population, ANBL0032 event-free and overall survival distributions conditional on NMTRC003 enrollment criteria ($S'_E$ and $S'_D$, respectively) were used. First, an estimate of $S'_E$ based on the definition of conditional probability is described. Since NMTRC003 enrollment requires event-free survival from the beginning of ANBL0032 treatment to the beginning of NMTRC003 treatment, a comparison of overall survival requires some understanding of the bivariate (event time, death time) survival distribution. Second, a model-independent upper bound on $S'_D$ was developed. On the one hand this provides for model-independent comparison. On the other hand, the result is unnecessarily conservative at short times. Third, a bivariate model of ANBL0032 results that provides for estimation of $S'_D$ was developed.

The sample of the ANBL0032 population described by Yu et al. (2010) is referred to as 'ANBL0032/NEJM,' which includes observations of a bivariate random variable comprising time of the first cancer event and time of death. Unprimed survival distributions ($S_E$, $S_D$) reflect the ANBL0032/NEJM population while primed random survival distribution ($S'_E$, $S'_D$) reflect the common population. t, t', $t_0$ and τ represent time from start of ANBL0032 therapy, time from start of NMTRC0032 therapy, a time from start of ANBL0032 therapy that captures the start of NMTRC003 therapy (t=t'+$t_0$), and an integration variable for time. Pr[X] is the probability of X. Pr[X|Y] is the conditional probability of X given Y.

The marginal survival function for D is $$S_D(t) = Pr[D > t] = \int_0^\infty Pr[E = \tau]Pr[D > t|E = \tau]d\tau.$$

The events are sequential and are therefore constrained by Pr[D>t|E>t]=1 (cancer death cannot precede the first cancer event). Therefore, $$S_D(t) = \int_0^t Pr[E = \tau]Pr[D > t|E = \tau]d\tau + Pr[E > t]$$

Numbers of subjects at risk and times of progression and death were taken from Yu et al. (2010; FIGS. 2A and 2B, respectively). Censor times were sampled based on a piecewise constant hazard model estimated from these at risk counts and failure times.

Estimate of $S'_E$:

When t≥$t_0$, from the definition of conditional probability, $$S'_E(t, t_0) = Pr[E > t|E > t_0] = \frac{Pr[E > t]}{Pr[E > t_0]} = \frac{S_E(t)}{S_E(t_0)}$$

Upper Bound on the Estimate of $S'_D$:

We are interested in a conditional overall survival function, $S'_D(t')=Pr[D>t'+t_0|E>t_0]$. Since $t_0$ partitions the D sample space, from the law of total probability $$Pr[D > t] = Pr[E \le t_0]Pr[D > t|E \le t_0] + Pr[E > t_0]Pr[D > t|E > t_0]$$

one gets, when $$Pr[D > t|E > t_0] =$$

$$\frac{Pr[D > t] - Pr[E \le t_0]Pr[D > t|E \le t_0]}{Pr[E > t_0]} < \frac{Pr[D > t]}{Pr[E > t_0]} = \frac{S_D(t)}{S_E(t_0)}$$

To summarize, $$S'_D(t') < \frac{S_D(t)}{S_E(t_0)}$$

The upper bound accommodates the possibility that all patients who experienced an event by to and were alive at to might in principle have died by t (that is, $Pr[E \le t_0]Pr[D>t|E \le t_0]=0$). Note that the upper bound is not a confidence limit and that it is subject to statistical uncertainty. It simply tells us that, had Yu et al. reported an estimate of $S'_D(t')$ then it would fall below $S_D(t)/S_E(t_0)$. Also note that this estimate is very conservative at times close to $t_0$.

Model for the Distribution of (E, D):

EFS was modeled using a mixture of two types of subjects, those who will not have events (proportion F among all patients) and those having exponentially distributed events with hazard $\alpha$, $$Pr[E > t] = F + (1 - F)e^{-\alpha t}$$

or, equivalently, $$Pr[E = t] = \frac{-dPr[E > t]}{dt} = \alpha(1 - F)e^{-\alpha t}$$

OS was modeled as a mixture based on two types of patients differing by death hazard, $\beta_1$ vs $\beta_2$, $$Pr[D > t|E = \tau] = \rho e^{-\beta_1(t-\tau)} + (1 - \rho)e^{-\beta_2(t-\tau)}$$

Substituting these into Eq. 1 and integrating one gets $$Pr[D > t] =$$

$$\alpha(1 - F)\left[\frac{\rho(e^{-\beta_1 t} - e^{-\alpha t})}{\alpha - \beta_1} + \frac{(1 - \rho)(e^{-\beta_2 t} - e^{-\alpha t})}{\alpha - \beta_2}\right] + F + (1 - F)e^{-\alpha t}$$

Indeterminate forms are determined using L'Hopital's rule, for example, when $\alpha=\beta_1=\beta_2$ $$Pr[D > t] = F + (1 - F)(1 + \alpha t)e^{-\alpha t}$$

NMTRC003 overall survival under the null hypothesis, $S'_D(t)=Pr[D>t|E>t_0]$, is then $$S'_D(t') = \frac{\rho\alpha(1 - F_{t_0})}{\alpha - \beta_1}(e^{-\beta_1 t'} - e^{-\alpha t'}) + \frac{(1 - \rho)\alpha(1 - F_{t_0})}{\alpha - \beta_2}(e^{-\beta_2 t'} - e^{-\alpha t'}) +$$

$$F_{t_0} + (1 - F_{t_0})e^{-\alpha t'}$$

where $$F_{t_0} = \frac{F}{F + (1 - F)e^{-\alpha t_0}}$$

Patient Characteristics. Consent was obtained from 103 HRNB patients at 20 clinical sites across US, with 94 eligible for treatment. Of these, all 94 received drug and were eligible for safety analysis, and 91 were eligible for ITT analysis. Although subjects received a variety of standard upfront treatment regimens, including those from the Children's Oncology Group (COG), Memorial Sloan Kettering Cancer Center (MSKCC), and the International Society of Pediatric Oncology Europe Neuroblastoma (SI-OPEN), within the ITT population a total of 74 subjects had previously enrolled and completed therapy on COG ANBL0032.

Due to dosing constraints resulting from a tablet size of 250 mg, a dosing table was used with actual prescribed doses varying between 500-1000 mg/m²/dose, with a mean dose of 789 mg/m². All patients but one received at least 80% of all prescribed doses.

High risk features of our patient population, including MYCN amplification, ploidy, histology, and response to induction therapy, matched those reported in the ANBL0032 study population (Yu et al., 2010). While all subjects received some combination of standard therapies, 15% (14/91) of subjects had a suboptimal response to initial therapy and required additional therapies to obtain remission.

TABLE 10

| Patient characteristics. | | |
|---|---|---|
| Characteristics | | Stratum 1 |
| Mean Age | | 4.5 |
| Sex | Male | 51 |
| | Female | 43 |
| Ethnicity | White | 67 |
| | Black or African American | 6 |
| | American Indian/Alaska Native | 2 |
| | Hispanic | 10 |
| | Asian | 0 |
| | More than one | 3 |
| | Unknown | 6 |
| MYCN | | Amplified = 45 |
| | | Non = 45 |
| | | Unknown = 4 |
| Histology | | Unfavorable: 43 |
| | | Favorable = 5 |
| | | Unknown = 46 |
| Diploidy | | >1 = 15 = 1 = 14 |
| | | Unknown = 65 |

TABLE 10-continued

| Patient characteristics. | |
| --- | --- |
| Characteristics | Stratum 1 |
| Response to initial therapy after induction | CR 24 |
| | VGPR 13 |
| | PR 18 |
| | SD 2 |
| | PD 0 |
| | Unknown = 37 |
| Number of ASCTs | 0 = 3 |
| | 1 = 79 |
| | 2 = 7 |
| | Unknown = 5 |
| Enrolled on ANBL0032 | 74/94 = 79% |
| Median Time from diagnosis to DMFO | 1.3 years |

Figure 6A:
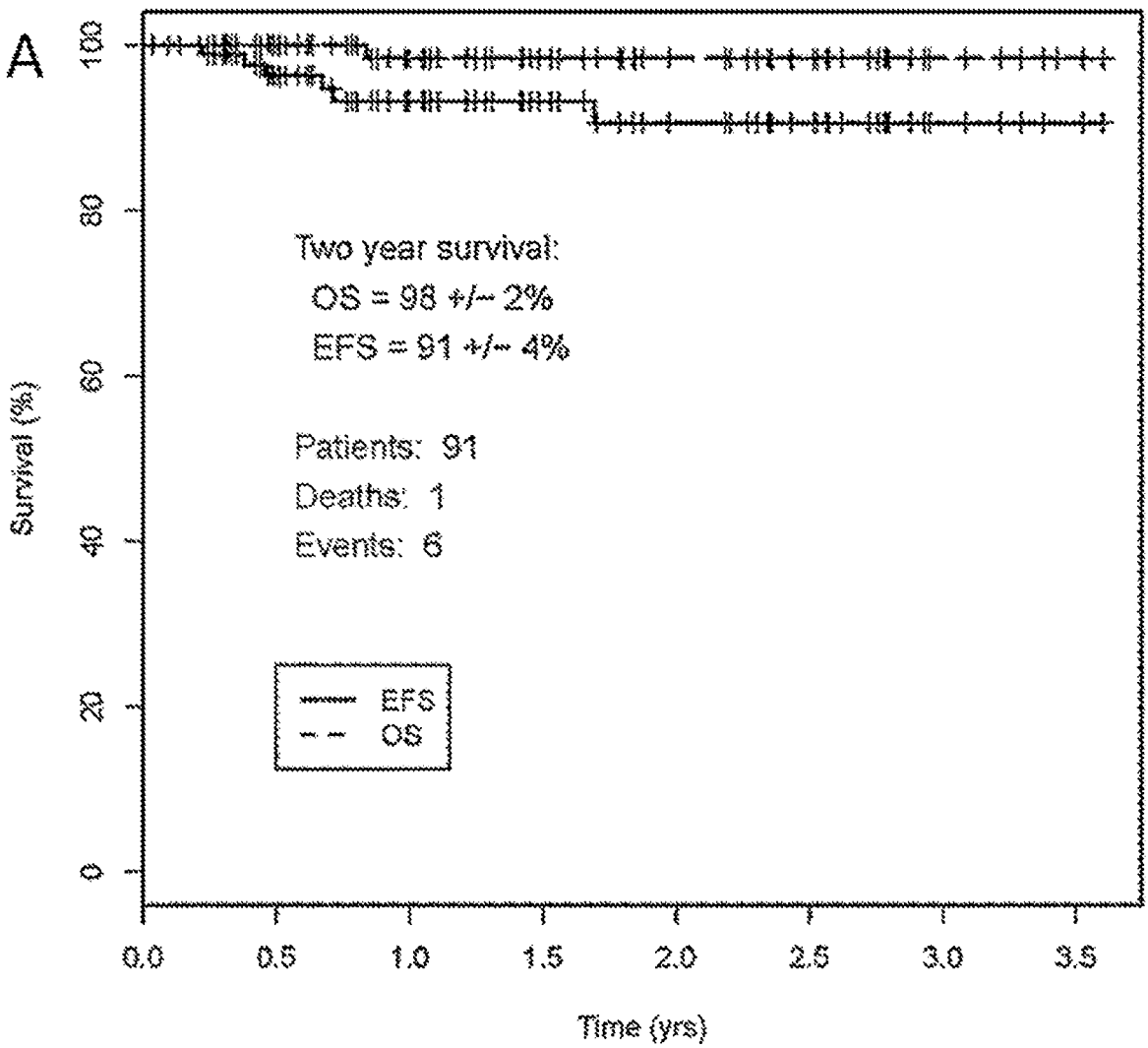
FIGS. 6A-C. EFS and OS for ITT population.
Figure 6B:
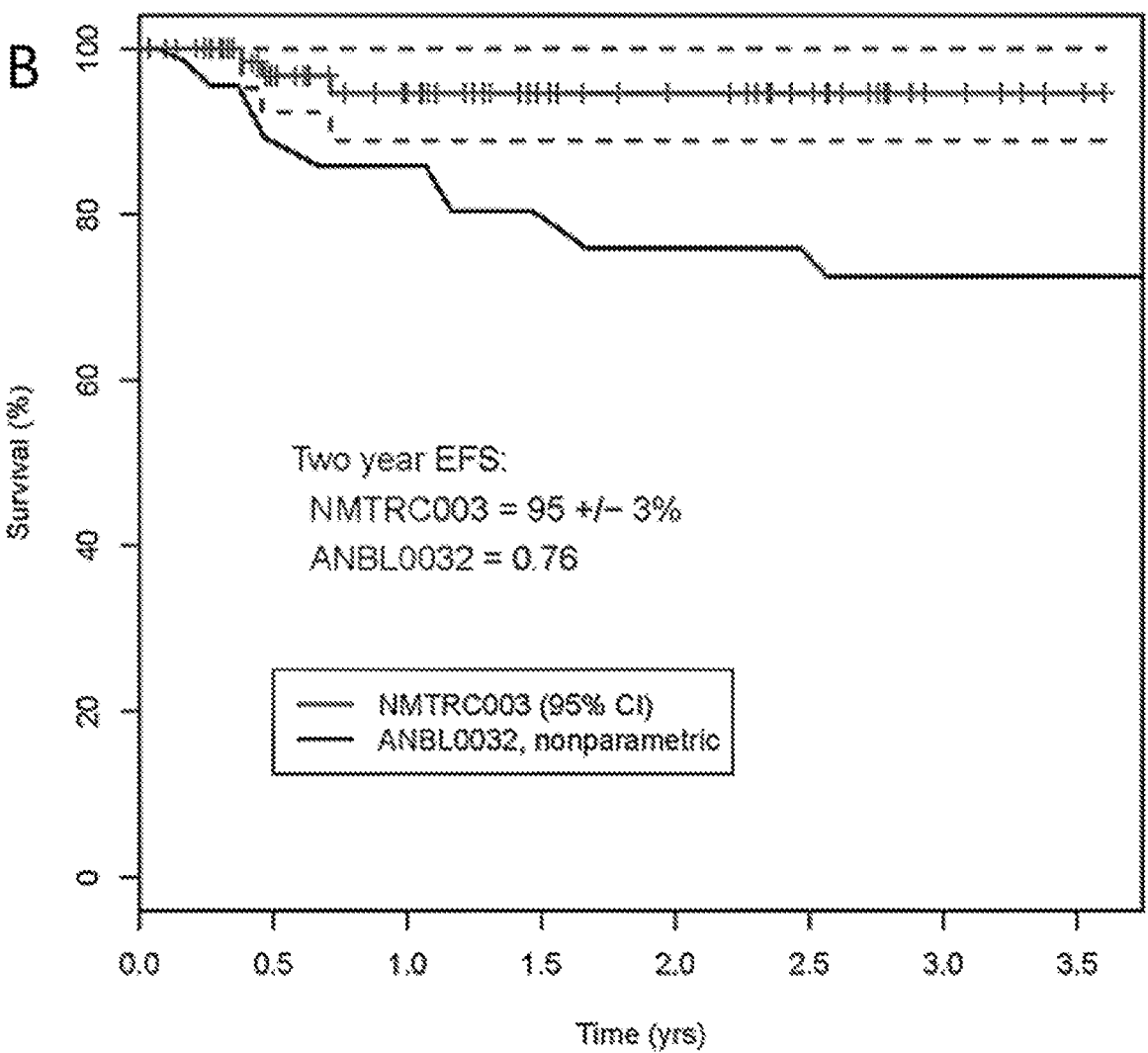

Response. Among all subjects who received DFMO, the 2-year EFS was 91% (±4%) and OS was 98% (±2%) (FIG. 6). None of the subjects who have successfully completed all 27 cycles of therapy have relapsed, with a follow up period of up to 3.5 years. The one subject who relapsed and subsequently died from disease received only 50% dosing due to parent error.

Figure 6C:
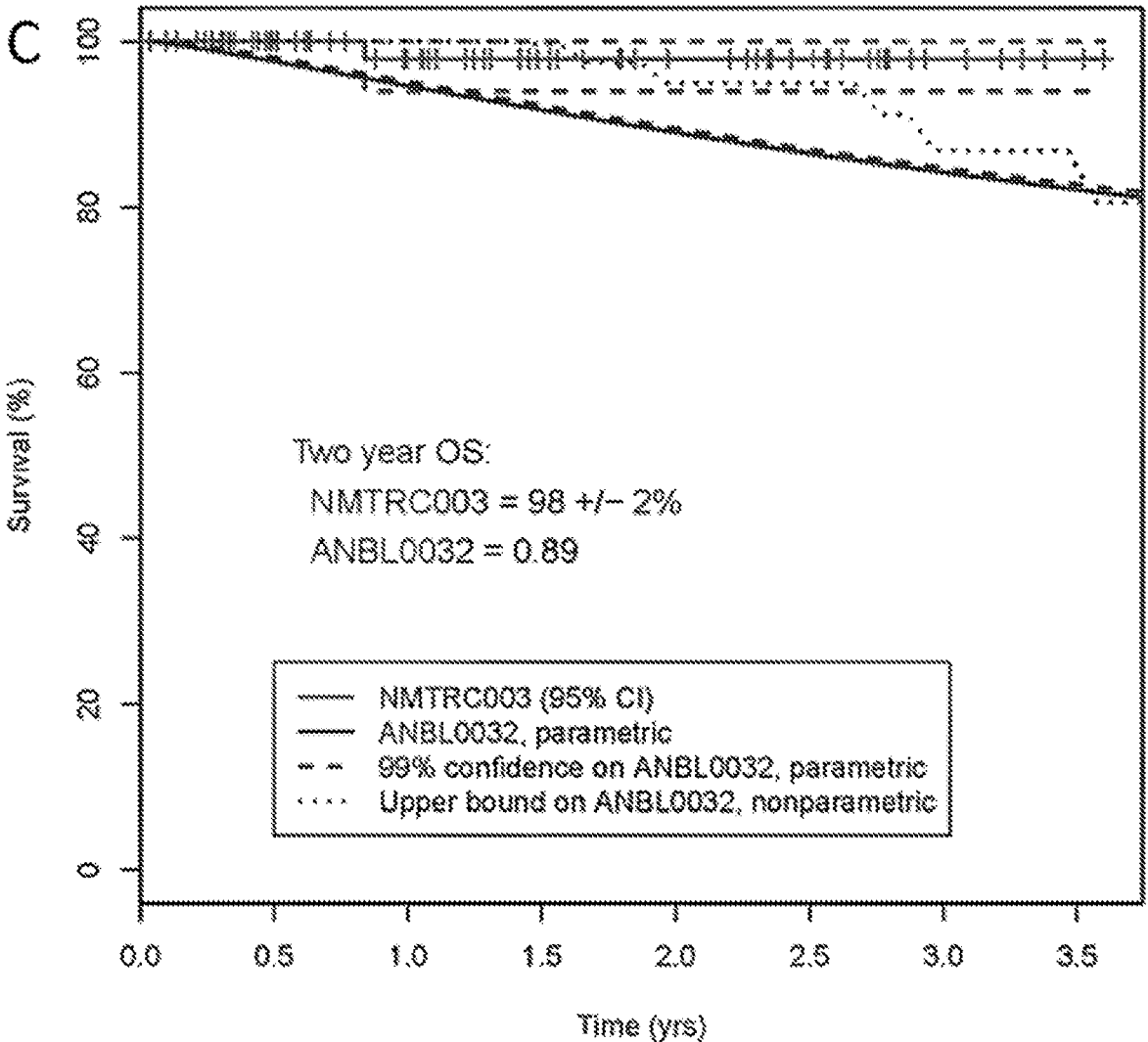

For comparison, published survival data from Children's Oncology Group ANBL0032 were analyzed. Because approximately 12% of subjects treated on ANBL0032 progressed during the 6 months of antibody+retinoic acid therapy, survival curves were analyzed in order to correct for the events during this lead-in time. Starting from the earliest possible start of DFMO therapy (day 1 post completion of ANBL0032 therapy) until the last day that a subject could initiate DFMO (120 days after the last dose of retinoic acid), the estimated 2-year EFS was 71-76%. Using this baseline as comparison, subjects who were previously enrolled on COG ANBL0032 and subsequently received DFMO (n=74) had significantly improved 2-year EFS of 95% (±3%). The OS of patients previously enrolled on ANBL0032 was 98% (±2%), this was also improved relative to the ANBL0032 data based upon the upper bound and/or parametric model (FIG. 6C).

Subjects on ANBL0032 who had a Curie score greater than 0 prior to the start of immunotherapy had a 3 year EFS of 28.9%±6.8%, significantly worse than the 3 year EFS of 71% for those with a Curie score of 0 (Yanik et al., 2013). Evaluation of our subjects treated on ANBL0032 followed by DFMO demonstrate that those with a Curie score greater than 0 (n=4 of 52 with known Curie score) remain in remission.

On further analysis of the 6 subjects who have relapsed to date form the ITT population, 4 were previously enrolled on ANBL0032; the other 2 were not treated according to COG protocols. One of the subjects treated per ANBL0032 was then treated with an additional 6 months of single-agent isotretinoin prior to enrollment on this study. One subject received 8 doses of 3F8 antibody one month apart on an MSKCC protocol and was delayed an additional 120 days prior to starting DFMO. Thus, both of these subjects had initiation of DFMO delayed by 4-6 months relative to patients who did not relapse. Another subject received 50% of DFMO dosing. One subject received pre-DFMO therapy as per a SIOP protocol. Thus, only 2 of these 6 patients had pre-DFMO treatment directly comparable to the ANBL0032 study patients and started therapy within 120 days after completion of 5 cycles of antibody and one cycle of isotretinoin, and received the prescribed dose of DFMO.

Adverse Events. DFMO was well tolerated; 67% of the population did not report any related adverse events over 2 years. Grade 2-3 transaminitis was the most common toxicity and most resolved without holding DFMO (Table 11). Seventy-six percent of patients enrolled on study had pre-existing hearing loss due to previous treatment. Of those, an increase in hearing loss was observed in 4 patients. All cases returned to baseline after holding medication. Two cases resolved within 14 days and drug was resumed at the initial dose, whereas recovery occurred after more than 14 days in the other 2 subjects and they were restarted at a lower dose level. All patients were able to continue on DFMO and complete study regardless of adverse events.

The study reported only one SAE involving hypoglycemia in a child with a viral infection that caused vomiting and diarrhea, and who was unable to tolerate overnight G-tube feeding. The following morning the child was unresponsive and found to have a low blood sugar; the symptoms reversed promptly with administration of glucose and the child recovered fully. The dose of DFMO was reduced as per protocol and this subject has continued on study without recurrence or other adverse events.

TABLE 11

| Stratum 1 adverse events attributed (possibly, probably, or definitely) to DFMO | | | | |
| --- | --- | --- | --- | --- |
| | n = 94 | | | |
| | Grade 2 | Grade 3 | Grade 4 | Grade 5 |
| Hematologic Toxic Effects | | | | |
| Anemia | 4 (4%) | 0 | 0 | 0 |
| Neutrophil count decrease | 4 (4%) | 3 (3%) | 0 | 0 |
| Platelet count decrease | 2 (2%) | 0 | 0 | 0 |
| White blood cell decreased | 2 (2%) | 0 | 0 | 0 |
| Non-hematologic Toxic Effects | | | | |
| Agitation | 1 (1%) | 0 | 0 | 0 |
| Alopecia | 1 (1%) | 0 | 0 | 0 |
| ALT elevation | 3 (3%) | 5 (5%) | 0 | 0 |
| AST elevation | 3 (3%) | 4 (4%) | 0 | 0 |
| Anorexia | 1 (1%) | 0 | 0 | 0 |
| Diarrhea | 5 (5%) | 0 | 0 | 0 |
| Fever | 2 (2%) | 0 | 0 | 0 |
| Hearing Loss | 2 (2%) | 4 (4%) | 0 | 0 |
| Hypoglycemia | 0 | 0 | 1 (1%) | 0 |
| Hypokalemia | 0 | 2 (2%) | 0 | 0 |
| Infection, Other | 2 (2%) | 0 | 0 | 0 |
| Infection, middle ear | 2 (2%) | 0 | 0 | 0 |
| INR Elevated | 1 (1%) | 0 | 0 | 0 |
| Pain | 2 (2%) | 0 | 0 | 0 |
| Post Nasal Drip | 1 (1%) | 0 | 0 | 0 |
| Rash | 1 (1%) | 0 | 0 | 0 |
| Weight Gain | 1 (1%) | 0 | 0 | 0 |

Percentages are calculated as number of patients with an event divided by number of patients in group that received drug.
ALT = alanine aminotransferase
AST = aspartate aminotransferase All of the methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the methods without departing from the spirit, scope, and concept of the invention. All variations and modifications apparent to those skilled in the art are deemed to be within the spirit, scope, and concept of the invention as defined by the appended claims.

67
68

XV. REFERENCES

The following references, to the extent that they provide exemplary procedural or other details supplementary to those set forth herein, are specifically incorporated herein by reference.

U.S. Pat. No. 4,330,559
U.S. Pat. No. 4,413,141
U.S. Pat. No. 4,582,788
U.S. Pat. No. 4,683,194
U.S. Pat. No. 4,683,202
U.S. Pat. No. 4,656,127
U.S. Pat. No. 5,952,174
U.S. Pat. No. 6,258,845
U.S. Pat. No. 6,451,995
U.S. Pat. No. 8,278,065
U.S. Pat. No. 8,507,657
U.S. Patent Appln. Publn. 20130216528
U.S. Patent Appln. Publn. 20140170155
European Patent Application 50,424
European Patent Application 84,796
European Patent Application 258,017
European Patent Application 237,362
European Patent Application 201,184
French Patent 2,650,840
PCT Application WO91/02087
PCT Application WO92/15712
PCT Application WO2014/144763
AACR 2009, Abstract #3203
AACR 2009, Abstract #3208
Alice et al., Update of Outcome for High-Risk Neuroblastoma Treated on a Randomized Trial of chimeric Anti-GD2 Antibody (ch14.18)+GM-CSF/IL2 Immunotherapy in 1st Response: A Children's Oncology Group Study. Advances in Neuroblastoma Research Association 2014.
Alirol et al., Nifurtimox-eflornithine combination therapy for second-stage gambiense human African trypanosomiasis: Medecins Sans Frontieres experience in the Democratic Republic of the Congo, Clin. Infect. Dis., 56:195-203, 2013.
Ater et al., Neuroblastoma screening in the United States: results of the Texas Outreach Program for neuroblastoma screening. Cancer, 82:1593-1602, 1998.
Auvinen et al., Ornithine decarboxylase activity is critical for cell transformation, Nature, 360:355-358, 1992.
Auvinen et al., Ornithine decarboxylase- and ras-induced cell transformations: reversal by protein tyrosine kinase inhibitors and role of pp130CAS, Mol. Cell Biol., 15:6513-6525, 1995.
Auvinen et al., Transcriptional regulation of the ornithine decarboxylase gene by c-Myc/Max/Mad network and retinoblastoma protein interacting with c-Myc, Int. J. Biochem. Cell Biol., 35:496-521, 2003.
Babbar et al., Inflammation and polyamine catabolism: the good, the bad and the ugly, Biochem. Soc. Trans., 35:300-304, 2007.
Bachmann, The role of polyamines in human cancer: prospects for drug combination therapies, Hawaii Med. J., 63:371-374, 2004.
Bachmann et al., "Neuroblastoma: Ornithine decarboxylase and polyamines are novel targets for therapeutic intervention," In: Pediatric Cancer, Neuroblastoma: Diagnosis, Therapy, and Prognosis, Hayat, editor, Springer, pp. 91-103, 2012.
Bailey et al., A randomized, double-blind, placebo controlled phase 3 skin cancer prevention study of {alpha}-difluoromethylornithine in subjects with previous history of skin cancer, Cancer Prev. Res. (Phila.), 3:35-47, 2010.
Bello-Fernandez et al., The ornithine decarboxylase gene is a transcriptional target of c-Myc, Proc. Natl. Acad. Sci. USA, 90:7804-7808, 1993.
Ben-Yosef et al., Involvement of Myc targets in c-myc and N-myc induced human tumors, Oncogene, 17:165-171, 1998.
Berthold, et al., Myeloablative megatherapy with autologous stem-cell rescue versus oral maintenance chemotherapy as consolidation treatment in patients with high-risk neuroblastoma: a randomised controlled trial. Lancet Oncol, 6 (9): 649-658, 2005.
Blume-Peytavi and Hahn, Medical treatment of hirsutism, Dermatol. Ther., 21:329-339, 2008.
Bosslet et al., Monoclonal antibodies against epitopes on ganglioside GD2 and its lactones. Markers for gliomas and neuroblastomas. Cancer Immunol. Immunother., 29:171-178, 1989.
Boyle et al., Polyamine contents in rectal and buccal mucosae in humans treated with oral difluoromethylornithine, Cancer Epidemiology, Biomarkers & Prevention, 1:131-135, 1992.
Bradford, A rapid and sensitive method for the quantitation of microgram quantities of protein utilizing the principle of protein-dye binding, Anal Biochem., 72:248-254, 1976.
Brant et al., Risk factors related to age-associated hearing loss in the speech frequencies, J. Am. Acad. Audiol., 7:152-160, 1996.
Brodeur, Neuroblastoma: biological insights into a clinical enigma. Nat Rev Cancer, 3:203-216, 2003.
Brown et al., Genetic polymorphism in ornithine decarboxylase and risk of breast cancer, Fam. Cancer, 8:307-311, 2009.
Carbone et al., Bioavailability study of oral liquid and tablet forms of alpha-difluoromethylornithine, Clinical Cancer Research, 6:3850-3854, 2000.
Carbone et al., Phase I chemoprevention study of difluoromethylornithine in subjects with organ transplants, Cancer Epidemiol. Biomarkers Prev., 10:657-661, 2001.
Casero and Marton, Targeting polyamine metabolism and function in cancer and other hyperproliferative diseases, Nat. Rev. Drug Discov., 6:373-390, 2007.
Chaffer and Weinberg, How does multistep tumorigenesis really proceed? Cancer Discovery, 5:22-24, 2015.
Chapman, Antitumor effects of vitamin A and inhibitors of ornithine decarboxylase in cultured neuroblastoma and glioma cells, Life Sci, 26:1359-1661, 1980.
Chen et al., Effects of inhibitors of ornithine decarboxylase on the differentiation of mouse neuroblastoma cells, Cancer Res., 43:2812-2818, 1983.
Cheung et al., Ganglioside GD2 specific monoclonal antibody 3F8: a phase I study in patients with neuroblastoma and malignant melanoma. Journal of Clinical Oncology, 5 (9): 1430-1440, 1987.
Cheung et al., 3F8 monoclonal antibody treatment of patients with stage 4 neuroblastoma: a phase II study. Int. J. Oncol., 12:1299-1306, 1998.
Cheung, et al., Murine anti-GD2 monoclonal antibody 3F8 combined with granulocyte-macrophage colony-stimulating factor and 13-cis-retinoic acid in high-risk patients with stage 4 neuroblastoma in first remission. J Clin Oncol, 30 (26): 3264-3270, 2012.
Choi et al., Addiction to multiple oncogenes can be exploited to prevent the emergence of therapeutic resistance, Proc. Natl. Acad. Sci. USA, 111: E3316-3324, 2014.

Chopra and Wallace, Induction of spermidine/spermine N1-acetyltransferase in human cancer cells in response to increased production of reactive oxygen species, *Biochem. Pharmacol.*, 55:1119-1123, 1998.

Croghan et al., Dose-related alpha-difluoromethylornithine ototoxicity, *Am. J. Clin. Oncol.*, 14:331-315, 1991.

Cruickshanks et al., The 5-year incidence and progression of hearing loss: the epidemiology of hearing loss study, *Arch Otolaryngol. Head Neck Surg.*, 129:1041-1046, 2003.

de Arruda et al., *Expert Rev. Mol. Diagn.*, 2:487-496, 2002.

Dorr et al., Modulation of etoposide cytotoxicity and DNA strand scission in L1210 and 8226 cells by polyamines, *Cancer Res.*, 46:3891-3895, 1986.

Doyle et al., Effects of DFMO chemoprevention on audiometry thresholds and otoacoustic emissions, *Arch. Otolaryngology Head and Neck Surgery*, 127:553-558, 2001.

Erdman et al., *Carcinogenesis*, 20:1709-1713, 1999.

Ernestus et al., Polyamine metabolism in brain tumours: diagnostic relevance of quantitative biochemistry, *J. Neurol. Neurosurg. Psychiatry*, 71:88-92, 2001.

Eskens et al., Phase I and pharmacological study of weekly administration of the polyamine synthesis inhibitor SAM 486A (CGP 48 664) in patients with solid tumors. European Organization for Research and Treatment of Cancer Early Clinical Studies Group, *Clin. Cancer Res.*, 6:1736-1743, 2000.

Evageliou and Hogarty, Disrupting polyamine homeostasis as a therapeutic strategy for neuroblastoma, *Clin. Cancer Res.*, 15:5956-5961, 2009.

Fabian et al., A phase II breast cancer chemoprevention trial of oral alpha-difluoromethylornithine: breast tissue, imaging, and serum and urine biomarkers, *Clin. Cancer Res.*, 8:3105-3117, 2002.

Fuller et al., Polyamine biosynthesis and accumulation during the G1 to S phase transition, *J. Cell Physiol.*, 93:81-88, 1977.

Gamble et al., Polyamine pathway inhibition as a novel therapeutic approach to treating neuroblastoma, *Front. Oncol.*, 2:162, 2012.

Garcia-Huidobro et al., Functional consequence of genetic variability in a G-quadruplex structure in the ornithine decarboxylase (odc1) gene. Nucleic Acids Research, submitted, 2014a.

Garcia-Huidobro et al., Intron 1 polymorphisms cooperate to modulate odc1 transcriptional activity and risk of colorectal adenomas. Cancer Research, submitted, 2014b.

Garcia-Huidobro, Molecular and Functional Consequences of Genetic Variability in the Ornithine Decarboxylase Gene in Colorectal Cancer, University of Arizona Dissertation, 2013.

Geerts et al., The polyamine metabolism genes ornithine decarboxylase and antizyme 2 predict aggressive behavior in neuroblastomas with and without MYCN amplification, *Int. J. Cancer*, 126:2012-2024, 2010.

Gerner et al., *Cancer Epidemoil. Biomarkers Prey.*, 3:325-330, 1994.

Gerner and Meyskens, Polyamines and cancer: old molecules, new understanding, *Nature Reviews Cancer*, 4:781-792, 2004.

Gilad et al., Serum microRNAs are promising novel biomarkers, *PLOS ONE*, 3: e3148, 2008.

Gilbert et al., An ion-exchange chromatography procedure for the isolation and concentration of basic amino acids and polyamines from complex biological samples prior to high-performance liquid chromatography, *Anal Biochem.*, 199:86-92, 1991.

Griffin, et al., Phase I trial and pharmacokinetic study of intravenous and oral alpha-difluoromethylornithine. *Invest New Drugs*, 5 (2): 177-86, 1987.

Haegele et al., Decarboxylated-S-adenosylmethionine excretion: a biochemical marker of ornithine decarboxylase inhibition by alpha-difluoromethylornithine, *Cancer Res.*, 47:890-895, 1987.

Halushka et al., *Nat. Genet.*, 22:239-247, 1999.

Harras, Cancer Rates and Risks, National Cancer Institute, NIH Publication, pp. 96-691, 1996.

Heby, Role of polyamines in the control of cell proliferation and differentiation, *Differentiation*, 19:1-20, 1981.

Heby and Persson, Molecular genetics of polyamine synthesis in eukaryotic cells, *Trends Biochem. Sci.*, 15:153-158, 1990.

Hiramatsu et al., N (1),N (12)-Diacetylspermine as a sensitive and specific novel marker for early- and late-stage colorectal and breast cancers, *Clinical Cancer Research*, 11:2986-2990, 2005.

Hixson, et al., Ornithine decarboxylase and polyamines in colorectal neoplasia and mucosa. *Cancer Epidemiol Biomarkers Prev*, 2 (4): 369-374, 1993.

Hixson et al., Sources of variability in estimating ornithine decarboxylase activity and polyamine contents in human colorectal mucosa, *Cancer Epidemiol. Biomarkers Prev.*, 3:317-323, 1994.

Hogarty et al., ODC1 is a critical determinant of MYCN oncogenesis and a therapeutic target in neuroblastoma, *Cancer Res.*, 68:9735-9745, 2008.

Inoue et al., Simultaneous determination of free and N-acetylated polyamines in urine by semimicro high-performance liquid chromatography using 4-(5,6-dimethoxy-2-phthalimidinyl)-2-methoxyphenylsulfonyl chloride as a fluorescent labeling reagent, *Anal Biochem.*, 339:191-197, 2005.

Johnson et al., *Nat. Genet.*, 29:233-237, 2001.

Kaczmarek et al., Cell-cycle-dependent expression of human ornithine decarboxylase, *J. Cell Physiol.*, 132:545-551, 1987.

Kahana and Nathans, Isolation of cloned cDNA encoding mammalian ornithine decarboxylase, *Proc. Natl. Acad. Sci. USA*, 81: 3645-3649, 1984.

Kawakita et al., Determination of N(1),N(1)(2)-diacetylspermine in urine: a novel tumor marker, *Methods Mol. Biol.*, 720:367-378, 2011.

Ke and Cardon, *Bioinformatics*, 19:287-288, 2003.

Komher et al., *Nucl. Acids Res.*, 17:7779-7784, 1989.

Koomoa et al., Ornithine Decarboxylase Inhibition by {alpha}-Difluoromethylornithine Activates Opposing Signaling Pathways via Phosphorylation of Both Akt/Protein Kinase B and p27Kip1 in Neuroblastoma, *Cancer Res.*, 68:9825-9831, 2008.

Koomoa et al., DFMO/eflornithine inhibits migration and invasion downstream of MYCN and involves p27Kip1 activity in neuroblastoma, *Int. J. Oncol.*, 42:1219-1228, 2013.

Koomoa et al., Inhibition of S-adenosylmethionine decarboxylase by the competitive inhibitor SAM486A connects polyamine metabolism with p53-Mdm2-Akt/PKB regulation and apoptotic cell death in neuroblastoma, *Molecular Cancer Therapeutics*, 8:2067-2075, 2009.

Kuppuswamy et al., *Proc. Natl. Acad. Sci. USA*, 88:1143-1147, 1991.

Kushner et al., Ifosfamide, carboplatin, and etoposide for neuroblastoma: a high-dose salvage regimen and review of the literature, *Cancer*, 119:665-671, 2013.

Kushner et al., Oral Etoposide for Refractory and Relapsed Neuroblastoma, *JCO*, 17:3221-3225, 1999.

Kushner et al., Successful multifold dose escalation of anti-GD2 monoclonal antibody 3F8 in patients with neuroblastoma: a phase I study. *Journal of Clinical Oncology: Official Journal of the American Society of Clinical Oncology*, 29 (9): 1168-1174, 2011.

Kwok and Chen, *Curr. Issues Mol. Biol.*, 5:43-60, 2003.

Kwok et al., *Genomics*, 23:138-144, 1994.

Kwok, *Annu. Rev. Genomics Hum. Genet.*, 2:235-258, 2001.

Landegren et al., *Science*, 241:1077-1080, 1988.

Lange et al., Novel interaction of ornithine decarboxylase with sepiapterin reductase regulates neuroblastoma cell proliferation, *J. Mol. Biol.*, 426:332-346, 2014.

Laverdiere, et al., Long-term outcomes in survivors of neuroblastoma: a report from the Childhood Cancer Survivor Study. *J Natl Cancer Inst*, 101 (16): 1131-1140, 2009.

Levin et al., Phase III randomized study of postradiotherapy chemotherapy with combination alpha-difluoromethylornithine-PCV versus PCV for anaplastic gliomas, *Clin. Cancer Res.*, 9:981-990, 2003.

Levin et al., Phase III randomized study of postradiotherapy chemotherapy with alpha-difluoromethylornithine-procarbazine, N-(2-chloroethyl)-N'-cyclohexyl-N-nitrosurea, vincristine (DFMO-PCV) versus PCV for glioblastoma multiforme, *Clin. Cancer Res.*, 6:3878-3884, 2000.

Love et al., *J. Natl. Cancer Inst.*, 85:732-737, 1993.

Love et al., A randomized, placebo-controlled trial of low-dose alpha-difluoromethylornithine in individuals at risk for colorectal cancer, *Cancer Epidemiol. Biomarkers Prev.*, 7:989-992, 1998.

Lozier, et al., Targeting ornithine decarboxylase reverses the LIN28/Let-7 axis and inhibits glycolytic metabolism in neuroblastoma. *Oncotarget*, 6 (1): 196-206, 2015.

Lu et al., The MYCN oncoprotein as a drug development target, *Cancer Lett.*, 197:125-130, 2003.

Lu et al., *Eukaryot. Cell*, 3:1544-1556, 2004.

Lutz et al., Conditional expression of N-myc in human neuroblastoma cells increases expression of alpha-prothymosin and ornithine decarboxylase and accelerates progression into S-phase early after mitogenic stimulation of quiescent cells, *Oncogene*, 13:803-812, 1996.

Mamont et al., Anti-proliferative properties of DL-alpha-difluoromethyl ornithine in cultured cells. A consequence of the irreversible inhibition of ornithine decarboxylase, *Biochem. Biophys. Res. Commun.*, 81:58-66, 1978.

Maris, Recent advances in neuroblastoma, *N. Engl. J. Med.*, 362:2202-2211, 2010.

Martin, et al., Secondary malignant neoplasms after high-dose chemotherapy and autologous stem cell rescue for high-risk neuroblastoma. *Pediatr Blood Cancer*, 61 (8): 1350-1356, 2014.

Martinez et al., Pronounced reduction in adenoma recurrence associated with aspirin use and a polymorphism in the ornithine decarboxylase gene, *Proc. Natl. Acad. Sci. USA*, 100:7859-7864, 2003.

Marton and Morris, Molecular and cellular functions of polyamines. In: Inhibition of Polyamine Metabolism: Biological Significance and Basis for New Therapies, McCann et al., editors, New York: Academic Press, pp. 79-105, 1987.

Marton and Pegg, Polyamines as targets for therapeutic intervention, *Annu. Rev. Pharmacol. Toxicol.*, 35:55-91, 1995.

Maxam, et al., *Proc. Natl. Acad. Sci. USA*, 74:560, 1977.

McCann and Pegg, Ornithine decarboxylase as an enzyme target for therapy, *Pharmacol. Ther.*, 54:195-215, 1992.

McLaren et al., *Cancer Prev. Res.*, 1:514-521, 2008.

Meier, E.L.K.a.P., Nonparametric Estimation from Incomplete Observations. *Journal of the American Statistical Association*, 53 (282): 457-481, 1958.

Melino et al., Correlation between transglutaminase activity and polyamine levels in human neuroblastoma cells. Effect of retinoic acid and alpha-difluoromethylornithine, *Exp. Cell Res.*, 179:429-445, 1988.

Melino et al., Retinoic acid and alpha-difluoromethylornithine induce different expression of neural-specific cell adhesion molecules in differentiating neuroblastoma cells, *Prog. Clin. Biol. Res.*, 366:283-291, 1991.

Metcalf et al., Catalytic irreversible inhibition of mammalian ornithine decarboxylase (E.C. 4.1.1.17) by substrate and product analogs, *J. Am. Chem. Soc.*, 100:2551-2553, 1978.

Meyskens et al., Dose de-escalation chemoprevention trial of 2 difluoromethylornithine in patients with colon polyps, *J. Natl. Cancer Inst.*, 86:1122-1130, 1994.

Meyskens et al., A Randomized Double-Blind Placebo Controlled Phase IIb Trial of Difluoromethylornithine for Colon Cancer Prevention, *Journal of the National Cancer Institute*, 90:1212-1218, 1998.

Meyskens and Gerner, Development of difluoromethylornithine (DFMO) as a chemoprevention agent, *Clin. Cancer Res.*, 5:945-951, 1999.

Meyskens et al., Difluoromethylornithine plus sulindac for the prevention of sporadic colorectal adenomas: a randomized placebo-controlled, double-blind trial, *Cancer Prev. Res. (Phila.)*, 1:32-38, 2008.

Modak and Cheung, Neuroblastoma: Therapeutic strategies for a clinical enigma, *Cancer Treat. Rev.*, 36:307-317, 2010.

Mohan et al., Overexpression of ornithine decarboxylase in prostate cancer and prostatic fluid in humans, *Clin. Cancer Res.*, 5:143-147, 1999.

Mullis et al., *Cold Spring Harbor Symp. Quant. Biol.*, 51:263-273, 1986.

Nickerson et al., *Proc. Natl. Acad. Sci. USA*, 87:8923-8927, 1990.

Norris et al., The ornithine decarboxylase G317A polymorphism is prognostic of outcome in primary neuroblastoma and differentially affects promoter binding by the MYCN oncogene, *Advances in Neuroblastoma Research*, Abstract OR059: 140, 2014.

Nyren et al., *Anal. Biochem.*, 208:171-175, 1993.

Paridaens et al., A phase I study of a new polyamine biosynthesis inhibitor, SAM486A, in cancer patients with solid tumours, *Br. J. Cancer*, 83:594-601, 2000.

Park et al., Children's Oncology Group's 2013 blueprint for research: neuroblastoma, *Pediatr. Blood Cancer*, 60:985-993, 2013.

Pasic et al., Alpha-difluoromethylornithine ototoxicity. Chemoprevention clinical trial results, *Arch. Otolaryngol. Head Neck Surg.*, 123:1281-1286, 1997.

Pauk et al., Positive effects of tactile versus kinesthetic or vestibular stimulation on neuroendocrine and ODC activity in maternally-deprived rat pups. *Life Sciences*, 39 (22): 2081-2087, 1986.

Pegg and Feith, Polyamines and neoplastic growth, *Biochem. Soc. Trans.*, 35:295-299, 2007.

Pegg, Recent advances in the biochemistry of polyamines in eukaryotes, *Biochem. J.*, 234:249-262, 1986.

Pegg, Polyamine metabolism and its importance in neoplastic growth and a target for chemotherapy, *Cancer Res.*, 48:759-774, 1988.

Pena et al., Regulation of human ornithine decarboxylase expression by the c-Myc.Max protein complex, *J. Biol. Chem.*, 268:27277-27285, 1993.

Pendeville et al., The ornithine decarboxylase gene is essential for cell survival during early murine development. *Molecular and Cellular Biology*, 21 (19): 6549-6558, 2001.

Pendyala et al., Urinary and erythrocyte polyamines during the evaluation of oral alpha-difluoromethylornithine in a phase I chemoprevention clinical trial, *Cancer Epidemiol. Biomarkers Prev.*, 2:235-241, 1993.

Pless et al., Clinical efficacy, tolerability, and safety of SAM486A, a novel polyamine biosynthesis inhibitor, in patients with relapsed or refractory non-Hodgkin's lymphoma: results from a phase II multicenter study, *Clin. Cancer Res.*, 10:1299-1305, 2004.

Porter et al., Polyamine inhibitors and analogs as potential anticancer agents. In: Falk symposium on polyamines in the gastrointestinal tract. Dowling et al., editors. Dordrecht, the Netherlands: Kluwer Academic Publishers, pp. 301-22, 1992.

Poulin et al., Mechanism of the irreversible inactivation of mouse ornithine decarboxylase by alpha-difluoromethylornithine. Characterization of sequences at the inhibitor and coenzyme binding sites, *J. Biol. Chem.*, 267:150-158, 1992.

Prezant et al., *Hum. Mutat.*, 1:159-164, 1992.

Priotto et al., Nifurtimox-eflornithine combination therapy for second-stage African *Trypanosoma brucei* gambiense trypanosomiasis: a multicentre, randomised, phase III, non-inferiority trial, *Lancet*, 374:56-64, 2009.

Pugh et al., The genetic landscape of highrisk neuroblastoma, *Nat. Genet.*, 45:279-284, 2013.

Rounbehler et al., Targeting ornithine decarboxylase impairs development of MYCN-amplified neuroblastoma, *Cancer Res.*, 69:547-553, 2009.

Russell and Levy, Polyamine accumulation and biosynthesis in a mouse L1210 leukemia, *Cancer Res.*, 31:248-251, 1971.

Samal et al., AMXT-15, a novel polyamine transport inhibitor, synergizes with DFMO in inhibiting cell proliferation by targeting both ornithine decarboxylase and polyamine transport, *Int. J. Cancer*, 133:1323-1333, 2013.

Sanger et al., *J. Molec. Biol.*, 94:441, 1975.

Santana et al., Disease control intervals in high-risk neuroblastoma, *Cancer*, 112:2796-2801, 2008.

Saulnier Sholler et al., A Phase I Trial of DFMO Targeting Polyamine Addiction in Patients with Relapsed/Refractory Neuroblastoma. *PLOS One*, 10: e0127246, 2015.

Schanberg et al., PKC alpha mediates maternal touch regulation of growth-related gene expression in infant rats. Neuropsychopharmacology: *Official Publication of the American College of Neuropsychopharmacology*, 28 (6): 1026-1030, 2003.

Schiavetti et al., Ten-day schedule oral etoposide therapy in advanced childhood malignancies, *J. Pediatr. Hematol. Oncol.*, 22:119-24, 2000.

Seeger et al., Association of multiple copies of the N-myc oncogene with rapid progression of neuroblastomas, *N. Engl. J. Med.*, 313:1111-1116, 1985.

Seiler et al., Polyamine metabolism as target for cancer chemoprevention (review), *Int. J. Oncol.*, 13:993-1006, 1998.

Sholler et al., A Phase 1 Trial of DFMO as a Single Agent and in Combination with Etoposide in Patients with Refractory or Recurrent Neuroblastoma, *Proc. AACR Annual Meeting*, Abstract LB-179, 2013.

Silva et al., Role of peripheral polyamines in the development of inflammatory pain. *Biochemical Pharmacology*, 82 (3): 269-277, 2011.

Silvestri et al., Oxycodone controlled-release as first-choice therapy for moderate-to-severe cancer pain in Italian patients: results of an open-label, multicentre, observational study. *Clinical Drug Investigation*, 28 (7): 399-407, 2008.

Simon, et al., The incidence of hearing impairment after successful treatment of neuroblastoma. *Klin Padiatr*, 214 (4): 149-152, 2002.

Simon, et al., Consolidation treatment with chimeric anti-GD2-antibody ch14.18 in children older than 1 year with metastatic neuroblastoma. *J Clin Oncol*, 22 (17): 3549-3557, 2004.

Simoneau et al., *J. Natl. Cancer Inst.*, 93:57-59, 2001.

Simoneau et al., The effect of difluoromethylornithine on decreasing prostate size and polyamines in men: results of a year-long phase IIb randomized placebo-controlled chemoprevention trial, *Cancer Epidemiol. Biomarkers Prev.*, 17:292-299, 2008.

Siu et al., A phase I and pharmacokinetic study of SAM486A, a novel polyamine biosynthesis inhibitor, administered on a daily-times-five every-three-week schedule in patients with Advanced solid malignancies, *Clin. Cancer Res.*, 8:2157-2166, 2002.

Slack et al., The p53 regulatory gene MDM2 is a direct transcriptional target of MYCN in neuroblastoma, *Proc. Natl. Acad. Sci. USA*, 102:731-736, 2005.

Slart et al., An animal model of pain produced by systemic administration of an immunotherapeutic anti-ganglioside antibody. *Pain*, 69 (1-2): 119-125, 1997.

Small et al., *N. Engl. J. Med.*, 347:1135-1142, 2002.

Soda, The mechanisms by which polyamines accelerate tumor spread, *J. Exp. Clin. Cancer Res.*, 30:95, 2011.

Sokolov, *Nucl. Acids Res.*, 18:3671, 1990.

Sorkin et al., Antibody directed against GD (2) produces mechanical allodynia, but not thermal hyperalgesia when administered systemically or intrathecally despite its dependence on capsaicin sensitive afferents. *Brain Research*, 930 (1-2): 67-74, 2002.

Sorkin et al., Anti-GD (2) with an FC point mutation reduces complement fixation and decreases antibody-induced allodynia. *Pain*, 149 (1): 135-142, 2010.

Stevens et al., *Biotechniques*, 34:198-203, 2003.

Strejan et al., *Cell Immunol.*, 84:171-184, 1984.

Syvanen et al., *Genomics*, 8:684-692, 1990.

Tabor and Tabor, Polyamines, *Annu. Rev. Biochem.*, 53:749-790, 1984.

Takahashi et al., alpha-difluoromethylornithine induces apoptosis as well as anti-angiogenesis in the inhibition of tumor growth and metastasis in a human gastric cancer model, *Int. J. Cancer*, 85:243-247, 2000.

Therasse et al., New guidelines to evaluate the response to treatment in solid tumors. European Organization for Research and Treatment of Cancer, National Cancer Institute of the United States, National Cancer Institute of Canada, *J. Natl. Cancer Inst.*, 92:205-216, 2000.

Thompson et al., Levels of rectal mucosal polyamines and prostaglandin E2 predict ability of DFMO and sulindac to prevent colorectal adenoma, *Gastroenterology*, 139:797-805, 805 e791, 2010.

Uemura et al., Identification and characterization of a diamine exporter in colon epithelial cells, *J. Biol. Chem.,* 283:26428-26435, 2008.

Uemura et al., Polyamine transport is mediated by both endocytic and solute carrier transport mechanisms in the gastrointestinal tract, *Am. J. Physiol. Gastrointest. Liver Physiol.,* 299: G517-522, 2010.

Ugozzoll et al., *GATA,* 9:107-112, 1992.

van Zuylen et al., Phase I and pharmacokinetic study of the polyamine synthesis inhibitor SAM486A in combination with 5-fluorouracil/leucovorin in metastatic colorectal cancer, *Clin. Cancer Res.,* 10:1949-1955, 2004.

Visvanathan et al., Association among an ornithine decarboxylase polymorphism, androgen receptor gene (CAG) repeat length and prostate cancer risk, *J. Urol.,* 171:652-655, 2004.

Wagner et al., c-Myc induces the expression and activity of ornithine decarboxylase, *Cell Growth Differ.,* 4:879-883, 1993.

Wainwright et al., Distinct mechanisms of cell cycle arrest control the decision between differentiation and senescence in human neuroblastoma cells, *Proc. Natl. Acad. Sci. USA,* 98:9396-9400, 2001.

Wallace et al., Intravenous lidocaine: effects on controlling pain after anti-GD2 antibody therapy in children with neuroblastoma—a report of a series. *Anesthesia and Analgesia,* 85 (4): 794-796, 1997.

Wallace et al., A perspective of polyamine metabolism, *Biochem. J.,* 376:1-14, 2003.

Wallick et al., Key role for p27Kip1, retinoblastoma protein Rb, and MYCN in polyamine inhibitor-induced G1 cell cycle arrest in MYCN-amplified human neuroblastoma cells, *Oncogene,* 24:5606-5618, 2005.

Wang et al., Neonatal deprivation of maternal touch may suppress ornithine decarboxylase via downregulation of the proto-oncogenes c-myc and max. *The Journal of Neuroscience,* 16 (2): 836-842, 1996.

Wang et al., Cloning and characterization of a human polyamine oxidase that is inducible by polyamine analogue exposure, *Cancer Res.,* 61:5370-5373, 2001.

Weinstein and Joe, Mechanisms of disease: Oncogene addiction—a rationale for molecular targeting in cancer therapy, *Nat. Clin. Pract. Oncol.,* 3:448-457, 2006.

Weinstein and Joe, Oncogene addiction, *Cancer Res.,* 68:3077-3080, discussion 3080, 2008.

Weiss et al., Targeted expression of MYCN causes neuroblastoma in transgenic mice. *The EMBO Journal,* 16 (11): 2985-2995, 1997.

Witherspoon et al., Unbiased metabolite profiling indicates that a diminished thymidine pool is the underlying mechanism of colon cancer chemoprevention by alpha-difluoromethylornithine, *Cancer Discov.,* 3:1072-1081, 2013.

Xie et al., Characterization of a diamine exporter in Chinese hamster ovary cells and identification of specific polyamine substrates, *J. Biol. Chem.,* 272:20484-20489, 1997.

Yanik, et al., Semiquantitative mIBG scoring as a prognostic indicator in patients with stage 4 neuroblastoma: a report from the Children's oncology group. *J Nucl Med,* 54 (4): 541-548, 2013.

Yu et al., Anti-GD2 antibody with GM-CSF, interleukin-2, and isotretinoin for neuroblastoma, *N. Engl. J. Med.,* 363:1324-1334, 2010.

Zell et al., Associations of a polymorphism in the ornithine decarboxylase gene with colorectal cancer survival, *Clin. Cancer Res.,* 15:6208-6216, 2009.

Zell et al., Ornithine decarboxylase-1 polymorphism, chemoprevention with eflornithine and sulindac, and outcomes among colorectal adenoma patients. *Journal of the National Cancer Institute,* 102 (19): 1513-1516, 2010.

What is claimed is:

1. A method for reducing the risk of relapse of neuroblastoma in a patient diagnosed with high-risk neuroblastoma, the method comprising:

orally administering to the patient a pharmaceutical composition comprising α-difluoromethylornithine (DFMO) hydrochloride monohydrate;

wherein the pharmaceutical composition is orally administered to the patient twice a day, independent of the patient's food intake;

wherein the oral administration of the pharmaceutical composition twice a day provides to the patient a total daily dose of α-difluoromethylornithine (DFMO) hydrochloride monohydrate, expressed as grams α-difluoromethylornithine (DFMO) hydrochloride monohydrate per $m^2$ body surface area, that is from 0.05 grams/$m^2$ to 5 grams/$m^2$;

wherein the patient has demonstrated at least a partial response to prior therapy and the patient's high-risk neuroblastoma is in remission; and wherein the prior therapy comprises anti-GD2 immunotherapy.

2. The method according to claim 1, wherein the pharmaceutical composition is a powder.

3. The method according to claim 1, wherein the pharmaceutical composition is one or more tablets.

4. The method according to claim 3, wherein each of the one or more tablets comprises 250 mg of α-difluoromethylornithine (DFMO) hydrochloride monohydrate.

5. The method according to claim 1, wherein the prior therapy further comprises chemotherapy.

6. The method according to claim 1, wherein the patient has demonstrated at least a partial response to prior therapy by demonstrating one of the following:

(i) no evidence of neuroblastoma based on anatomical imaging and on pathological assessment of the bone marrow; or (ii) neuroblastoma detected on anatomical imaging that is determined to be metabolically inactive by functional imaging, and no evidence of neuroblastoma in the bone marrow based on pathological assessment of the bone marrow.

7. The method according to claim 1, wherein the patient has demonstrated a complete response to prior therapy.

8. The method according to claim 1, wherein the oral administration of the pharmaceutical composition twice a day provides to the patient a total daily dose of α-difluoromethylornithine (DFMO) hydrochloride monohydrate that is from 1 gram/$m^2$ to 3 grams/$m^2$.

9. The method according to claim 1, wherein the oral administration of the pharmaceutical composition twice a day provides to the patient a total daily dose of α-difluoromethylornithine (DFMO) hydrochloride monohydrate that is from 1 gram/$m^2$ to 2 grams/$m^2$.

10. The method according to claim 1, wherein the amount of α-difluoromethylornithine (DFMO) hydrochloride monohydrate administered to the patient is:

250 mg α-difluoromethylornithine (DFMO) hydrochloride monohydrate twice a day, if the patient has a body surface area that is at least 0.25 $m^2$ and is less than 0.5 $m^2$, 500 mg α-difluoromethylornithine (DFMO) hydrochloride monohydrate twice a day, if the patient has a body surface area that is at least 0.5 m² and is less than 0.75 m², 750 mg α-difluoromethylornithine (DFMO) hydrochloride monohydrate twice a day, if the patient has a body surface area that is at least 0.75 m² and is no greater than 1.5 m², and 1 gram α-difluoromethylornithine (DFMO) hydrochloride monohydrate twice a day, if the patient has a body surface area that is greater than 1.5 m².

11. A method for reducing the risk of relapse of neuroblastoma in a patient diagnosed with high-risk neuroblastoma, the method comprising:

orally administering to the patient a total daily dose of α-difluoromethylornithine (DFMO) hydrochloride monohydrate, expressed as grams α-difluoromethylornithine (DFMO) hydrochloride monohydrate per m² body surface area, that is from 0.05 grams/m² to; 5 grams/m²;

wherein the patient has demonstrated at least a partial response to prior therapy and the patient's high-risk neuroblastoma is in remission; and wherein the prior therapy comprises anti-GD2 immunotherapy.

12. The method according to claim 11, wherein the total daily dose of α-difluoromethylornithine (DFMO) hydrochloride monohydrate is from 1 gram/m² to 2 grams/m².

13. The method according to claim 12, wherein the α-difluoromethylornithine (DFMO) hydrochloride monohydrate is orally administered to the patient in one or more tablets.

14. The method according to claim 13, wherein each of the one or more tablets comprises 250 mg of α-difluoromethylornithine (DFMO) hydrochloride monohydrate.

15. The method according to claim 12, wherein the α-difluoromethylornithine (DFMO) hydrochloride monohydrate is mixed with a liquid or with food prior to said oral administration.

16. The method according to claim 11, wherein the total daily dose of α-difluoromethylornithine (DFMO) hydrochloride monohydrate is orally administered to the patient in two doses of α-difluoromethylornithine (DFMO) hydrochloride monohydrate, wherein said two doses are equal to each other, each being from 0.5 grams/m² to 1 gram/m² of α-difluoromethylornithine (DFMO) hydrochloride monohydrate.

17. The method according to claim 16, wherein each of said two doses of α-difluoromethylornithine (DFMO) hydrochloride monohydrate is administered in one or more tablets.

18. The method according to claim 17, wherein the one or more tablets each provide 250 mg of α-difluoromethylornithine (DFMO) hydrochloride monohydrate.

19. The method according to claim 17, wherein the prior therapy further comprises chemotherapy.

20. The method according to claim 16, wherein the α-difluoromethylornithine (DFMO) hydrochloride monohydrate is mixed with a liquid or with food prior to said oral administration.

21. The method according to claim 16, wherein the prior therapy further comprises chemotherapy.

22. The method according to claim 11, wherein an amount of 250 mg, 500 mg, 750 mg, or 1000 mg of α-difluoromethylornithine (DFMO) hydrochloride monohydrate is administered to the patient twice a day, and wherein the prior therapy further comprises chemotherapy.

23. The method according to claim 22, wherein said amount of α-difluoromethylornithine (DFMO) hydrochloride monohydrate is administered in one or more tablets that each provide 250 mg of α-difluoromethylornithine (DFMO) hydrochloride monohydrate.

24. A method for reducing the risk of relapse of neuroblastoma in a patient diagnosed with high-risk neuroblastoma, the method comprising:

orally administering to the patient a total amount of 250 mg, 500 mg, 1,000 mg, 1,500 mg, or 2,000 mg of α-difluoromethylornithine (DFMO) hydrochloride monohydrate per day; and wherein the patient has demonstrated at least a partial response to prior therapy and the patient's high-risk neuroblastoma is in remission.

25. The method according to claim 24, wherein the prior therapy comprises anti-GD2 immunotherapy.

26. The method according to claim 25, wherein 500 mg, 1,000 mg, 1,500 mg, or 2,000 mg is the total amount of α-difluoromethylornithine (DFMO) hydrochloride monohydrate per day, and the α-difluoromethylornithine (DFMO) hydrochloride monohydrate is administered to the patient twice a day in one or more tablets.

27. The method according to claim 26, wherein the one or more tablets each provide 250 mg of α-difluoromethylornithine (DFMO) hydrochloride monohydrate.

28. The method according to claim 24, wherein 500 mg, 1,000 mg, 1,500 mg, or 2,000 mg is the total amount of α-difluoromethylornithine (DFMO) hydrochloride monohydrate per day, and 250 mg, 500 mg, 750 mg, or 1,000 mg of α-difluoromethylornithine (DFMO) hydrochloride monohydrate is administered to the patient twice a day to provide said total amount per day.

29. The method according to claim 24, wherein 500 mg, 1,000 mg, 1,500 mg, or 2,000 mg is the total amount of α-difluoromethylornithine (DFMO) hydrochloride monohydrate per day, and wherein for a time period of up to two years, said total amount per day is administered to the patient as 250 mg, 500 mg, 750 mg, or 1,000 mg of α-difluoromethylornithine (DFMO) hydrochloride monohydrate twice a day.

30. The method according to claim 24, wherein the prior therapy comprises anti-GD2 immunotherapy and chemotherapy.

\*    \*    \*    \*    \*